US011254702B2

(12) United States Patent
Sharpless et al.

(10) Patent No.: US 11,254,702 B2
(45) Date of Patent: Feb. 22, 2022

(54) THIONYL TETRAFLUORIDE MODIFIED COMPOUNDS AND USES

(71) Applicant: The Scripps Research Institute, La Jolla, CA (US)

(72) Inventors: K. Barry Sharpless, La Jolla, CA (US); Peng Wu, San Diego, CA (US); Suhua Li, San Diego, CA (US); Zilei Liu, San Diego, CA (US); Bing Gao, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 90 days.

(21) Appl. No.: 16/464,988

(22) PCT Filed: Nov. 29, 2017

(86) PCT No.: PCT/US2017/063746
§ 371 (c)(1),
(2) Date: May 29, 2019

(87) PCT Pub. No.: WO2018/102433
PCT Pub. Date: Jun. 7, 2018

(65) Prior Publication Data
US 2019/0284226 A1    Sep. 19, 2019

Related U.S. Application Data

(60) Provisional application No. 62/427,489, filed on Nov. 29, 2016.

(51) Int. Cl.
| | | |
|---|---|---|
| C07J 41/00 | (2006.01) | |
| C07C 381/10 | (2006.01) | |
| C07D 205/04 | (2006.01) | |
| C07D 207/48 | (2006.01) | |
| C07D 211/96 | (2006.01) | |
| C07D 241/04 | (2006.01) | |
| C07D 265/30 | (2006.01) | |
| C07D 309/02 | (2006.01) | |
| C07D 311/02 | (2006.01) | |
| C07D 327/10 | (2006.01) | |
| C07D 405/04 | (2006.01) | |
| C07D 405/14 | (2006.01) | |
| C07D 413/04 | (2006.01) | |
| C07D 417/06 | (2006.01) | |
| C07D 451/04 | (2006.01) | |
| C07D 471/08 | (2006.01) | |
| C07D 473/34 | (2006.01) | |
| C07F 7/18 | (2006.01) | |
| C07D 493/14 | (2006.01) | |
| C07D 311/46 | (2006.01) | |
| C07D 295/26 | (2006.01) | |

(Continued)

(52) U.S. Cl.
CPC ......... *C07J 41/0072* (2013.01); *A61K 47/549* (2017.08); *A61K 47/6807* (2017.08); *C07C 205/04* (2013.01); *C07C 381/10* (2013.01); *C07D 205/04* (2013.01); *C07D 207/48* (2013.01); *C07D 209/14* (2013.01); *C07D 211/96* (2013.01); *C07D 241/04* (2013.01); *C07D 265/30* (2013.01); *C07D 267/14* (2013.01); *C07D 285/10* (2013.01); *C07D 295/26* (2013.01); *C07D 309/02* (2013.01); *C07D 311/02* (2013.01); *C07D 311/46* (2013.01); *C07D 327/10* (2013.01); *C07D 405/04* (2013.01); *C07D 405/14* (2013.01); *C07D 413/04* (2013.01); *C07D 417/06* (2013.01); *C07D 451/04* (2013.01); *C07D 471/08* (2013.01); *C07D 473/34* (2013.01); *C07D 493/14* (2013.01); *C07F 7/1804* (2013.01); *C07H 19/06* (2013.01); *C07H 21/00* (2013.01); *C07J 41/005* (2013.01); *C07J 43/003* (2013.01); *C07B 2200/07* (2013.01); *C07C 2601/14* (2017.05); *C07C 2603/26* (2017.05); *C07C 2603/74* (2017.05); *C07J 51/00* (2013.01)

(58) Field of Classification Search
CPC ... C07D 205/04; C07D 211/96; C07D 265/30
See application file for complete search history.

(56) References Cited

U.S. PATENT DOCUMENTS 2,862,029 A     11/1958   Smith
3,410,669 A  *  11/1968   Cramer ................. C07C 381/10
                                                        423/386

(Continued)

FOREIGN PATENT DOCUMENTS

WO     WO-8910361 A1  *  11/1989   ............. C07H 19/06

OTHER PUBLICATIONS

Ahmad, R. et al., Enzyme Immobilization: An Overview on Nanoparticles as Immobilization Matrix, Biochemistry & Analytical Biochemistry 4 (2), 1-8 (2015).
Birman, V.B., Amidine-Based Catalysts (ABCs): Design, Development, and Applications, Aldrichimica Acta 49 (2), 23-33 (2016).
Cramer, R. et al., Iminosulfur Oxydifluorides, Journal Organic Chemistry 26, 4010-4014 (1961).

(Continued)

*Primary Examiner* — Joseph R Kosack
(74) *Attorney, Agent, or Firm* — Olson & Cepuritis, Ltd.

(57) ABSTRACT

Thionyl tetrafluoride gas reacts efficiently with primary amines to form reactive iminosulfur oxydifluoride compounds. These dual $S^{VI}$—F loaded iminosulfur oxydifluoride compounds, in turn, readily react with secondary amines or aryloxy silyl ethers (ArO—SiR$_3$), yielding the corresponding fused heteroatom-linked substrates. Iminosulfur oxyfluoride polymers also are provided by disclosed methods.

22 Claims, 17 Drawing Sheets

(51) Int. Cl.
*C07D 285/10* (2006.01)
*C07C 205/04* (2006.01)
*C07D 267/14* (2006.01)
*C07D 209/14* (2006.01)
*C07J 43/00* (2006.01)
*A61K 47/54* (2017.01)
*A61K 47/68* (2017.01)
*C07H 19/06* (2006.01)
*C07H 21/00* (2006.01)
*C07J 51/00* (2006.01)

(56) References Cited

U.S. PATENT DOCUMENTS 6,222,064 B1 4/2001 Lal et al.
6,242,645 B1 6/2001 Lal et al.

OTHER PUBLICATIONS

Dong, J. et al., Sulfur(VI) Fluoride Exchange (SuFEex): Another Good Reaction for Click Chemistry, Angew. Chem. Int. 53 (36), 9430-9448 (2014).

Dudley, F.B. et al., Pentafluorosulfur Hypofluorite and Thionyl Tetrafluoride, Journal of American Chemistry Society 78, 1553-1557 (1956).

Gao, B. et al., Bifluoride-Catalysed Sulfur(VI) Fluoride Exchange Reaction For The Synthesis of Polysulfates and Polysulfonates, Nature Chemistry, published online (2007).

Li, S. et al., Multidimensional SuFEx Click Chemistry: Sequential Sulfur(VI) Fluoride Exchange Connections of Diverse Modules Launched From An SOF4 Hub, manuscript pp. 1-17, published as: Angew. Chem. Intl. Ed. 56 (11): 2903-2908, Mar. 6, 2017.

Smith, W.C. et al., Chemistry of Sulfur Tetrafluoride. V. Preparation of Sulfur Oxytetrafluoride and Sulfur Hexafluoride by Oxidation of Sulfur Tetrafluoride, Journal of American Chemistry Society 82, 3838-3840 (1960).

Von Halasz, S. et al., Darstellung von S-Phenoxy-schwefeloxidtrifluorid und einiger S-Phenoxy-schwefeloxidmonofluoridimide, Chem. Ber. 104 (4), 1242-1246 (1971).

Wang, H. et al., SuFEex-Based Polysulfonate Formation From Ethenesulfonyl Fluoride-Amine Adducts, manuscript pp. 1-15, published as: Angew. Chem. Int. Ed. 56 (37): 11203-11208, Sep. 4, 2017.

\* cited by examiner

THIONYL TETRAFLUORIDE MODIFIED COMPOUNDS AND USES

CROSS-REFERENCE TO RELATED APPLICATIONS

This application is a 371 National Stage of International Patent Application No. PCT/US2017/063746, filed on Nov. 29, 2017, which claims the benefit of U.S. Provisional Application Ser. No. 62/427,489 filed on Nov. 29, 2016, each of which is incorporated herein by reference in its entirety.

STATEMENT OF FEDERALLY SPONSORED RESEARCH

This invention was made with government support under Grant Nos. P50 GM103368 and R01 GM117145 awarded by the National Institutes of Health. The government has certain rights in this invention.

FIELD OF INVENTION

This invention relates to use of thionyl tetrafluoride as a polyvalent connector for SuFEx Click Chemistry. More particularly, this invention relates to iminosulfur fluoride compounds, polymers, and methods of preparing such compounds and polymers.

BACKGROUND

The foundation of Click Chemistry as a framework for creating functional molecular assemblies was inspired by the examination of Nature's favorite molecules and, the realization of her preference for making intermolecular connections through carbon-heteroatom linkages. [Ref. 1]. A stringent criteria for a process to earn Click Chemistry status was defined in 2001 [Ref. 1], highlighting the need for near perfect reactions to aid in the rapid synthesis of useful new materials.

The discovery of the Cu(I) catalyzed azide-alkyne cycloaddition reaction (CuAAC; Click I) in 2002 [Ref. 2], has since had a profound influence on the evolution of Click Chemistry, demonstrating immense versatility and application in fields as diverse as materials science [Ref. 3], bioconjugation [Ref. 4] and drug discovery. [Ref. 5, 6].

In 2014, a new Click Chemistry reaction was introduced; SuFEx (Sulfur(VI) Fluoride Exchange; Click II)—a technology for creating molecular connections with absolute reliability. [Ref. 7]. SuFEx exploits a unique $S^{VI}$—F bond activation phenomenon that allows extraction of fluoride through a combination of H-bonding and Lewis acid effects, promoting exchange of $S^{VI}$—F for $S^{VI}$—O and $S^{VI}$—N bonds; a process often mediated by select amine catalysts (e.g. $Et_3N$) [Ref. 8] and silicon functionalized substrates. [Ref. 9-13].

Early in the development of SuFEx, sulfuryl fluoride $(SO_2F_2)$ [Ref. 7, 14] was identified as an excellent sulfur(VI) hub for creating diaryl sulfate links between molecules. Under SuFEx conditions, the latent reactivity of the otherwise stable $S^{VI}$—F bond is roused to react with 'SuFExable' substrates. [Ref. 7, 15].

While this new area of Click Chemistry technology is just emerging, SuFEx has already found several applications, for example: the synthesis of tosylates [Ref. 9] and sulfonyl azides [Ref. 10]; application in polymer chemistry [Ref. 11] and post polymerization modification [Ref. 12, 13]; Suzuki coupling of aryl and heteroaryl fluorosulfates with boronic acids. [Ref. 15]. Of particular significance, however, is the realization of the potential for SuFEx in biological applications. [Ref. 16]. In a recent study, fluorosulfate based probes proved to be remarkable substrates, capable of selectively capturing protein side-chain groups, especially the hydroxyl on tyrosine, in live human cells. [Ref. 16a]. The remarkable chemistry offered by $S^{(VI)}$—F and SuFEx holds much promise for future discovery applications. [Ref. 16]. There is an ongoing need for additional Click Chemistry reactions. The methods described herein address this need.

Seeking to expand the range of useful SuFEx connectors, other sulfur(VI) oxyfluoride gases were considered: $SF_6$ (sulfur hexafluoride) and $O=SF_4$ (thionyl tetrafluoride, also referred to herein as $SOF_4$) (FIG. 1). While $SF_6$ is the most functionalized of these, it is also famously inert. [Ref. 17]. Thionyl tetrafluoride was first reported in 1902 by Moissan and Lebeau [Ref. 18], and is a colorless gas that boils at −49° C. It comprises a structure based on a trigonal bipyramid with the oxygen occupying an equatorial position (FIG. 1). [Ref. 19]. The gas is classically prepared by reacting $SOF_2$ with $F_2$; [Ref. 18] a process that benefits from a silver fluoride catalyst. [Ref. 20]. An improved synthesis of $O=SF_4$, i.e., for labs with no access to $F_2$, was reported in 1960 by Smith and Engelhardt at CRD DuPont in Wilmington, who found that in the presence of a catalytic amount of $NO_2$, the oxidation of $SF_4$ by $O_2$ was enhanced, giving good yields of the $O=SF_4$ gas. [Ref. 21].

SUMMARY OF THE INVENTION

Iminosulfur oxydifluoride compounds and derivatives thereof are prepared utilizing thionyl tetrafluorides $(O=SF_4)$.

Iminosulfur oxydifluoride compounds having the formulas $R^1$—N=$SOF_2$ and $R^1$—N=$SO(X^4)_2$ are described herein, in which $R^1$ is an organic group, and each $X^4$ independently is selected from F, or an organic group bonded to S by and oxygen or nitrogen atom. The iminosulfur oxydifluoride compounds are formed by reacting a primary amine with $O=SF_4$ gas or as a solution of $O=SF_4$ in an aprotic solvent such as acetonitrile.

Compounds having the formula $R^3$—NH—SO—NH—$CH(R^4)C(=O)OH$, in which $R^3$ and $R^4$ are organic groups are also described herein. Methods of making such compounds and reactions of such compounds are also described.

Compounds having fluorine substituents are of considerable commercial and technical importance and utility due to the unique properties imparted by the fluorine atom. For example, many fluorine-containing compounds having a reactive fluorine are used as fluorinating agents, catalysts, handles for covalently attaching the compound to another material by replacement of the reactive fluorine, as well as protecting groups for hydroxyl, thiol, and amino substituents. Additionally, reactive sulfur-fluorine bonds can be selectively reacted and transformed into other functional groups, e.g., as described in US2015/034516 to Dong et al.

Compounds including substituted iminosulfuroxy groups, e.g., —N=$SOR_2$ in which each R is an organic group bonded to S by a covalent bond, an oxygen atom, or a nitrogen atom, are useful as electron-withdrawing functional groups, catalysts, solvents (in the case of liquid compounds), as well as being a linking group for attaching multiple organic compounds together.

The following embodiments illustrate certain aspects of the compounds and methods described herein.

Embodiment 1 is a compound of formula $R^1$—N=S(O)$(X^A)_2$. $R^1$ comprises at least one first organic moiety selected from the group consisting of hydrocarbyl (e.g., alkyl, aryl, alkylaryl, arylalkyl, a terpene, an alkene, a steroid, an alkyne) a terpenoid, a heterocycle, an alkenyl-substituted aryl, an alkynyl-substituted aryl, a carbohydrate, a polymer, an amino acid, a polypeptide, a nucleotide, a nucleic acid, an enzyme, —CH($R^2$)—C(=O)OH (wherein $R^2$ is H or a second organic moiety), and a nucleoside moiety. Each $X^A$ independently is F, $OR^X$, $N(R^X)_2$, NHet, or $R^X$; each $R^X$ independently is a third organic moiety; NHet comprises a heterocyclic moiety bonded to S by a nitrogen-sulfur covalent bond; with the provisos that when $R^1$ is alkyl, aryl, alkylaryl, arylalkyl, a terpene, a terpenoid, an alkene, an alkyne, an alkenyl-substituted aryl, or an alkynyl-substituted aryl, then one at least $X^A$ is $OR^X$, $N(R^X)_2$, NHet, or $R^X$. When both $X^A$ groups are F, the compounds are iminosulfur oxydifluorides. Non-limiting examples of compounds of Embodiment 1 are shown in Examples 4-47 and 55-84, below, and in FIGS. 2A, 2B, 3, 4, 6, 7, and 11.

Embodiment 2 is a compound of Embodiment 1, wherein $R^1$ is or comprises a nucleoside moiety selected from the group consisting of:

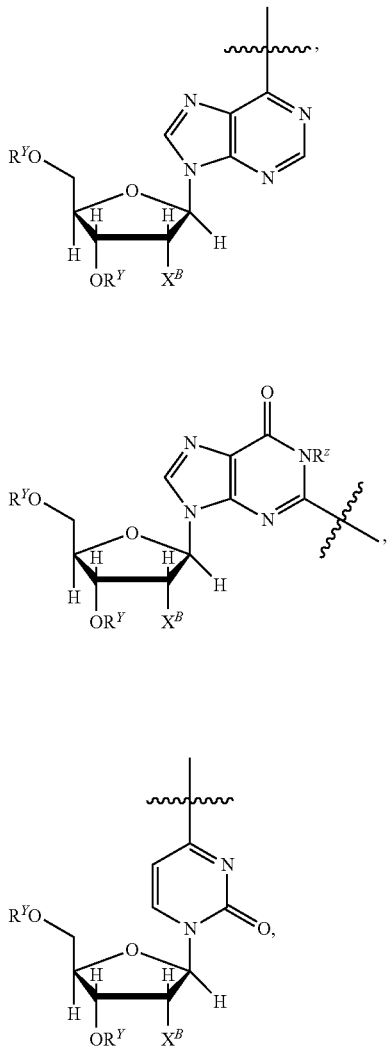

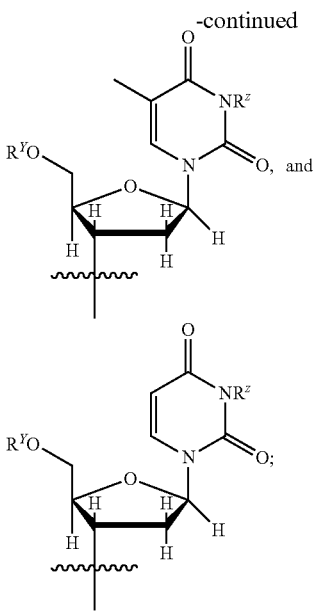

wherein each $R^Y$ independently is H, phosphate, a phosphate ester, sulfate, a sulfate ester, or a fourth organic moiety; and each $R^Z$ independently is a fifth organic moiety. Non-limiting examples of the compounds of Embodiment 2 are shown in Examples 25, 26, 46, and 55, below.

Embodiment 3 is the compound of Embodiment 1 or 2, wherein $R^1$ is or comprises an alkynyl-substituted phenyl group, such as, e.g., shown in Examples 6, 34-43, 47, 53, 59, 61, and 66-71, below.

Embodiment 4 is the compound of any one of Embodiments 1 to 3, wherein $R^1$ comprises an alkynyl group, such as, e.g., shown in Examples 6, 17, 25, 34-43, 46, 47, 53, 55, 59, 61, and 66-71, below.

Embodiment 5 is the compound of Embodiment 1, wherein $R^1$ is —CH($R^2$)—C(=O)OH; and $R^2$ is H or a side chain of an amino acid selected from the group consisting of alanine, arginine, asparagine, aspartic acid, cysteine, glutamic acid, glutamine, histidine, isoleucine, leucine, lysine, methionine, phenylalanine, proline, serine, threonine, tryptophan, tyrosine, valine, ornithine, 2,6-dimethyltyrosine, O-methyl-tyrosine, and para-amino-phenylalanine, such as is shown in Example 14, below.

Embodiment 6 is a compound of Embodiment 1, wherein $R^1$ is an amino-substituted polymer and the —N=S(O)$(X^A)_2$ replaces at least one amino group thereof. Non-limiting examples of some primary amino-substituted polymers include amino-substituted polystyrene, polylysine, amino-substituted polyethylene copolymers, amino-substituted polyethers, polyallylamine and copolymers thereof (e.g., acrylamide-allylamine copolymers, N-vinylpyrrolidone-allylamine copolymers, acrylamide-allylamine copolymers, and the like), branched polyethyleneimines, and the like.

Embodiment 7 is a compound of Embodiment 1, wherein $R^1$ is a polypeptide.

Embodiment 8 is a compound of Embodiment 7, wherein the polypeptide comprises a lysine residue and the —N=S(O)$(X^A)_2$ replaces the sidechain amino group of the lysine residue.

Embodiment 9 is the compound of any one of Embodiments 1 to 8, wherein the $R^1$ comprises one or more substituents selected from the group consisting of functional groups hydroxyl, halogen, nitro, —C(O)R$^{30}$, —C(O)OR$^{30}$, —C(O)N(R$^{30}$)$_2$, —CN, —SO$_v$R$^{30}$, —SO$_v$N(R$^{30}$)$_2$, R$^{30}$SO$_v$N(R$^{30}$)—, —N(R$^{30}$)SO$_v$R$^{30}$, —SO$_3$R$^{30}$, —N(R$^{30}$)$_2$, —N(R$^{30}$)OR$^{30}$, —N(R$^{30}$)C(O)R$^{30}$, —N(R$^{30}$)C(O)OR$^{30}$, —N(R$^{30}$)C(O)N(R$^{30}$)$_2$, —OC(O)N(R$^{30}$)$_2$, —OC(O)OR$^{30}$, azido, alkyl, cycloalkyl, alkenyl, alkynyl, alkoxy, fluoroalkyl, fluoroalkoxy, aryl, aryloxy, heteroaryl, poly(ethyleneoxy), alkynyl-terminated poly(ethyleneoxy), a fatty acid, a carbohydrate, an amino acid, a polypeptide; wherein each R$^{30}$ independently is H, alkyl, or aryl, and v is 0, 1, or 2. Non-limiting examples of the compounds of Embodiment 10 are shown in Examples 5-47, and 52-71, below.

Embodiment 10 is the compound of any one of Embodiments 1 to 9, wherein at least one X$^A$ is F. Non-limiting examples of the compounds of Embodiment 10 are shown in Examples 4-47, 55-59, 70-76 and 78, below.

Embodiment 11 is the compound of any one of Embodiments 1 to 10, wherein at least one X$^A$ is N(R$^X$)$_2$. Non-limiting examples of the compounds of Embodiment 11 are shown in Examples 34-47, 62-64, 70 and 71, below.

Embodiment 12 is the compound of any one of Embodiments 1 to 10, wherein at least one X$^A$ is NHet and comprises a heterocyclic ring selected from the group consisting of an aziridine ring, an azetidine ring, a pyrrolidine ring, a piperidine ring, a piperazine ring, a morpholine ring, a thiazolidine ring, and a thiomorpholine ring. Non-limiting examples of the compounds of Embodiment 12 are shown in Examples 37-43, below.

Embodiment 13 is the compound of any one of Embodiments 1 to 10, wherein at least one X$^A$ is NHet and comprises a heterocyclic ring selected from the group consisting of a pyrrole ring, an imidazole ring, a pyrazole ring, a 1,2,3-triazole ring, a 1,2,4-triazole ring, a tetrazole ring, an indole ring, a benzimidazole ring, a benzotriazole ring, and a purine ring.

Embodiment 14 is the compound of any one of Embodiments 1 to 13, wherein at least one X$^A$ is OR$^X$. Non-limiting examples of the compounds of Embodiment 14 are shown in Examples 52-59, 61-71 and 73-77, below and in FIGS. 6-10, 12A, 12B and 13.

Embodiment 15 is the compound of any one of Embodiments 1 to 14, wherein at least one X$^A$ is R$^X$ (e.g., alkyl, aryl, heteroaryl, and the like, preferably aryl or heteroaryl) such as shown, e.g., in Examples 80 to 83, below.

Embodiment 16 is the compound of any one of Embodiments 1 to 11, wherein both X$^A$ groups are F (i.e., iminosulfur oxydifluorides). Non-limiting examples of the compounds of Embodiment 16 are shown in Examples 4-32, 76, and 84, below, and in FIGS. 2A, 2B, 3 and 11.

Embodiment 17 is the compound of any one of Embodiments 1 to 9, wherein both X$^A$ groups are N(R$^X$)$_2$, such as is shown in Example 27, below.

Embodiment 18 is the compound of any one of Embodiments 1 to 9, 12 and 13, wherein both X$^A$ groups are NHet.

Embodiment 19 is the compound of any one of Embodiments 1 to 9, and 14, wherein both X$^A$ groups are OR$^X$. Non-limiting examples of the compounds of Embodiment 19 are shown in Examples 60, 61, and 66-69, below, and in FIG. 8.

Embodiment 20 is the compound of any one of Embodiments 1 to 9, and 15, wherein both X$^A$ groups are R$^X$ (e.g., alkyl, aryl, heteroaryl, and the like, preferably at least one R$^X$ being aryl or heteroaryl) such as shown, e.g., in Example 81, below.

Embodiment 21 is a compound of formula R$^3$—NH—SO—NH—CH(R$^4$)C(=O)OH, wherein R$^3$ is an organic group, and R$^4$ is H or an organic group. Non-limiting examples of the compounds of Embodiment 21 are shown in Examples 49, 50 and 51.

Embodiment 22 is the compound of Embodiment 21, wherein R$^4$ is H or a side chain of an amino acid selected from the group consisting of alanine, arginine, asparagine, aspartic acid, cysteine, glutamic acid, glutamine, histidine, isoleucine, leucine, lysine, methionine, phenylalanine, proline, serine, threonine, tryptophan, tyrosine, valine, ornithine, 2,6-dimethyltyrosine, O-methyl-tyrosine, and para-amino-phenylalanine. Non-limiting examples of the compounds of Embodiment 22 are shown in Examples 49, 50 and 51.

Embodiment 23 is a method for preparing an iminosulfur oxydifluoride compound of Embodiment 16, comprising contacting an amino compound of formula R$^1$—NX$_2$ with thionyl tetrafluoride (O=SF$_4$) to form an iminosulfur oxydifluoride compound of formula R$^1$—N=SOF$_2$; wherein each X independently is H or Si(R$^{16}$)$_3$; and each R$^{16}$ independently is an alkyl group, an aryl group, an arylalkyl group or an alkylaryl group; with the proviso that when both X groups are H, the amino compound is contacted with the SOF$_4$ in the presence of a tertiary amine. The O=SF$_4$ can be supplied as a gas or as a solution in an aprotic solvent such as acetonitrile. Non-limiting examples of the method of Embodiment 23 are shown in Examples 4-43 and 84, below.

Embodiment 24 is the method of Embodiment 23, wherein each X is H. Non-limiting examples of the method of Embodiment 23 are shown in Examples 4-43 and 84, below.

Embodiment 25 is the method of Embodiment 23, wherein one X is H and one X is Si(R$^{16}$)$_3$.

Embodiment 26 is the method of Embodiment 23, wherein both X groups are Si(R$^{16}$)$_3$.

Embodiment 27 is a method for preparing a sulfamoyl amino acid compound of Embodiment 21, the method comprising contacting a compound of formula R$^3$—N=SOF$_2$ with an alpha-amino acid of formula H$_2$N—CH(R$^4$)C(=O)OH in the presence of a tertiary amine in a solvent at a buffered pH of about 7 to 7.4 to form the sulfamoyl amino acid compound wherein R$^4$ is H or a sixth organic moiety. Non-limiting examples of the method of Embodiment 27 are shown in Examples 49, 50 and 51, below.

Embodiment 28 is the method of Embodiment 27, wherein R$^4$ is H or a side chain of an amino acid selected from the group consisting of alanine, arginine, asparagine, aspartic acid, cysteine, glutamic acid, glutamine, histidine, isoleucine, leucine, lysine, methionine, phenylalanine, proline, serine, threonine, tryptophan, tyrosine, valine, ornithine, 2,6-dimethyltyrosine, O-methyl-tyrosine, and para-amino-phenylalanine. Non-limiting examples of the method of Embodiment 28 are shown in Examples 49, 50 and 51, below.

Embodiment 29 is a method for preparing a sulfamoyl amino acid compound having the formula R$^1$—NH—SO—NH—CH(R$^{17}$)C(=O)OH, the method comprising contacting a compound of Embodiment 16 with an alpha-amino acid of formula H$_2$N—CH(R$^{17}$)C(=O)OH in the presence of a tertiary amine in a solvent at a buffered pH of about 7 to 7.4 to form the sulfamoyl amino acid compound; wherein R$^{17}$ is H or a sixth organic moiety. Non-limiting examples of the method of Embodiment 29 are shown in Examples 49, 50 and 51, below.

Embodiment 30 is a method of Embodiment 29, wherein R$^{17}$ is H or a side chain of an amino acid selected from the group consisting of alanine, arginine, asparagine, aspartic acid, cysteine, glutamic acid, glutamine, histidine, isoleucine, leucine, lysine, methionine, phenylalanine, proline, serine, threonine, tryptophan, tyrosine, valine, ornithine, 2,6-dimethyltyrosine, O-methyl-tyrosine, and para-aminophenylalanine. Non-limiting examples of the method of Embodiment 30 are shown in Examples 50 and 51, below.

Embodiment 31 is a method for preparing a sulfurofluoridoimidate compound comprising contacting an iminosulfur oxydifluoride compound of formula $R^{15}$—N=$SOF_2$ with about one molar equivalent of an organosilyl ether compound of formula $R^{18}$—O—Si$(R^{19})_3$ in the presence of a catalyst to form a sulfurofluoridoimidate compound of formula $R^{15}$—N=SO(F)(O—$R^{18}$); wherein $R^{15}$ is a first organic moiety; $R^{18}$ is a second organic moiety; each $R^{19}$ independently is an alkyl group, an aryl group, an arylalkyl group or an alkylaryl group; and the catalyst is selected from at least one member of the group consisting of an amidine base, a guanidine base, a phosphorine base, and a fluorine-containing anion. Non-limiting examples of the method of Embodiment 31 are shown in Examples 53-61, 66-69, 73-74, and 76, below.

Embodiment 32 is a method for preparing a compound of formula $R^{15}$—N=SO(O—$R^{18})_2$ comprising contacting an iminosulfur oxydifluoride compound of formula $R^{15}$—N=$SOF_2$ with about two molar equivalents of an organo silylether compound of formula $R^{18}$—O—Si$(R^{19})_3$ in the presence of a catalyst to form the compound of formula $R^{15}$—N=SO(O—$R^{18})_2$; wherein $R^{15}$ is a first organic moiety; $R^{18}$ is a second organic moiety; each $R^{19}$ independently is an alkyl group, an aryl group, an arylalkyl group or an alkylaryl group; and the catalyst is selected from at least one member of the group consisting of an amidine base, a guanidine base, a phosphorine base, and a fluorine-containing anion. Non-limiting examples of the method of Embodiment 31 are shown in Examples 60, 61, and 66-69, below.

Embodiment 33 is a method for preparing a sulfurimidate compound comprising contacting an iminosulfur oxydifluoride compound of formula $R^{15}$—N=$SOF_2$ with an organo bis-silylether compound of Formula (I):

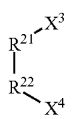

(I)

in the presence of a catalyst to form a sulfurimidate compound of Formula (II):

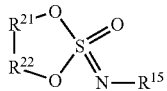

(II)

wherein $R^{15}$ is a first organic moiety; each of $X^3$ and $X^4$ independently is O—Si$(R^{20})_3$; each $R^{20}$ independently is an alkyl group, an aryl group, an arylalkyl group or an alkylaryl group; $R^{21}$ and $R^{22}$ are connected organic moieties in which the $X^3$ and $X^4$ groups are separated from each other by 2, 3, 4, or 5 atoms; and the catalyst is selected from at least one member of the group consisting of an amidine base, a guanidine base, a phosphorine base, and a fluorine-containing anion. Non-limiting examples of the method of Embodiment 33 are shown in Examples 66-69, below.

Embodiment 34 is a method for preparing a sulfuramidoyl fluoride compound comprising contacting a compound of Embodiment 16 with a secondary amine of formula $HNR^X_2$ or a heterocycle HNHet, to form a sulfuramidoyl fluoride compound of formula $R^1$—N=SO(F)($X^A$); wherein $X^A$ is N$(R^X)_2$ or NHet. Non-limiting examples of the method of Embodiment 34 are shown in Examples 34-47, below.

Embodiment 35 is a method for preparing a compound of formula $R^{15}$—N=SO(N$R^{23}R^{24}$)(O—$R^{18}$) comprising contacting a compound of formula $R^{15}$—N=SO(F)(O—$R^{18}$) with a secondary amine of formula $R^{23}$—NH$R^{24}$ to form the compound of formula $R^{15}$—N=SO(N$R^{23}R^{24}$)(O—$R^{18}$); wherein $R^{15}$ is a first organic moiety; $R^{18}$ is a second organic moiety; $R^{23}$ is a third organic moiety; and $R^{24}$ is a fourth organic moiety or H. Non-limiting examples of the method of Embodiment 35 are shown in Examples 63 and 64, below.

Embodiment 36 is a method for preparing a compound of formula $R^{15}$—N=SO(N$R^{23}R^{24}$)(O—$R^{18}$) comprising contacting a sulfuramidoyl fluoride compound of formula $R^{15}$—N=SO(F)(N$R^{23}R^{24}$) with an organo silylether compound of formula $R^{18}$—O—Si$(R^{19})_3$ in the presence of a catalyst to form a sulfonimidate compound of formula $R^{15}$—N=SO(N$R^{23}R^{24}$)(O—$R^{18}$); wherein $R^{15}$ is a first organic moiety; $R^{18}$ is a second organic moiety; each $R^{19}$ independently is an alkyl group, an aryl group, an arylalkyl group or an alkylaryl group; $R^{23}$ is a third organic moiety; $R^{24}$ is a fourth organic moiety or H; and the catalyst is selected from at least one member of the group consisting of an amidine base, a guanidine base, a phosphorine base, and a fluorine-containing anion. A non-limiting example of the method of Embodiment 36 is shown in Example 62, below.

Embodiment 37 is a method for preparing a compound of formula $R^{15}$—N=SO(F)($R^X$); comprising contacting an iminosulfur oxydifluoride compound of formula $R^{15}$—N=$SOF_2$ with an organo lithium compound of formula $R^X$Li (e.g., about 1.3 to 2.2. equiv.); wherein $R^{15}$ is a first organic moiety; and $R^X$ is a second organic moiety. Non-limiting examples of the method of Embodiment 37 are shown in Example 80, below.

Embodiment 38 is the method of Embodiment 37, wherein $R^X$ is an aryl or heteroaryl group. Non-limiting examples of the method of Embodiment 37 are shown in Example 80, below.

Embodiment 39 is a method for preparing a compound of formula $R^{15}$—N=SO$(R^X)_2$; comprising contacting a compound of formula $R^{15}$—N=SO(F)($R^X$) with an organo lithium compound of formula $R^X$Li; wherein $R^{15}$ is a first organic moiety; and $R^X$ is a second organic moiety. Non-limiting examples of the method of Embodiment 39 are shown in Example 81, below.

Embodiment 40 is a method for preparing a compound of formula $R^{15}$—N=SO($R^X$)(O—$R^{18}$) comprising contacting a compound of formula $R^{15}$—N=SO(F)($R^X$) with a silyl ether compound of formula $R^{33}$—O—Si$(R^{34})_3$ in the presence of a catalyst; wherein $R^{15}$ is a first organic moiety; $R^X$ is a second organic moiety; $R^{33}$ is a third organic moiety; each $R^{34}$ independently is an alkyl group, an aryl group, an arylalkyl group or an alkylaryl group; and the catalyst is selected from at least one member of the group consisting of an amidine base, a guanidine base, a phosphorine base, and a fluorine-containing anion. Non-limiting examples of the method of Embodiment 40 are shown in Example 82, below.

Embodiment 41 is a method for preparing a compound of formula $R^{15}$—N=SO($R^X$)(N$R^{35}R^{36}$) comprising contacting a compound of formula $R^{15}$—N=SO(F)($R^X$) with an amino compound of formula $HNR^{35}R^{36}$; wherein $R^{15}$ is a first organic moiety; $R^X$ is a second organic moiety; each $R^{35}$ and $R^{36}$ independently is an organic group, or $R^{35}$ and $R^{36}$ together with the N attached thereto are a heterocyclic group. Non-limiting examples of the method of Embodiment 41 are shown in Example 83, below.

Embodiment 42 is a method of preparing an iminosulfur oxyfluoride polymer comprising contacting a bis-(iminosulfur oxydifluoride) monomer with a bis-(silyl ether) monomer in the presence of a catalyst for the iminosulfur oxyfluoride polymer; wherein the catalyst is selected from at least one member of the group consisting of an amidine base, a guanidine base, a phosphorine base, and a fluorine-containing anion. Non-limiting examples of the method of Embodiment 42 are shown in Examples 73-79, below, and in FIGS. 10, 12A, and 13.

Embodiment 43 is the method of Embodiment 42, wherein the bis(iminosulfur oxydifluoride) monomer is a compound of Formula (III):

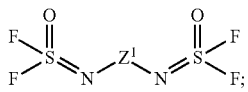

(III)

the bis-(silyl ether) monomer is a compound of Formula (IV):

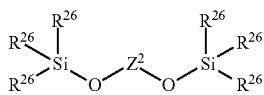

(IV)

and the iminosulfur oxyfluoride polymer is a compound of Formula (V):

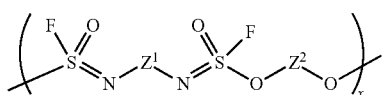

(V)

wherein x is the average number of repeating units in the polymer, and has a value of greater than 1, e.g., greater than 10, greater than 20, greater than 30, greater than 50, greater than 100, greater than 1000; or greater than 10,000; each of $Z^1$ and $Z^2$ independently is a divalent organic group; and each $R^{26}$ independently is an alkyl group, an aryl group, an arylalkyl group or an alkylaryl group. Non-limiting examples of the method of Embodiment 43 are shown in Examples 73-79, below, and in FIGS. 10, 12A, and 13.

Embodiment 44 is the method of Embodiment 43, wherein each of $Z^1$ and/or $Z^2$ independently is a divalent organic group of Formula (VI):

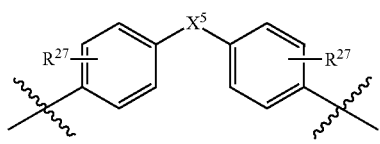

(VI)

wherein $X^5$ is selected from $-CH_2-$, $-CH(R^{28})-$, $-C(R^{28})_2-$, $-R^{28}-$, $-OR^{28}O-$, $-O-$, $-S-$, and $-SO_2-$; each $R^{27}$ independently is a substituent selected from a halogen (e.g., Cl, Br, I), an alkyl, an alkoxy, an aryl, an alkylaryl, an arylalkyl, and a heteroatom-containing substituent comprising one or more oxygen, nitrogen, or sulfur atoms, optionally in combination with carbon and hydrogen (e.g., acyl, acyloxy, amido, and the like); $R^{28}$ is selected from alkyl, aryl, arylalkyl, and alkylaryl; and each y independently is 0, 1, 2, 3, and 4. Non-limiting examples of the method of Embodiment 44 are shown in Example 73, below, and in FIGS. 10 and 12A.

Embodiment 45 is the method of Embodiment 43, wherein each of $Z^1$ and/or $Z^2$ independently is a divalent organic group of Formula (VII):

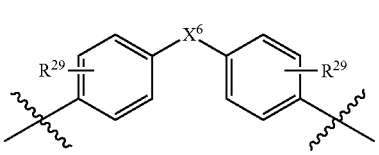

(VII)

wherein each $R^{29}$ independently is a hydrocarbyl group, and $X^6$ is a covalent bond, $-C(CH_3)_2-$, $-C(CF_3)_2-$, or $-SO_2-$. Non-limiting examples of the method of Embodiment 45 are shown in Example 73, below and in FIGS. 10 and 12A.

Embodiment 46 is the method of any one of Embodiments 42 to 45, contacting the bis-(iminosulfur oxydifluoride) monomer and the a bis-(silyl ether) monomer with a crosslinking monomer comprising at least three iminosulfur oxydifluoride groups in the presence of the catalyst to form a crosslinked iminosulfur oxyfluoride polymer. A non-limiting example of the method of Embodiment 46 is shown in Example 76, below.

Embodiment 47 is the method of any one of Embodiments 42 to 46, contacting the bis-(iminosulfur oxydifluoride) monomer and the a bis-(silyl ether) monomer with a crosslinking monomer comprising at least three silyl ether groups in the presence of the catalyst to form a crosslinked iminosulfur oxyfluoride polymer.

Embodiment 48 is an iminosulfur oxyfluoride polymer of Formula (V):

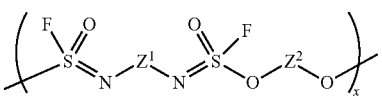

(V)

wherein x is the average number of repeating units in the polymer, and has a value of greater than 1, e.g., greater than 10, greater than 20, greater than 30, greater than 50, greater than 100, greater than 1000; or greater than 10,000; and each of $Z^1$ and $Z^2$ independently is a divalent organic group. Non-limiting examples of the polymer of Embodiment 48 are shown in Example 73, below and in FIGS. 10, 12A, 12B, 12C, and 13.

Embodiment 49 is the polymer of Embodiment 48, wherein each of $Z^1$ and/or $Z^2$ independently is a divalent organic group of Formula (VI):

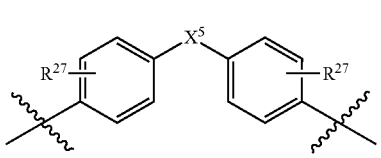

(VI)

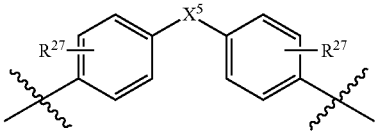

(VI)

wherein $X^5$ is selected from —$CH_2$—, —$CH(R^{28})$—, —$C(R^{28})_2$—, —$R^{28}$—, —$OR^{28}O$—, —O—, —S—, and —$SO_2$—; each $R^{27}$ independently is a substituent selected from a halogen (e.g., Cl, Br, I), an alkyl, an alkoxy, an aryl, an alkylaryl, an arylalkyl, and a heteroatom-containing substituent comprising one or more oxygen, nitrogen, or sulfur atoms, optionally in combination with carbon and hydrogen (e.g., acyl, acyloxy, amido, and the like); $R^{28}$ is selected from alkyl, aryl, arylalkyl, and alkylaryl; and each y independently is 0, 1, 2, 3, and 4. Non-limiting examples of the polymer of Embodiment 49 are shown in Example 73, below and in FIGS. 10, 12A, 12B, and 12C.

Embodiment 50 is the polymer of Embodiment 48, wherein each of $Z^1$ and/or $Z^2$ independently are divalent groups of Formula (VII):

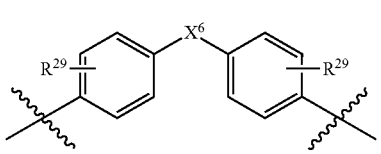

(VII)

wherein each $R^{29}$ independently is a hydrocarbyl group, and $X^6$ is a covalent bond, —$C(CH_3)_2$—, —$C(CF_3)_2$—, or —$SO_2$—. Non-limiting examples of the polymer of Embodiment 47 are shown in Example 73, below and in FIGS. 10, 12A, 12B, and 12C.

Embodiment 51 is the polymer of any one of Embodiments 48 to 50 comprising at least one crosslinking monomer unit, a non-limiting example of which can be found in Example 76, below.

Embodiment 52 is a polymer of Formula (VIII):

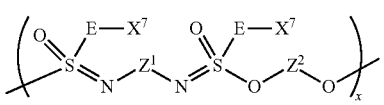

(VIII)

wherein x is the average number of repeating units in the polymer, and has a value of greater than 1, e.g., greater than 10, greater than 20, greater than 30, greater than 50, greater than 100, greater than 1000; or greater than 10,000; and each of $Z^1$ and $Z^2$ independently is a divalent organic group; each $X^7$ of the polymer independently is F or $R^{31}$; at least one $X^7$ is $R^{31}$; and $R^{31}$ is an organic moiety; with the provisos that when $X^7$ is $R^{31}$, E is oxygen or tertiary amino nitrogen; and when $X^7$ is F, E is a covalent bond. Non-limiting examples of the polymer of Embodiment 52 are shown in Examples 73-78, below and in FIG. 10.

Embodiment 53 is the polymer of Embodiment 52, wherein each of $Z^1$ and/or $Z^2$ independently is a divalent organic group of Formula (VI):

wherein $X^5$ is selected from —$CH_2$—, —$CH(R^{28})$—, —$C(R^{28})_2$—, —$R^{28}$—, —$OR^{28}O$—, —O—, —S—, and —$SO_2$—; each $R^{27}$ independently is a substituent selected from a halogen (e.g., Cl, Br, I), an alkyl, an alkoxy, an aryl, an alkylaryl, an arylalkyl, and a heteroatom-containing substituent comprising one or more oxygen, nitrogen, or sulfur atoms, optionally in combination with carbon and hydrogen (e.g., acyl, acyloxy, amido, and the like); $R^{28}$ is selected from alkyl, aryl, arylalkyl, and alkylaryl; and each y independently is 0, 1, 2, 3, and 4. Non-limiting examples of the polymer of Embodiment 53 are shown in Examples 73-75 and 78, below and in FIG. 10.

Embodiment 54 is the polymer of Embodiment 52, wherein each of $Z^1$ and/or $Z^2$ independently are divalent groups of Formula (VII):

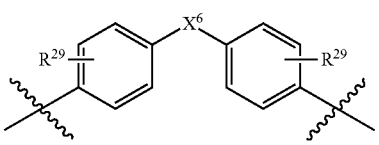

(VII)

wherein each $R^2$ independently is a hydrocarbyl group, and $X^6$ is a covalent bond, —$C(CH_3)_2$—, —$C(CF_3)_2$—, or —$SO_2$—. Non-limiting examples of the polymer of Embodiment 54 are shown in Examples 73-75 and 78, below, and in FIG. 10.

Embodiment 55 is the polymer of any one of Embodiments 52 to 54, wherein at least one $R^{31}$ of the polymer comprises an organic moiety selected from the group consisting of hydrocarbyl (e.g., alkyl, aryl, alkylaryl, arylalkyl, a terpene, an alkene, a steroid, an alkyne) a terpenoid, a heterocycle, an alkenyl-substituted aryl, an alkynyl-substituted aryl, a carbohydrate, an amino acid, a polypeptide, a nucleotide, a nucleic acid, an enzyme, —$CH(R^2)$—$C(=O)$OH (wherein $R^2$ is H or a second organic moiety), and a nucleoside moiety Non-limiting examples of the polymer of Embodiment 55 are shown in Examples 73-75 and 78, below and in FIG. 10.

Embodiment 56 is the polymer of any one of Embodiments 52 to 55, wherein at least one $R^{31}$ of the polymer comprises a heterocyclic moiety. Non-limiting examples of the polymer of Embodiment 56 are shown in Examples 75 and 77, below, and in FIG. 10.

Embodiment 57 is the polymer of any one of Embodiments 52 to 56, wherein at least one $R^{31}$ of the polymer comprises an effector group selected from an antimicrobial agent and a catalyst. A non-limiting example of the polymer of Embodiment 57 is shown in Example 78, below.

Embodiment 58 is the polymer of Embodiment 57, wherein the effector group is an antimicrobial agent selected from at least one member of the group consisting of an antibacterial agent, an antiviral agent, an antifungal agent, and an antiparasitic agent. A non-limiting example of the polymer of Embodiment 58 is shown in Example 78, below.

Embodiment 59 is the polymer of Embodiment 57, wherein the effector group is a catalyst comprising at least one enzyme selected from the group consisting of an oxidoreductase, a transferase, a hydrolase, a lyase, an isomerase, and a ligase.

Embodiment 60 is the polymer of any one of Embodiments 52 to 59, wherein $R^{31}$ comprises at least one terminal alkyne group. Non-limiting examples of the polymer of Embodiment 60 are shown in Examples 74-77, below, and in FIG. 10.

Embodiment 61 is the polymer of Embodiment 60, wherein $R^{31}$ comprises:

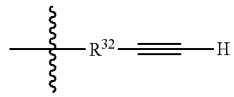

wherein $R^{32}$ is a divalent $C_1$ to $C_{10}$ hydrocarbyl group. Non-limiting examples of the polymer of Embodiment 61 are shown in Examples 74-77, below, and in FIG. 10.

Embodiment 62 is the polymer of any one of Embodiments 60 and 61, wherein $R^{31}$ comprises propargyl or ethynyl-substituted phenyl. Non-limiting examples of the polymer of Embodiment 62 are shown in Examples 74-77, below, and in FIG. 10.

Embodiment 63 is a method of forming a polymer of any one of Embodiments 52 to 62 comprising contacting the polymer of any one of Embodiments 48 to 51 with: (a) a compound of formula $R^{31}$-E-Si$(R^{32})_3$ in the presence of a catalyst, wherein E is oxygen, or (b) a compound of formula $R^{31}$-E-H, wherein E is oxygen or tertiary amino nitrogen; each $R^{32}$ independently is an alkyl group, an aryl group, an arylalkyl group or an alkylaryl group; and wherein the catalyst is selected from at least one member of the group consisting of an amidine base, a guanidine base, a phosphorine base, and a fluorine-containing anion. A non-limiting example of the method of Embodiment 60 is shown in Example 75-78, below.

DETAILED DESCRIPTION

Detailed studies on the SuFEx chemistry of O=$SF_4$ and its iminosulfur oxydifluoride products are reported herein. Presence of tertiary amine bases, such as triethylamine ($Et_3N$) and N,N-diisopropylethylamine (DIPEA) improved reaction rates and yields. The initial products still have two S—F handles, and each fluoride can be substituted in a serial manner by secondary alkyl amines and/or phenols (as their aryl silyl ether under SuFEx catalysis [Ref. 7]). The final products for up to three steps arise in excellent overall yields [Ref 23], thereby allowing controlled projections to be intentionally substituted along three of the four tetrahedral axes departing the S—(VI)-central hub.

Given the fidelity and scope of these three serial transformations, thionyl tetrafluoride (O=$SF_4$) has been identified as another good connective gas for SuFEx Click Chemistry.

First Dimension Connectivity: O=$SF_4$ Reacts with Primary Amines and Anilines

Figure 1:
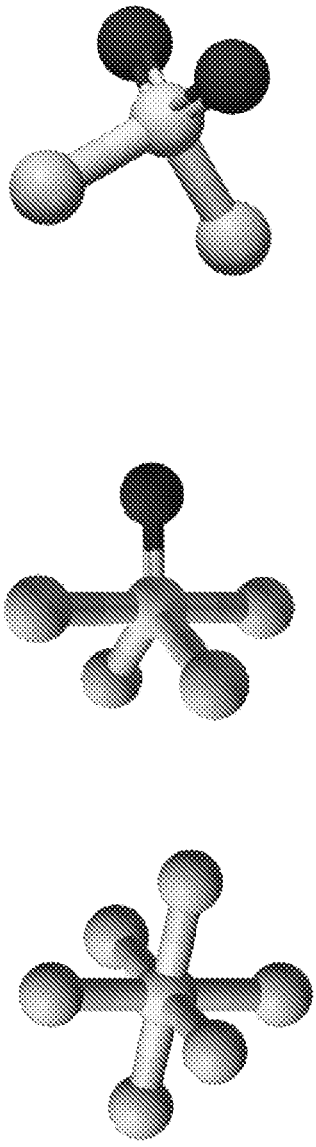
FIG. 1 illustrates structure and boiling point of $SF_6$, O=$SF_4$, and $SO_2F_2$.
Figure 2A:
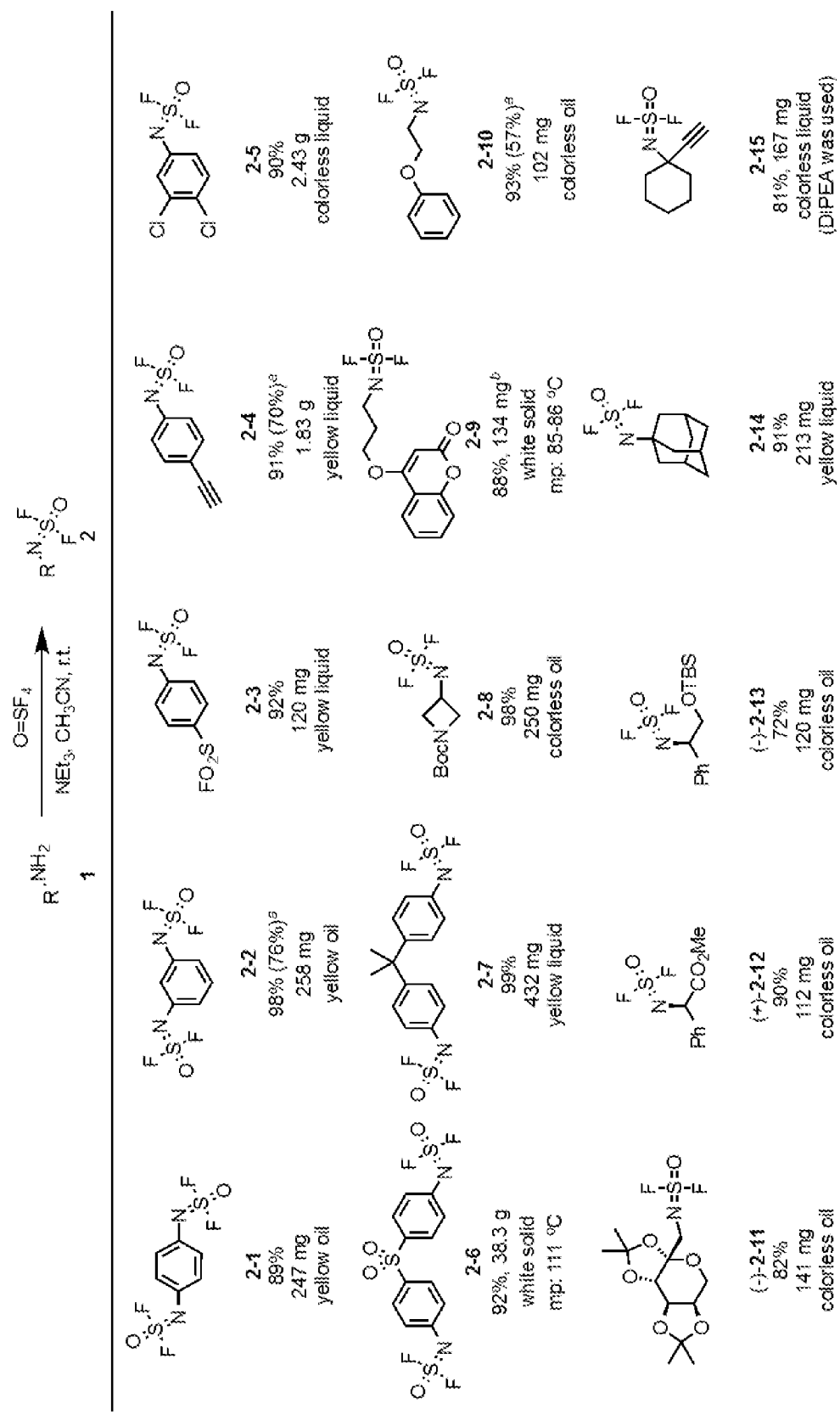
FIG. 2A illustrates the reaction of primary amines with O=$SF_4$ in the presence of $Et_3N$. [a] indicates the reaction without $Et_3N$.
Figure 2B:
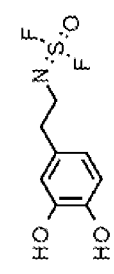
FIG. 2B illustrates additional reactions of primary amines with O=$SF_4$ in the presence of $Et_3N$. [b] indicates the amine was generated in situ by reducing azide under Staudinger conditions with $PMe_3$ and 1 to 3 equiv of $H_2O$.

As described herein, the presence of a tertiary amine base significantly improved the reactions of O=$SF_4$ with primary amines: exposing a solution of primary amine, 1 to 2 mol equiv of $Et_3N$ or DIPEA in $CH_3CN$, to O=$SF_4$ gas, resulted in excellent yields of the tetrahedral iminosulfur oxydifluoride products (FIG. 2). Furthermore, the reactions were chemoselective—reacting preferentially with the primary amine over the other functional groups represented in FIG. 2, for example the catechol 2-16 and the indole 2-17.

The selective decoration of $NH_2$ moieties in biologically significant building blocks was also readily accomplished giving the 'SuFExable' steroid-N=$SOF_2$ cases (FIGS. 2, 2-21 and 2-22) and also the nucleotide-N=$SOF_2$ cases (2-23 and 2-24) in good yields. With the α-amino amide 1-25, intramolecular displacement of the remaining fluoride occurs giving the cyclic sulfamide 2-25 in moderate yield (FIG. 2). Generating the reactive amine in situ, from the corresponding azide under Staudinger conditions, did not adversely affect the yield of the iminosulfur oxydifluoride products (2-9, 2-22, 2-23).

Chemoselectivity of O=$SF_4$: Aniline Vs. Phenols

Noteworthy is the observed chemoselective preference of O=$SF_4$ for aniline vs. phenol (1-16→2-16; FIG. 2); this contrasts with the $SO_2F_2$, which demonstrates the reverse order of preference with aminophenols. [Ref 7,10].

Figure 3:
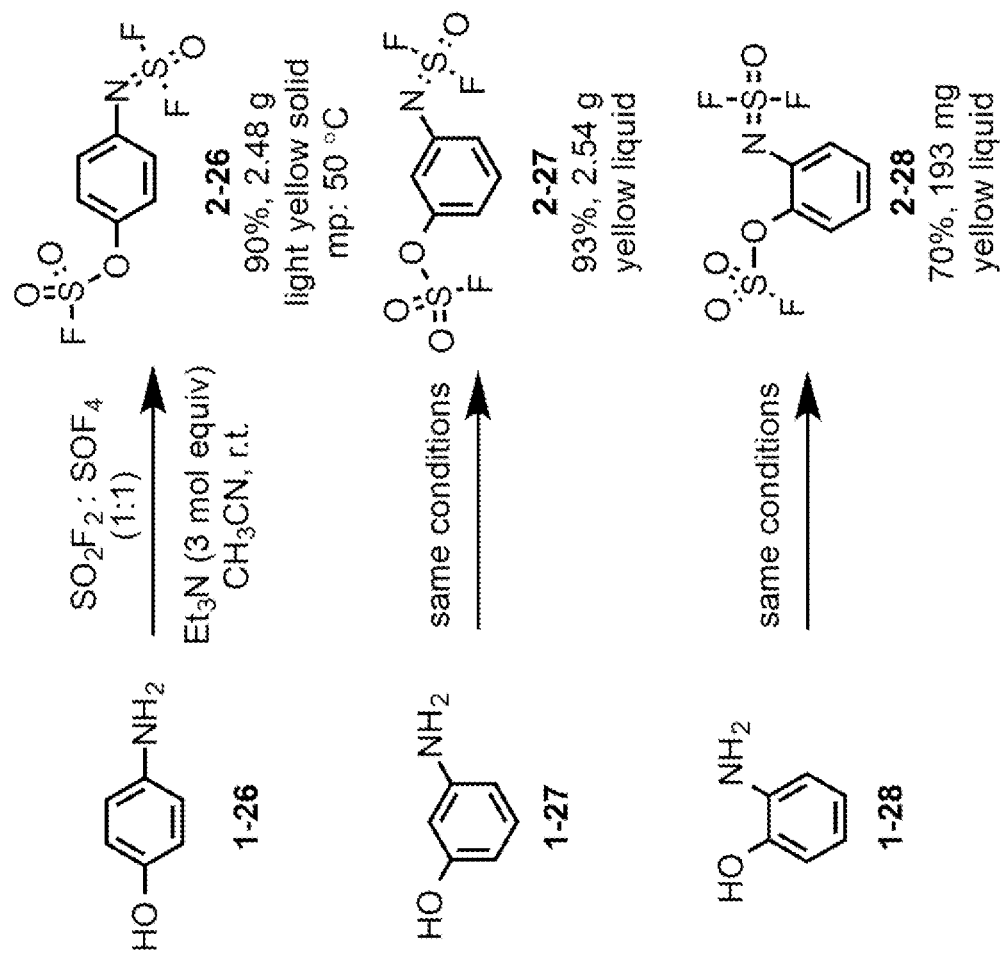
FIG. 3 illustrates the selectivity of $SO_2F_2$ and O=$SF_4$ towards aromatic hydroxyl and amino groups.
Figure 4:
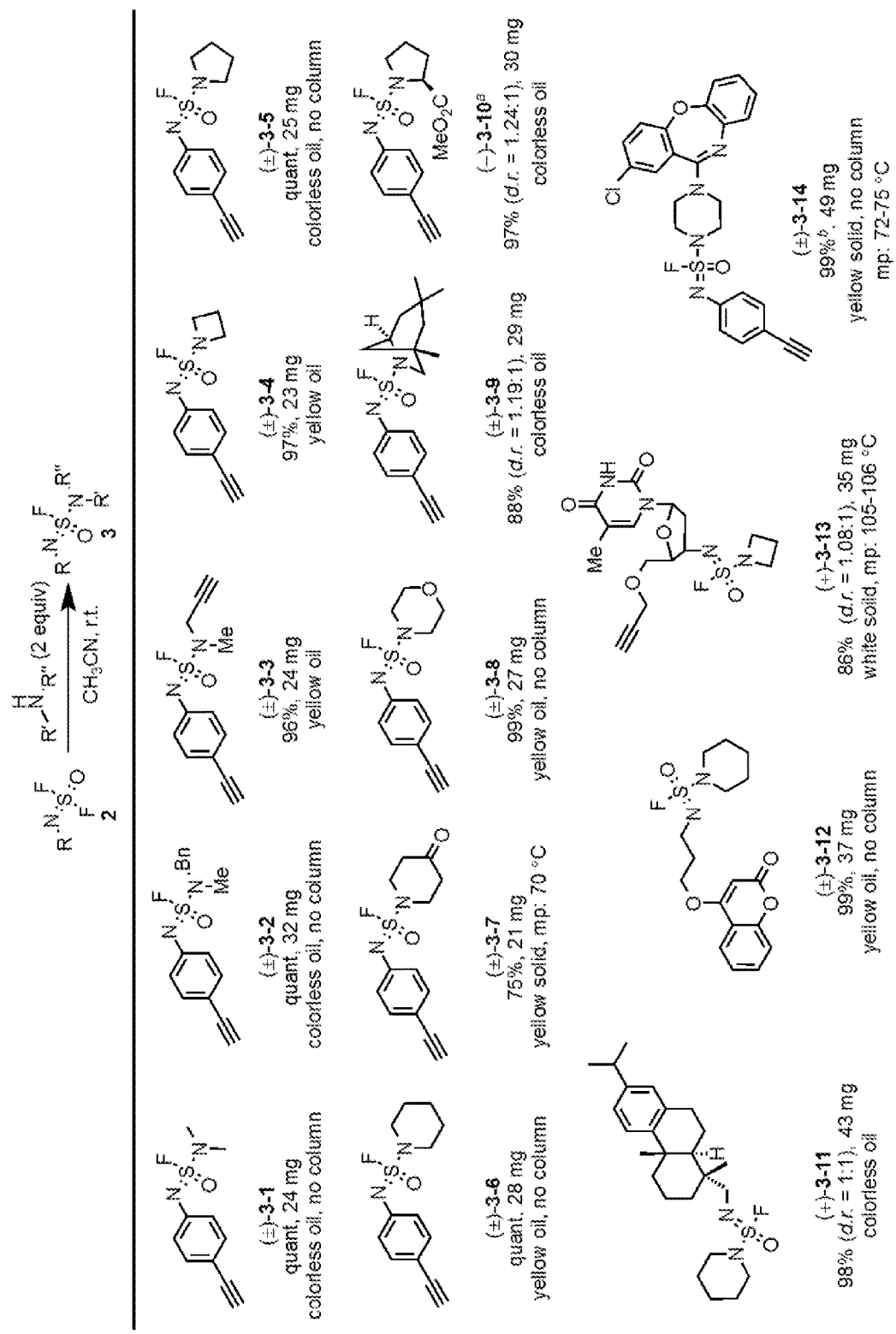
FIG. 4 shows the reaction of iminosulfur oxydifluorides with secondary amines. In [a], 1.2 equiv of proline methyl ester and 2 equiv of $Et_3N$ and in [b], 1 equiv of amoxapine and 2 equiv of $Et_3N$ were used; the solvent was DMSO.

To probe this selectivity effect further, reactions of aminophenols with both gases (O=SF$_4$ and SO$_2$F$_2$) simultaneously were explored. When acetonitrile solutions of the aminophenols 1-26 through 1-28 were exposed to a 1:1 ratio of O=SF$_4$:SO$_2$F$_2$ in the presence of Et$_3$N (3 equiv), the corresponding SuFEx products 2-26 through 2-28 were formed in excellent yields, respectively (FIG. 3). This outcome is explained by the preferential reaction pairing of SO$_2$F$_2$ with phenol and O=SF$_4$ with amine, together with the decreasing opportunities for cross-over reaction for each gas as the reaction proceeds and, at least in the case of the F$_2$OS=N—Ar—OH, the enhanced acidity of the phenol group (FIG. 3). This demonstrates one of the most important principles of Click Chemistry—it should not matter which permutation of the multi-reaction enabled core modules pays off in a given search, for the linking reactions are all near perfect, and no purification is warranted. Benzene, being planar and highly symmetrical [hexagonal, (D$_{6h}$)] has six identical C—H bonds to switch out for substituents, and best known is the family of distributed isomers of which there are three, i.e., para, meta, and ortho. In the case at hand, one of these groups is an —OH and the other is an NH$_2$, or precisely the three aminophenol isomers 1-26, 1-27, and 1-28. All three permutations of the hexagonally determined departure vectors are opened up nicely here by the 'two gases' at once solution, since between the three 'gassed' products, 2-26, 2-27, and 2-28, we have one of each of the two new 'SuFExable' groups departing on either 60°, 120°, or 180° in plane from the benzene core (FIG. 3).

Figure 5:
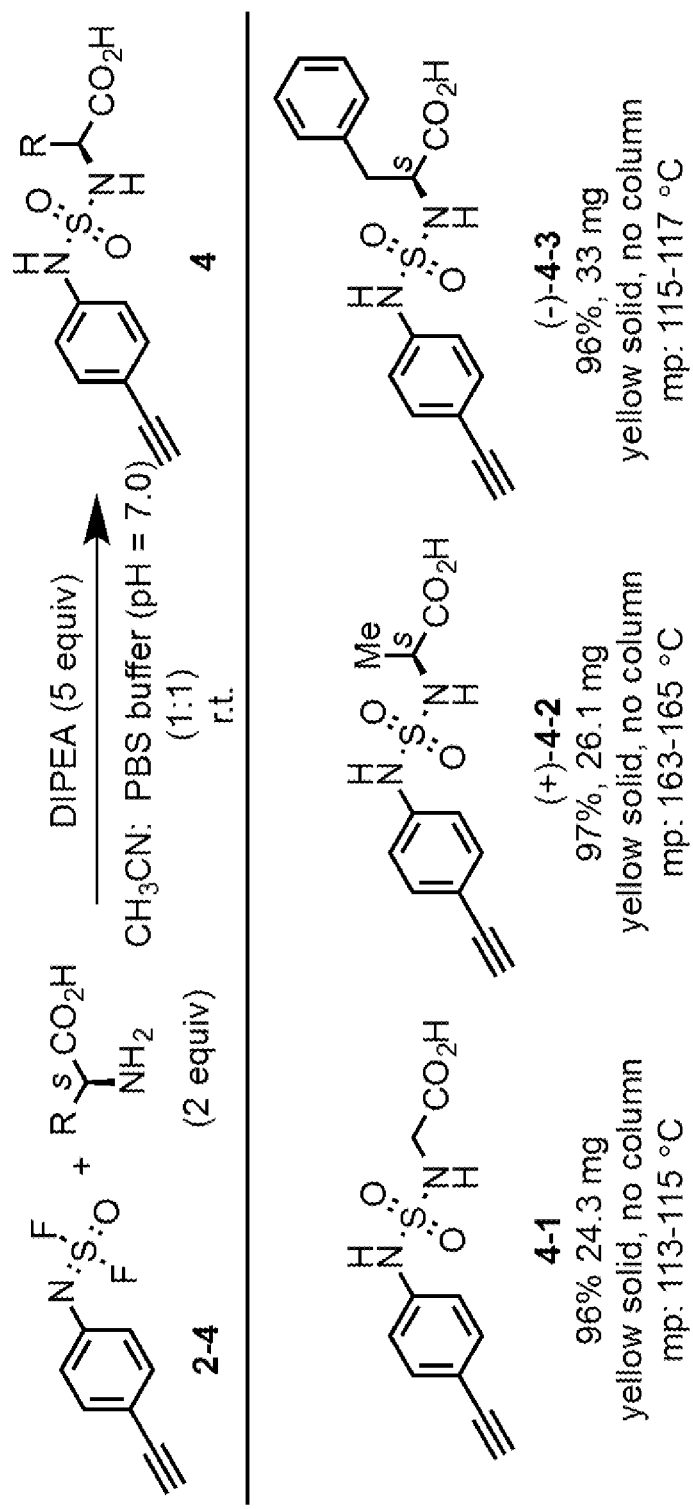
FIG. 5 illustrates the reaction of iminosulfur oxydifluorides with amino acids.

Second Dimension Connectivity: Iminosulfur Oxydifluorides with Amines or Amino Acids Cramer and Coffman surveyed the reactivity of Ph-N=SOF$_2$ with a selection of amines and found that weakly basic N-methylaniline gave no reaction; on the other hand, tert-butylamine could substitute two fluorines, while piperidine could substitute only one fluorine. The difluoride could also react with sodium ethoxide to form the ethyl phenylsulfamate. [Ref. 22]. As discussed in detail herein, a wider selection of amine nucleophiles (FIG. 4) can react with the iminosulfur oxydifluorides than has previously been reported. For example, the reaction with secondary amines proceeded smoothly: when 2 mol equiv of the given amine were added to a solution of the iminosulfur oxydifluorides (2) in acetonitrile at room temperature, the mono-substituted products (3) were formed in excellent yields, leaving a single unreacted fluoride in place. These impressively clean transformations required no further purification. [Ref. 24]. The reaction of the iminosulfur oxydifluorides (2-8) with a selection of amino acids proceeded equally well, albeit with concomitant hydrolytic loss of the second fluoride, giving the unsymmetrical sulfamide products (4-1 through 4-3) in excellent yields (FIG. 5).

Iminosulfur Oxydifluorides with Aryl Silyl Ethers

Figure 6:
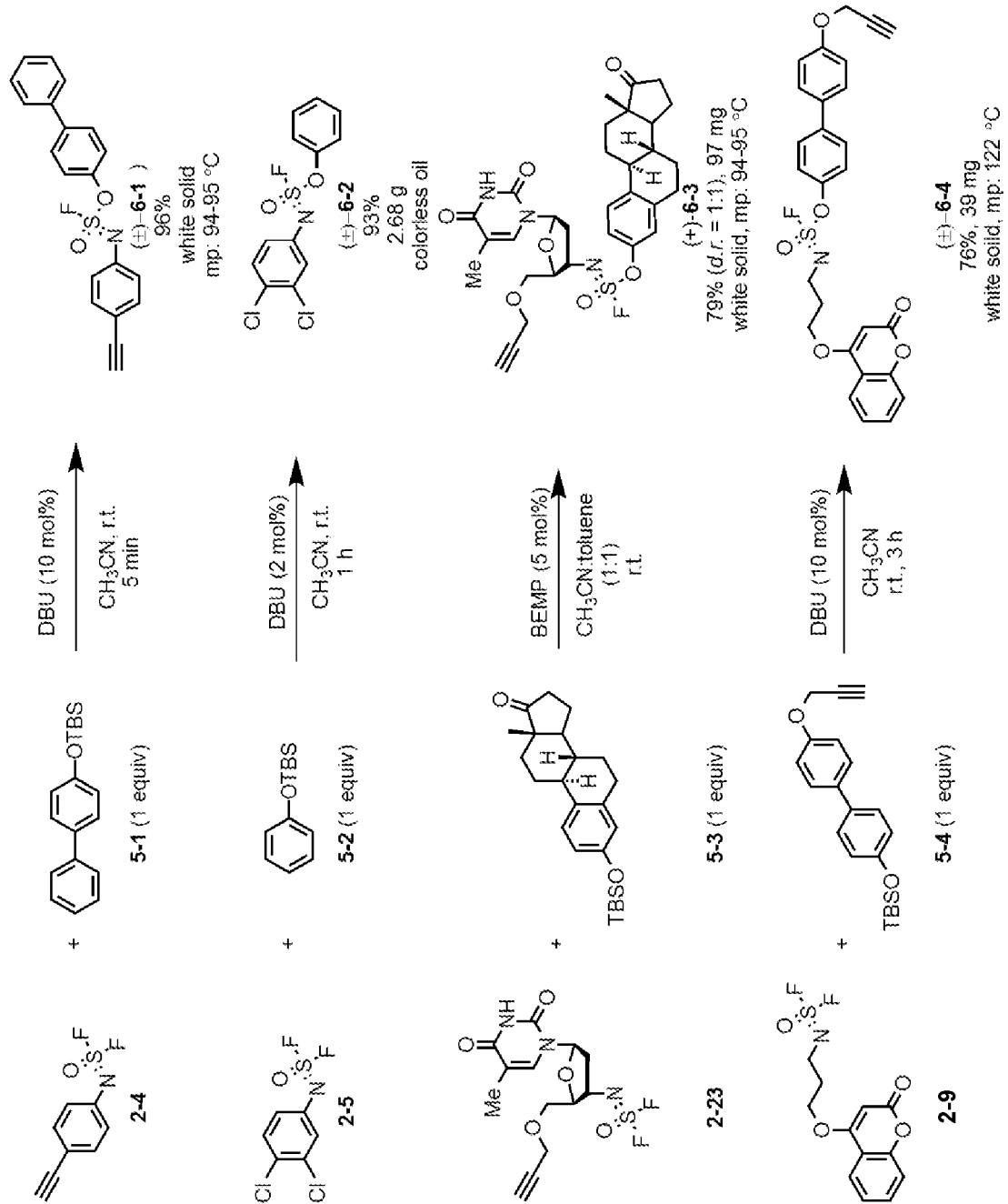
FIG. 6 illustrates connecting amines with phenols

In the spirit of Click Chemistry (i.e. the goal of creating stable and useful intermolecular linkages), the reaction of the iminosulfur oxydifluorides (2) with aryl silyl ethers (5) under DBU/BEMP activation was evaluated. In the presence of DBU (10 mol %) and 1 mol equiv of the respective aryl silyl ether (5), the SuFEx reactions of the iminosulfur oxydifluorides (2) reached completion within just 5 minutes, giving the corresponding sulfurofluoridoimidates (6) in excellent yield (FIG. 6). Reducing the catalyst loading to 2 mol % proved equally effective, resulting in similar yields of products on gram scale. Even the complex reactants: AZT derivative (2-23) and estrone (5-3) were readily connected.

Figure 7:
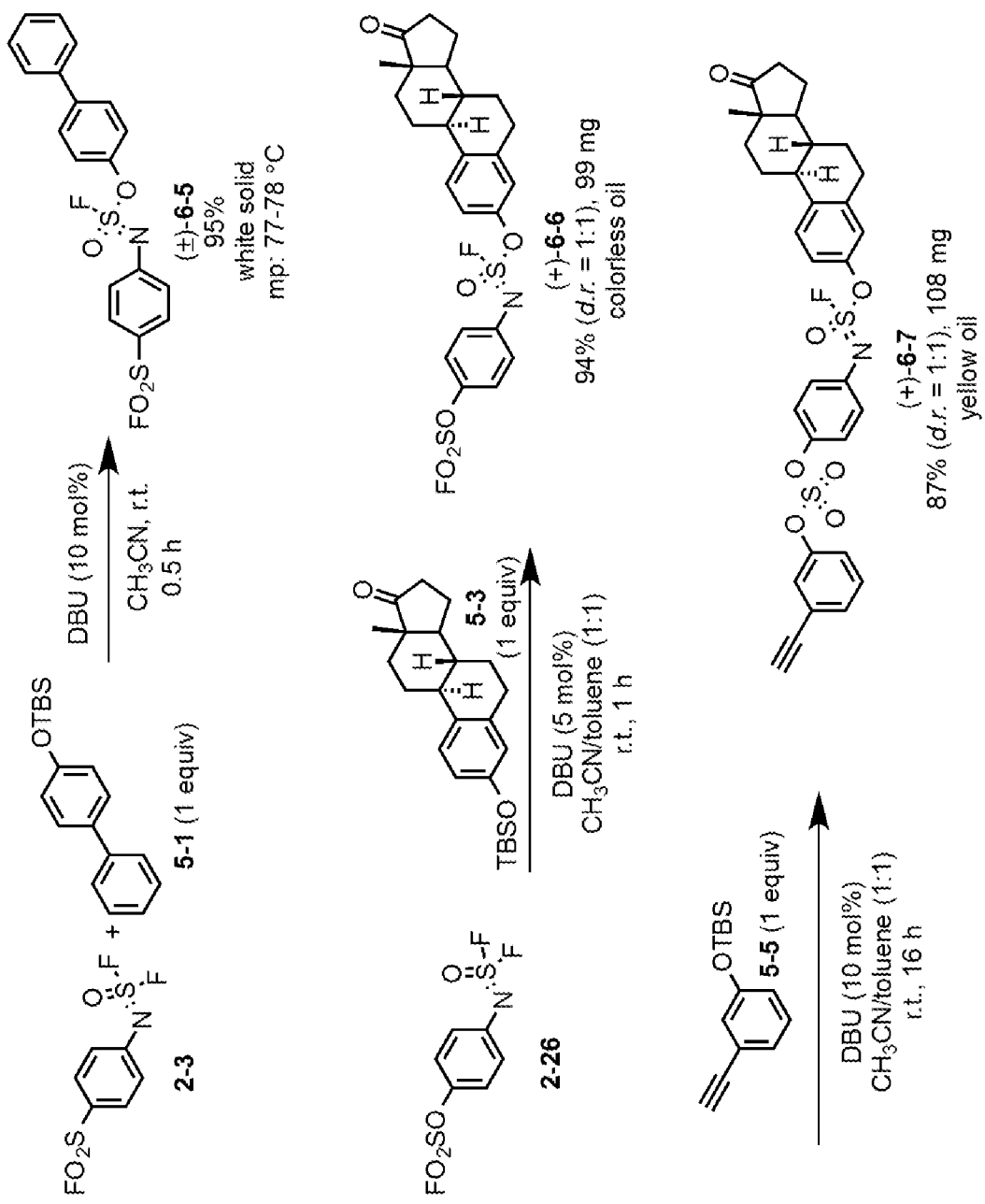
FIG. 7 shows a comparison of the reactivity of iminosulfur oxydifluoride with sulfonyl fluoride and fluorosulfate.

The exchange of just one S—F bond under typical SuFEx conditions revealed that the reactivity of the remaining S—F bond of the sulfurofluoridoimidate is significantly attenuated relative to the S—F bonds of the iminosulfur oxydifluoride. This is a welcome feature, particularly for instances when sequential SuFEx based modification are desirable. In order to further calibrate the relative reactivity profiles of the various S—F environments, a series of competition experiments were performed on substrates presenting two or more types of S—F functionality (FIG. 7). When the para-disubstituted benzene derivative 2-3, comprising both aryl sulfonyl fluoride (Ar—SO$_2$F) and aryl iminosulfur oxydifluoride groups (Ar—N=SOF$_2$), was treated with one equivalent of the aryl silyl ether 5-1 and DBU 10 mol % in acetonitrile, the SuFEx reaction occurred exclusively at the iminosulfur oxydifluoride center to give the corresponding product 6-5 in 95% yield—the sulfonyl fluoride (—SO$_2$F) group remained untouched (FIG. 7). Similarly, when the SuFEx reaction was performed with the analogous fluorosulfate (—OSO$_2$F) substrate 2-26 under modified conditions [DBU (5 mol %); CH$_3$CN:toluene (1:1)], the exchange again occurred exclusively at the iminosulfur oxydifluoride center to give the corresponding product 6-6 in 94% yield. When the sulfurofluoridoimidate 6-6 itself was exposed to the aryl silyl ether (5-5) in the presence of DBU (10 mol %) over 16 hours, SuFEx catalysis achieved linkage exchange at the fluorosulfate group, giving the mixed sulfate-sulfurofluoridoimidate linked product 6-7 (FIG. 7). From these experiments, the suggested order of reactivity of SO$_2$F$_2$ and O=SF$_4$ derived S—F bonds towards SuFEx reactions with aryl silyl ethers is: —N=SOF$_2$>—OSO$_2$F>—N=S(O)(OAr)F.

Third Dimension Connectivity: Amines and Aryl Silyl Ethers

Figure 8:
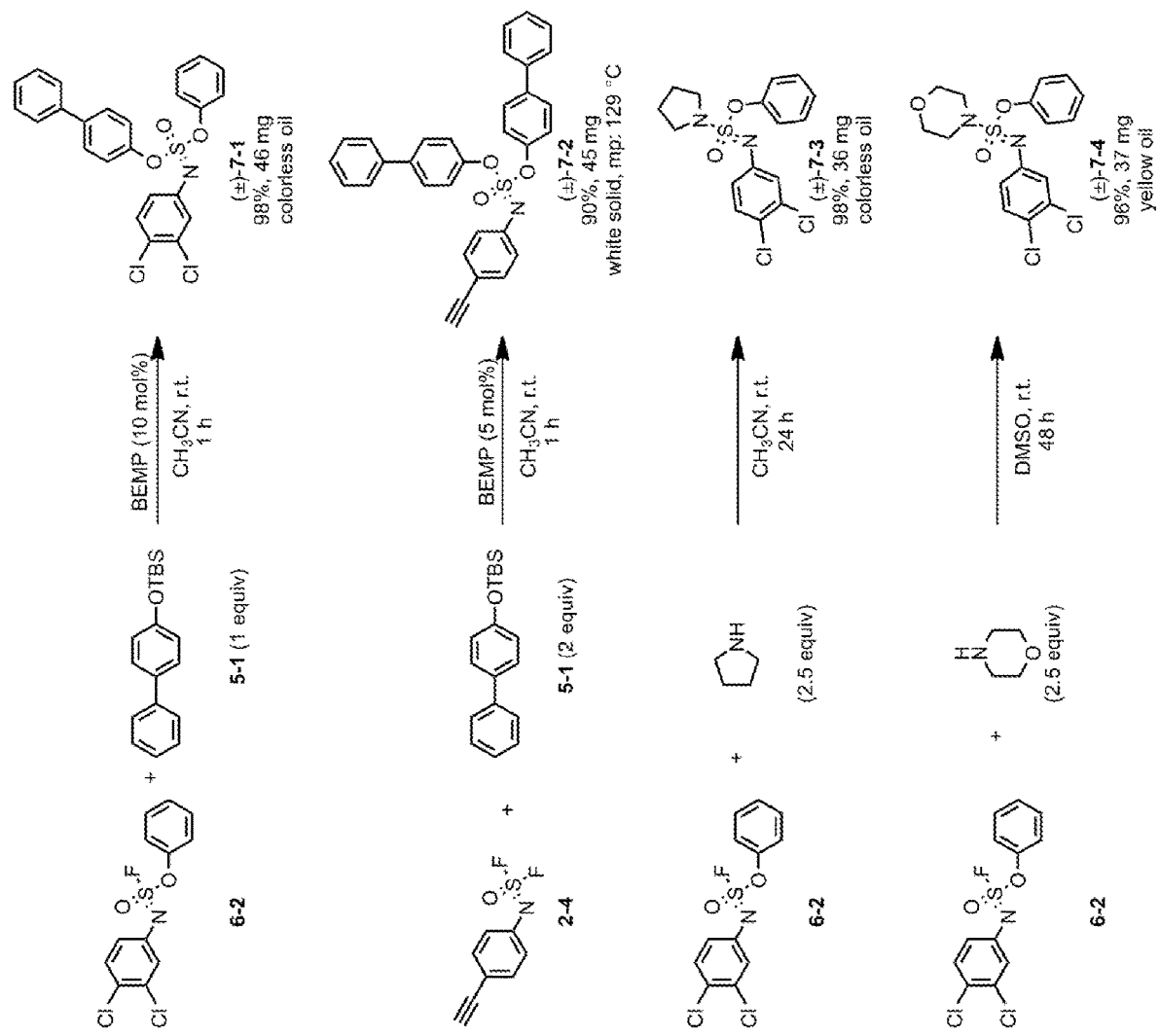
FIG. 8 shows the connections of primary amines with two phenols or one phenol and one secondary amine

Additional catalysts such as 2-tert-butylimino-2-diethylamino-1,3-dimethylperhydro-1,3,2-diazaphosphorine (BEMP) was evaluated for activating the remaining S$^{VI}$—F bond of the corresponding sulfurofluoridoimidates (6). Indeed, the treatment of 6-2 with the aryl silyl ether 5-1 in the presence of 10 mol % BEMP (CH$_3$CN, r.t., 1 h), gave the corresponding sulfurimidate 7-1 in almost quantitative yield. BEMP proved equally efficient at lower concentrations (5 mol %), and even two phenol linkages could be installed in one pot without compromising yield (7-2). Interestingly, secondary amines alone react directly with 6-2, producing 7-3, 7-4 in excellent yields (FIG. 8).

Figure 9:
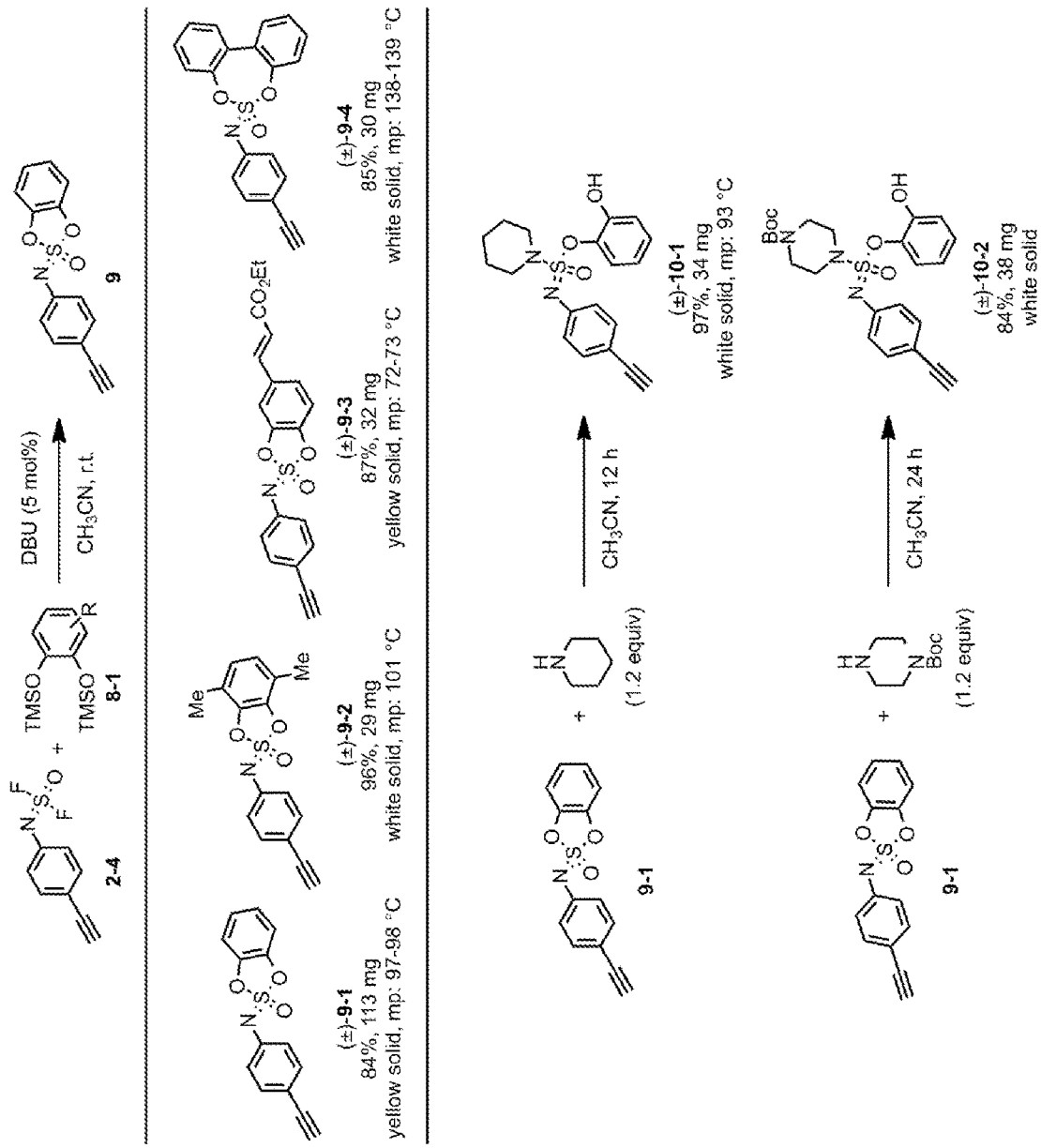
FIG. 9 illustrates the reaction of iminosulfur oxydifluorides with catechols and the activity of the product towards amines.

Another manifestation of the third dimension of SuFEx plugin-reactions from O=SF$_4$ derived hubs is the direct reaction of phenyliminosulfur oxydifluorides (2-4) with TMS-protected catechols (FIG. 9). The entrained inter- and intramolecular SuFEx reactions proceeded smoothly with DBU (5 mol %), to form the four (9-1 through 9-4) iminooxy cyclic catechol sulfuryl derivatives in excellent yields (FIG. 9). Of particular significance, the imino cyclic catecholate 9-1 is readily ring opened by piperidine and Boc-piperazine to give the corresponding amino sulfonimidate products 10-1 and 10-2 in excellent yields.

Figure 10:
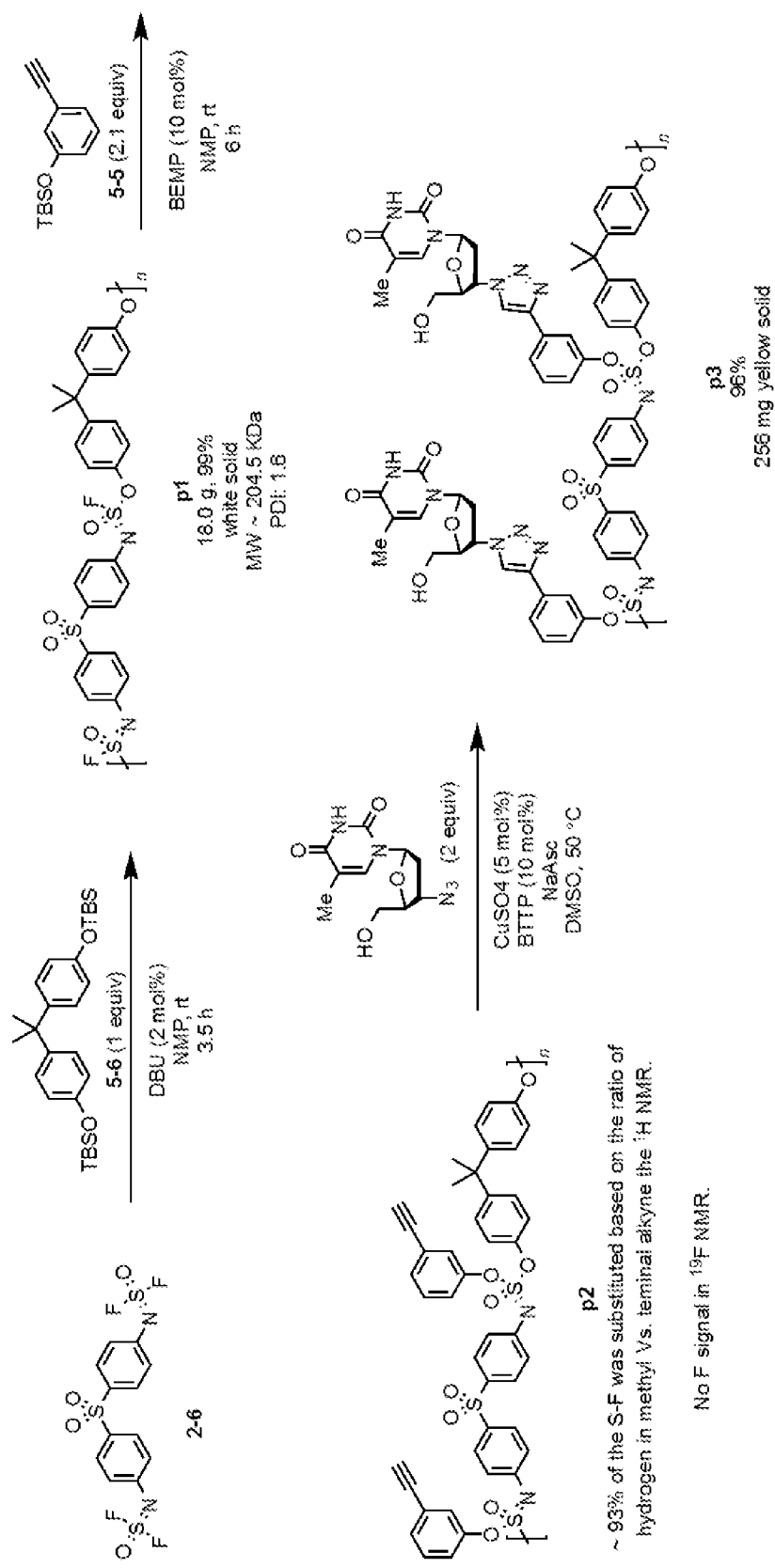
FIG. 10 illustrates polymer synthesis based on the iminosulfur oxydifluoride.

The application of the SuFEx Click Chemistry in the efficient synthesis of polysulfates through the linking of fluorosulfates and silyl ethers. [Ref. 11]. A priori, the bis(aryl iminosulfur oxydifluoride) 2-6 and the bis(aryl silyl ether) 5-6 appeared perfectly setup for the polymer synthesis. Indeed, therein A-A/B-B style polymerization proceeded smoothly under a SuFEx conditions (DBU 2 mol %), producing a polymer with a molecular weight of 204 KDa and PDI as low as 1.6 (FIG. 10). Expanding the scope of this core polymer p1, branching was readily achieved by the second dimensional SuFEx reaction of the remaining S$^{VI}$—F bond with the alkynylaryl silyl ether (5-5). The efficiency of the reaction was demonstrated with an impressive substitution rate of approximately 93% based on the ratio of methyl vs. terminal alkynyl protons in $^1$H NMR. In a final demonstration of the power of combined Click Chemistry, the alkyne decorated SuFEx polymer was reacted with the AZT (11) under the ligand-accelerated CuAAC conditions [Ref. 25] to give the nucleoside decorated polymer p3 in excellent yield. NMR analysis showed that all alkyne groups in the parent polymer were converted into the corresponding triazoles.

In summary, O=SF$_4$ gas provides a new SuFEx connector that reacts efficiently with primary amines to form reactive iminosulfur oxydifluoride derivatives. These derivatives provide S—F groups that are reactive toward amino and silyl ether compounds to provide a variety of useful molecules.

In another aspect, the versatility and power of the SOF$_4$ derived iminosulfur oxydifluorides can be utilized to prepare linear polymers comprising —N=S(O)(F)— groups in the polymer backbone, which can be selectively reacted to form a branched polymer.

A method of preparing an iminosulfur oxyfluoride polymer comprises contacting a bis-(iminosulfur oxydifluoride) monomer with a bis-(silyl ether) monomer in the presence of a catalyst to for the iminosulfur oxyfluoride polymer. The catalyst is selected from an amidine base, a guanidine base, a phosphorine base, and a fluorine-containing anion (e.g., fluoride or an HF-fluoride, such as bifluoride).

In some method embodiments, the bis(iminosulfur oxydifluoride) monomer can be. e.g., a compound of Formula (III):

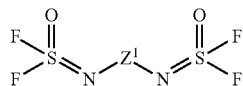

wherein $Z^1$ is a divalent organic group.

Additionally, the bis-(silyl ether) can be, e.g., a compound of Formula (IV):

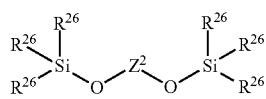

wherein $Z^2$ is a divalent organic group; and each $R^{26}$ independently is an alkyl group, an aryl group, an arylalkyl group or an alkylaryl group.

In some method embodiments, the iminosulfur oxyfluoride polymer produced by the method can a compound of Formula (V):

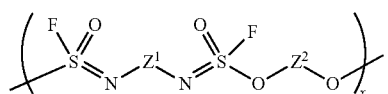

wherein x is the average number of repeating units in the polymer, and has a value of greater than 1, e.g., greater than 10, greater than 20, greater than 30, greater than 50, greater than 100, greater than 1000; or greater than 10,000; and each of $Z^1$ and $Z^2$ independently is a divalent organic group.

In another aspect, iminosulfur oxyfluoride polymer is provided, which comprises a polymer of Formula (V):

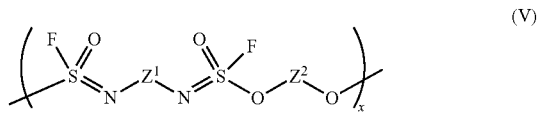

wherein x is the average number of repeating units in the polymer, and has a value of greater than 1, e.g., greater than 10, greater than 20, greater than 30, greater than 50, greater than 100, greater than 1000; or greater than 10,000; and each of $Z^1$ and $Z^2$ independently is a divalent organic group.

In some embodiments, $Z^1$ and/or $Z^2$ of the monomer and/or polymer is a divalent organic group of Formula (VI):

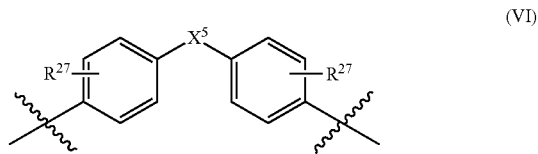

in which $X^5$ is selected from —CH$_2$—, —CH(R$^{28}$)—, —C(R$^{28}$)$_2$—, —O—, —S—, and —SO$_2$—; each $R^{27}$ independently is a substituent, which can be selected, for example, from a halogen (e.g., Cl, Br, I), an alkyl, an alkoxy, an aryl, an alkylaryl, an arylalkyl, and a heteroatom-containing substituent comprising one or more oxygen, nitrogen, or sulfur atoms, optionally in combination with carbon and hydrogen (e.g., acyl, acyloxy, amido, and the like). $R^{28}$ preferably is selected from alkyl, aryl, arylalkyl, and alkylaryl. The subscript y is 0, 1, 2, 3, or 4.

In some exemplary embodiments, $Z^1$ and/or $Z^2$ of the polymers/or and monomers independently are divalent groups of Formula (VII):

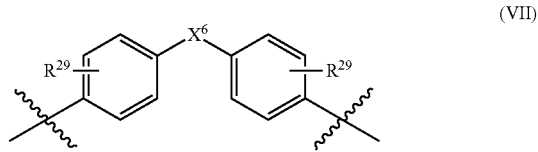

wherein each $R^{29}$ independently is a hydrocarbyl group, and $X^6$ is a covalent bond, —C(CH$_3$)$_2$—, —C(CF$_3$)$_2$—, or —SO$_2$—.

Preferably, the monomers are reacted in approximately equimolar amounts or with an excess (e.g., 0.01 up to about 10 mol % excess) of one monomer (e.g., the fluorinated monomer). The monomers can be contacted with one another in neat (solventless or bulk) form, or in a solvent (e.g., a halogenated hydrocarbon, acetonitrile, pyridine, N-methylpyrrolidone, and the like), a combination of solvents (e.g., together or sequentially added), or a combination of solventless and solvent conditions (e.g., sequentially). Typically, the polymerization is performed at a temperature in the range of about 20 to about 200° C. for about 0.5 to about 48 hours. Additionally, the reaction conditions and monomers are surprisingly tolerant of a large variety of organic moieties and substituents. This translates into an unprecedented freedom of selection of monomer components, including monomers with groups that are known to interfere with normal acid-base reactions, and the ability to tailor the functionality of the resulting polymer to a very high degree.

In any of the reactions and products described herein (e.g., in Embodiments 1 through 60, above), including reactions and products involving or comprising discrete small molecules and polymers, each of the organic groups or moieties independently can be selected from the group consisting of consisting of a hydrocarbon group, alkyl, aryl, alkylaryl, arylalkyl, a steroid, a terpene, a terpenoid, an alkene, an alkyne, a heterocycle, an alkenyl-substituted aryl, an alkynyl-substituted aryl, a carbohydrate, a polymer, an amino acid, a polypeptide, a nucleotide, a nucleic acid, an enzyme, —CH($R^2$)—C(=O)OH (wherein $R^2$ is H or a second organic moiety), a nucleoside moiety, and a combination of two or more thereof. Additionally, the organic groups and moieties can be substituted with one or more functional group. Non-limiting examples of such functional groups include e.g., hydroxyl, halogen, nitro, —C(O)$R^{30}$, —C(O)O$R^{30}$, —C(O)N($R^{30}$)$_2$, —CN, —SO$_v$$R^{30}$, —SO$_v$N($R^{30}$)$_2$, $R^{30}$SO$_v$N($R^{30}$)—, —N($R^{30}$)SO$_v$$R^{30}$, —SO$_3$$R^{30}$, —N($R^{30}$)$_2$, —N($R^{30}$)O$R^{30}$, —N($R^{30}$)C(O)$R^{30}$, —N($R^{30}$)C(O)O$R^{30}$, —N($R^{30}$)C(O)N($R^{30}$)$_2$, —OC(O)N($R^{30}$)$_2$, —OC(O)O$R^{30}$, azido, alkyl, cycloalkyl, alkenyl, alkynyl, alkoxy, fluoroalkyl, fluoroalkoxy, aryl, aryloxy, heteroaryl, poly(ethyleneoxy), alkynyl-terminated poly(ethyleneoxy), a fatty acid, a carbohydrate, an amino acid, a polypeptide; wherein each $R^{30}$ independently is H, alkyl, or aryl, and v is 0, 1, or 2.

The term "hydrocarbon" and grammatical variations thereof is well known in the art and refers to an organic compound consisting entirely of hydrogen and carbon. Hydrocarbons can be saturated (contain no multiple bonds), unsaturated (containing at least one double or triple bond, or aromatic (containing an aromatic ring system such as a benzene ring, or a condensed aromatic ring system such as a naphthalene, anthracene, and similar systems). Hydrocarbons can include linear chains of carbons atoms, branched chains of carbon atoms, rings of carbon atoms, or any combination thereof. Non-limiting examples of hydrocarbons include alkanes, alkenes, alkynes, aromatic (aryl) compounds, aromatic compounds substituted by an alkyl alkenyl, or alkynyl group), cycloalkanes, cycloalkenes, terpenes, and the like. Unless otherwise specified, a hydrocarbon group can be attached to any of the compounds and polymers of Embodiments 1 through 22 and 45 through 59 at any position on the hydrocarbon structure, e.g., by replacement of a hydrogen atom The term "hydrocarbyl" and grammatical variations thereof refers to univalent groups formed by removing a hydrogen atom from a hydrocarbon, e.g. ethyl, phenyl, phenylmethyl, methylphenyl, ethynylphenyl, propargyl, or any other hydrocarbon group lacking a hydrogen atom thereof, and the like.

The term "carbohydrate" and grammatical variations thereof is well known in the art refers to, for example, polyhydroxylated compounds that formally have an empirical elemental formula (CH$_2$O)w in which w is >1. Non-limiting examples of carbohydrates include sugars (e.g., glucose, maltose), polysaccharides (e.g., starches, cellulose), and modified versions of sugars and polysaccharides (e.g., comprising one or more functional group in place of or in addition to hydroxyl groups, such as amino, ethers, esters), as well as deoxy sugars and deoxy polysaccharides (i.e., sugars and polysaccharides in which an OH has been replaced by an H), and the like. The carbohydrates can be naturally occurring materials, synthetic materials, or a combination thereof. Unless otherwise specified, a carbohydrate group can be attached to any of the compounds and polymers of Embodiments 1 through 22 and 45 through 59 at any position on the carbohydrate structure, e.g., by replacement of a hydrogen atom or heteroatom.

The term "amino acid" and grammatical variations thereof is well known in the art and refers to, for example, organic compounds comprising at least one amino group, and at least one carboxylic acid group. Examples of amino acids include natural or synthetic alpha-amino acids (e.g., the common proteogenic amino acids, as well as non-proteogenic amino acids such as ornithine, which can be chiral materials, e.g., levo or dextro stereoisomers, or mixtures thereof, or achiral materials, depending on the structure), as well as compounds in which the amino group and carboxylic acid group are separated by more than one carbon. Unless otherwise specified, an amino acid group can be attached to any of the compounds and polymers of Embodiments 1 through 22 and 45 through 59 at any position on the amino acid structure, e.g., by replacement of a hydrogen atom or heteroatom.

The term "polypeptide" and grammatical variations thereof is well known in the art and refers to, e.g., materials including two or more amino acids (generally alpha-amino acids) joined together by peptide (amide) bonds between the carboxylic acid group (typically an alpha-carboxylic acid group) of one amino acid and the amino group (typically the alpha-amino group) of another amino acid. As used herein, the term polypeptide also encompasses proteins, as well as materials having a polypeptide core structure with additional functional or protecting groups appended to the polypeptide backbone. The term "peptide analog" and grammatical variations thereof refers to polypeptide-like materials in which one or more peptide bond is replaced by a non-peptide linkage, such as an ester, an ether, and the like. Unless otherwise specified, a polypeptide group can be attached to any of the compounds and polymers of Embodiments 1 through 22 and 45 through 59 at any position on the polypeptide structure, e.g., by replacement of a hydrogen atom or heteroatom.

The term "steroid", as used herein, refers to any of a large group of substances that have in common a ring system based on a 1,2-cyclopentanoperhydrophenanthrene, and includes, for example, natural bile acids, corticosteroids, sex hormones, plant steroids, and sterols, as well as synthetic derivatives thereof. Unless otherwise specified, a steroid group can be attached to any of the compounds and polymers of Embodiments 1 through 22 and 45 through 59 at any position on the steroid structure, e.g., by replacement of a hydrogen atom or heteroatom.

The term "terpene", as used herein, refers to any member of a class of hydrocarbons occurring particularly in essential oils, and composed of multiple isoprene units, and may be acyclic, cyclic, or multicyclic, as well as saturated or unsaturated. Unless otherwise specified, a terpene group can be attached to any of the compounds and polymers of Embodiments 1 through 22 and 45 through 59 at any position on the terpene structure, e.g., by replacement of a hydrogen atom or heteroatom.

The term "terpenoid", as used herein, refers to a terpene that includes an oxygenated functional group (e.g., ketone, aldehyde, hydroxyl, carboxyl, group). Unless otherwise specified, a terpenoid group can be attached to any of the compounds and polymers of Embodiments 1 through 22 and 45 through 59 at any position on the terpenoid structure, e.g., by replacement of a hydrogen atom or heteroatom.

As used herein, the term "nucleoside", which is well known in the art, refers generally to a purine or pyrimidine base linked to C-1 of a beta-D-ribofuranose or 2-deoxy-beta-D-ribofuranose through a nitrogen atom of the pyrimidine (at N-1) or purine (at N-9) base. Unless otherwise specified, a nucleoside group can be attached to any of the compounds and polymers of Embodiments 1 through 22 and 45 through 59 at any position on the nucleoside structure, e.g., by replacement of a hydrogen atom or heteroatom. In some cases, the nucleoside is a group set forth in Embodiment 2, above.

As used herein, the term "nucleotide", which is well known in the art, refers generally to a nucleoside that is phosphorylated by an orthophosphate of oligophosphate at any of the hydroxyl groups of the sugar portion of the molecule. Typically the phosphate group is at either the 3' or 5' hydroxyl group of the sugard portion of the molecule. Unless otherwise specified, a nucleotide group can be attached to any of the compounds and polymers of Embodiments 1 through 22 and 45 through 59 at any position on the nucleotide structure, e.g., by replacement of a hydrogen atom or heteroatom. In some cases, the nucleotide is a phosphorylated version of a group set forth in Embodiment 2, above.

As used herein, the term "nucleic acid", which is well known in the art, refers generally to a single or double stranded polynucleotide comprising multiple nucleotides bound together through phosphodiester linkages, generally between the 5' hydroxyl of one nucleotide unit and the 3' hydroxyl group of an adjacent nucleotide forming a generally linear chain of nucleotide units, as is well known in the art. Unless otherwise specified, a nucleic acid group can be attached to any of the compounds and polymers of Embodiments 1 through 22 and 45 through 59 at any position on the nucleic acid structure, e.g., by replacement of a hydrogen atom or heteroatom.

The term "effector group" refers to a chemical gent that can perform a particular chemical or biochemical function, such as, e.g., antimicrobial agents and catalysts such as enzymes. Polymer bound antimicrobial agents are useful as microbe-resistant polymer films or articles, e.g., for marine use, medical use, or use as a sanitary surface for food preparation, pharmaceutical packaging, and the like. Polymer bound enzymes (also known as immobilized enzymes) are useful as catalysts in laboratory and industrial processes, including in some cases, aqueous or nonaqueous processes. For example, immobilized enzymes have been used in the production of high-fructose corn syrup, pectin hydrolysis, debittering of fruit juices, interesterifications of food, fats, and oils, biodiesel production, carbon dioxide capture, and numerous other applications. Unless otherwise specified, an effector group can be attached to any of the compounds and polymers of Embodiments 1 through 22 and 45 through 59 at any position on the effector group structure, e.g., by replacement of a hydrogen atom or heteroatom.

Polymers suitable for use as substituents in the compounds and methods of any of Embodiments 1 to 44 described above include any polymeric structure. In some embodiments, the polymer is a polystyrene, a polyamide, a polycarbonate, a polyurethane, and the like. In some embodiments the polymer is an amino-substituted polymer comprising primary amino groups in which one or more of the primary amino groups has been reacted with thionyl tetrafluoride as described herein to form an iminosulfur oxydifluoride group from the primary amino group. Non-limiting examples of some primary amino-substituted polymers include amino-substituted polystyrene, polylysine, amino-substituted polyethylene copolymers, amino-substituted polyethers, polyallylamine and copolymers thereof (e.g., acryamide-allylamine copolymers, N-vinylpyrrolidone-allylamine copolymers, acrylamide-allylamine copolymers, and the like), branched polyethyleneimines, and the like.

In any of Embodiments 1 through 60 or any other compounds, polymers, and methods described herein, the organic groups of the compounds and polymers can be bound by direct linkage of the components of the compounds and polymers or can be bound through an intercalated link of differing length (also known as a spacer), e.g., by a hydrocarbon-based linker, such as an alkylene group, an aryl group, and the like, by a heteroatom (i.e., a non-carbon atom), or other functional groups.

Molecular weight values of polymers, such as number average molecular weight ($M_n$) and weight average molecular weight ($M_w$), as well as polydispersity index values ("PDI", i.e., $M_w/M_n$) used herein are based on gel permeation chromatography (GPC) versus polystyrene standards. Molecular weight parameters for which there is no explicit description or contextual implication of being GPC values should be interpreted as GPC-derived values. The molecular weight values are reported in units of g/mol (also referred to as Daltons, "Da") or Kg/mol (also referred to as kDa).

As described herein, the monomers and other reactant compounds can be contacted with one another neat or in a solvent. Non-limiting examples of suitable solvents include a halogenated hydrocarbons (e.g., dichloromethane, chloroform, carbon tetrachloride, perchloroethane, chlorofluorocarbons, fluorocarbons, and the like), ethers (e.g., diethyl ether, tetrahydrofuran, dimethoxyethane, and the like), esters (e.g., ethyl acetate), nitriles (e.g., acetonitrile, and the like), ketones (e.g., acetone, methylethylketone), pyridines (e.g., pyridine, picolines, and the like), amides (e.g., N-methylpyrrolidone, acetamide, dimethylacetamide, and the like), sulfoxides (e.g., dimethylsulfoxide, and the like), and sulfones (e.g., sulfolane, dimethylsulfone, and the like). Preferably, the solvent is non-aqueous and aprotic. If desired, mixed solvent systems can be used, or the polymerization reaction can be performed sequentially in different solvents or in a combination of solventless and solution conditions (e.g., beginning in one solvent (or solventless) and completing the polymerization in another solvent).

In some embodiments, the catalyst used in reactions of an S—F compound with a silyl ether or silyl amine, such as the polymerization and discrete, small molecule reactions described above, comprises at least one material selected from the group consisting of an amidine, a guanidine, a phosphazene, a nitrogen-heterocyclic (N-heterocyclic) carbene, a tertiary alkoxide, and a fluoride salt. For example, the basic catalyst can comprise an amidine base (e.g., 1,8-diazabicyclo[5.4.0]undec-7-ene (DBU), and the like), a guanidine (e.g., 1,1,3,3-tetramethylguanidine (TMG), 1,5,7-triazabicyclo[4.4.0]dec-5-ene (TBD), and 7-methyl-1,5,7-triazabicyclo-[4.4.0]dec-5-ene (MTBD) and the like), a phosphazene base (e.g., 2-tert-butylimino-2-diethylamino-1,3-dimethylperhydro-1,3,2-diazaphosphorine (BEMP), 1-tert-butyl-4,4,4-tris-(dimethylamino)-2,2-bis[tris(dimethylamino)-phosphoranylidenamino]-2$\lambda^5$,4$\lambda^5$-catenadi(phosphazene) (P$_4$-t-Bu), and the like), a nitrogen-heterocyclic carbene (e.g., an imidazole-2-ylidene, a 1,2,4-triazole-5-ylidene, a thiazole-2-ylidene, an imidazolin-2-ylidene, and the like), a tertiary alkoxide (e.g., potassium tert-butoxide and the like), or a fluoride-containing salt (e.g., CsF, CsFHF, KF, tetrabutylammonium fluoride (TBAF), tris(dimethylamino)sulfonium-difluorotrimethylsilicate (TASF), and the like), or a combination of two or more thereof. Preferably, the base comprises an amidine, a phosphazene, or both. If desired, a combination of catalysts can be added as a mixture or sequentially.

In some embodiments, the catalyst for reaction of an S—F compound and a silyl ether or silyl amine comprises an HF-fluoride salt of formula $(R^+)(F(HF)_w^-)$, wherein $R^+$ is an organic cation or a chelated metal cation, and w is 1 or greater. As used herein, "organic cation" refers to cationic species comprising one of more organic (carbon-hydrogen-based) moiety bound to a positively charged heteroatom, such as S, N, or P, and includes various onium cations such as quaternary ammonium cations, organosulfonium cations (e.g., sulfonium cations comprising three groups, such as alkyl, aryl aminoalkyl, and/or aminoaryl groups, bound to a positively charged S, such as tris(dialkylamino)sulfonium), organophosphonium cations (e.g., phosphonium cations comprising four groups, such as alkyl, aryl, aminoalkyl, aminoaryl and/or other substituent groups bound to a positively charged P), quaternized nitrogen heterocyclic cations (e.g., nitrogen heteroaromatic compounds comprising at least one positively charged nitrogen in the heteroaromatic ring, such as imidazolium cations in which both nitrogen atoms in an imidazole ring are alkylated), as well as cationic polymers, including both insoluble and soluble polymers (e.g., cationic polystyrene beads with appended quaternary ammonium groups). Chelated metal cations preferably comprise a monovalent metal ion (e.g., an alkali metal such as potassium and the like, or a monovalent transition metal, etc.) complexed with a chelating ligand, preferably a neutral (non-charged) ligand such as a crown ether (e.g., 18-crown-6, 12-crown-4, 15-crown-5, dibenzo-18-crown-6, and the like) and/or an azacrown ether (e.g., diaza-18-crown-6, and the like).

As used herein, "HF-fluoride" refers to anions comprising a fluoride anion bound to one of more hydrogen fluoride molecules, e.g., in a chain such as bifluoride ion (FHF$^-$), and having the general formula $F(HF)_w^-$, where n is 1 or greater, with w generally being in the range of 1 to 10 (e.g., w is in the range of 1 to 2, 1 to 3, 1 to 4, 1, to 5, 1 to 6, etc.). When w is 1, the HF-fluoride ion is bifluoride, when w is greater than 1, the HF-fluoride is a polyHF fluoride.

In some embodiments, the HF-fluoride catalyst comprises an organosulfonium bifluoride or polyHF fluoride such as tris(dialkylamino)sulfonium bifluoride salt of formula: $(R^a_2N)_3S^+(FHF)^-$ wherein each $R^a$ independently is an alkyl group comprising 1 to 20 carbon atoms, or two $R^a$ groups together comprise a 4 or 5 carbon alkylidene group (e.g., —CH$_2$—CR$^x_2$—CH$_2$—, or —CH$_2$CR$^x_2$CR$^x_2$CH$_2$— wherein each $R^x$ independently is H or alkyl) thereby forming a 5 or 6 membered ring with the N atom attached thereto; each $R^a$ alkyl or alkylidene group includes at least two hydrogen atoms on a carbon atom adjacent to the sulfur atom thereof, and each $R^a$ independently can be linear or branched; or a polyHF fluoride analog thereof. The tris(dialkylamino)sulfonium bifluoride salt can be prepared, e.g., by the methods described in U.S. Pat. No. 4,598,161 to Farnham et al., which is incorporated herein by reference in its entirety.

Tris(dialkylamino)sulfonium bifluoride salts have been reported to catalyze a living addition polymerization of olefinic monomers, such as methyl methacrylate, but heretofore have not been described as catalysts for condensation-type polymerizations (i.e., polymerizations in which a neutral molecule is produced from end groups of the monomers during formation of the polymer chain), particularly silyl and fluoro containing monomers, as in the methods described herein.

In other embodiments, the catalyst can be an organophosphonium bifluoride or polyHF fluoride, such as tetrabutylphosphonium bifluoride or polyHF fluoride, (Ph$_3$P—N=PPh$_3^+$) bifluoride or polyHF fluoride, and the like.

In other embodiments, the catalyst can be a quaternary ammonium bifluoride or polyHF fluoride, such as tetrabutylammonium bifluoride or polyHF fluoride, tetraethylammonium bifluoride or polyHF fluoride, and the like.

In other embodiments, the catalyst can be a quaternized heteroaromatic bifluoride or polyHF fluoride, such as an imidazolium bifluoride or polyHF fluoride (e.g., N,N-dimethylimidazolium bifluoride, N,N-di(isopropyl)imidazolium bifluoride, and the like).

In some other embodiments, the catalyst can be a polymer supported bifluoride or polyHF fluoride, such as a quaternary amino-substituted polystyrene bifluoride or polyHF fluoride.

In yet other embodiments, the catalyst can be a chelated metal bifluoride or polyHF fluoride, such as potassium 18-crown-6, and the like.

Bifluoride salts can be prepared by reaction of corresponding onium halide salts (e.g., Cl or Br) with silver(I) bifluoride (AgHF$_2$); see, Vergote et al., *Chem. Eur. J.* 2012, 18, p. 793-798). Alternatively, the catalysts can be prepared by the reaction of corresponding onium halide salts (e.g., Cl or Br) with anhydrous HF; see, (1) Matsumoto et al., *Solid State Sci.* 2002, 4, 23-26; (2) Hagiwara et al., *J. Fluorine Chem.* 1999, p. 1-3.

The poly-HF bonded onium catalysts can be obtained via the reaction of corresponding onium halide salts with anhydrous HF, as well; for selected examples, see, (1) Momota et al., *Electrochim Acta.* 1993, 38, p. 619-624; (2) Rozhkov et al. *Tetrahedron* 1975, 31, p. 977-981; (3) Ballinger et al., *Electrochim Acta.* 1985, 30, 1075-1077; and references therein.

Figure 11:
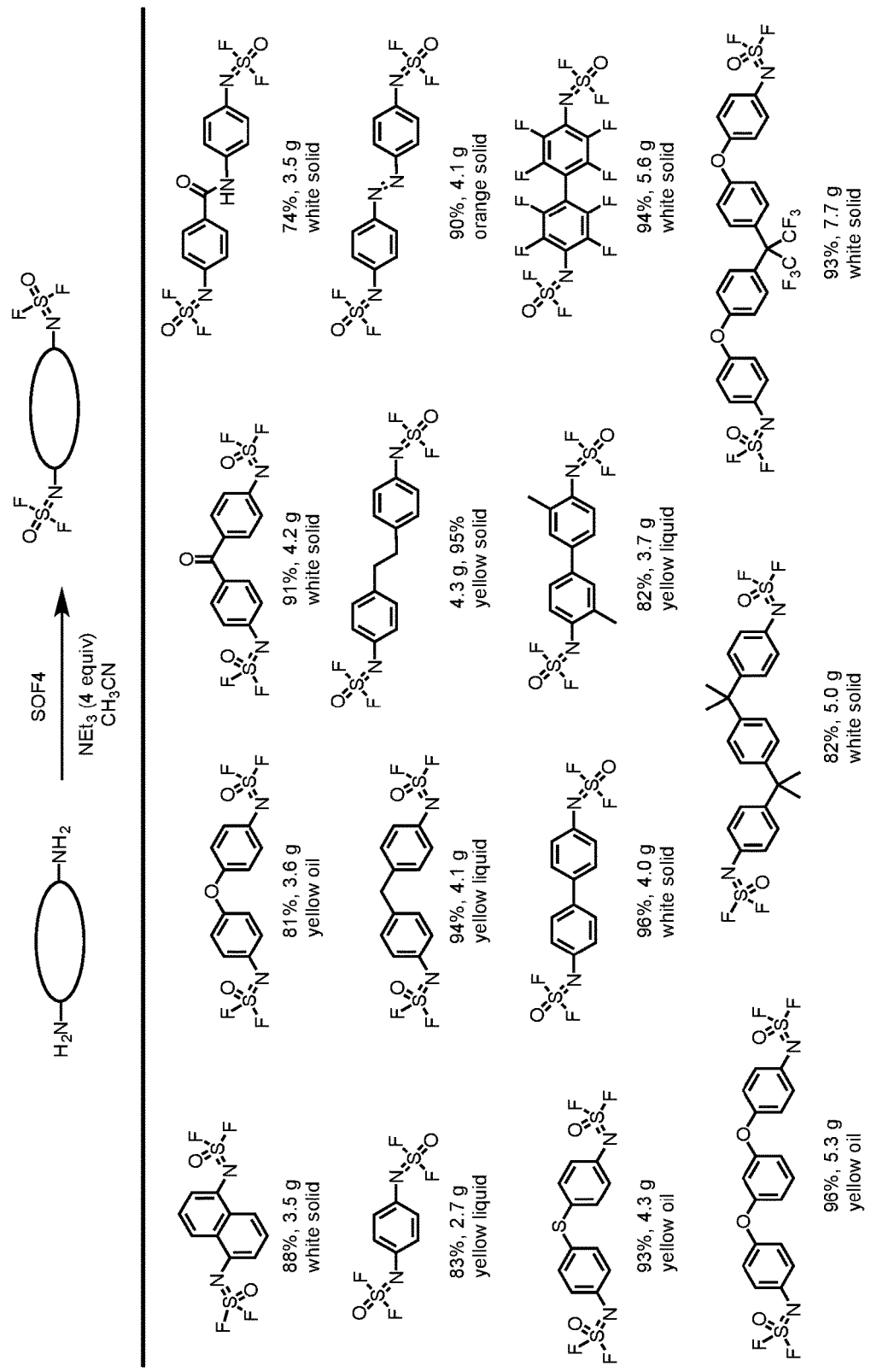
FIG. 11 illustrates reactions of $SOF_4$ based polymers.
Figure 12A:
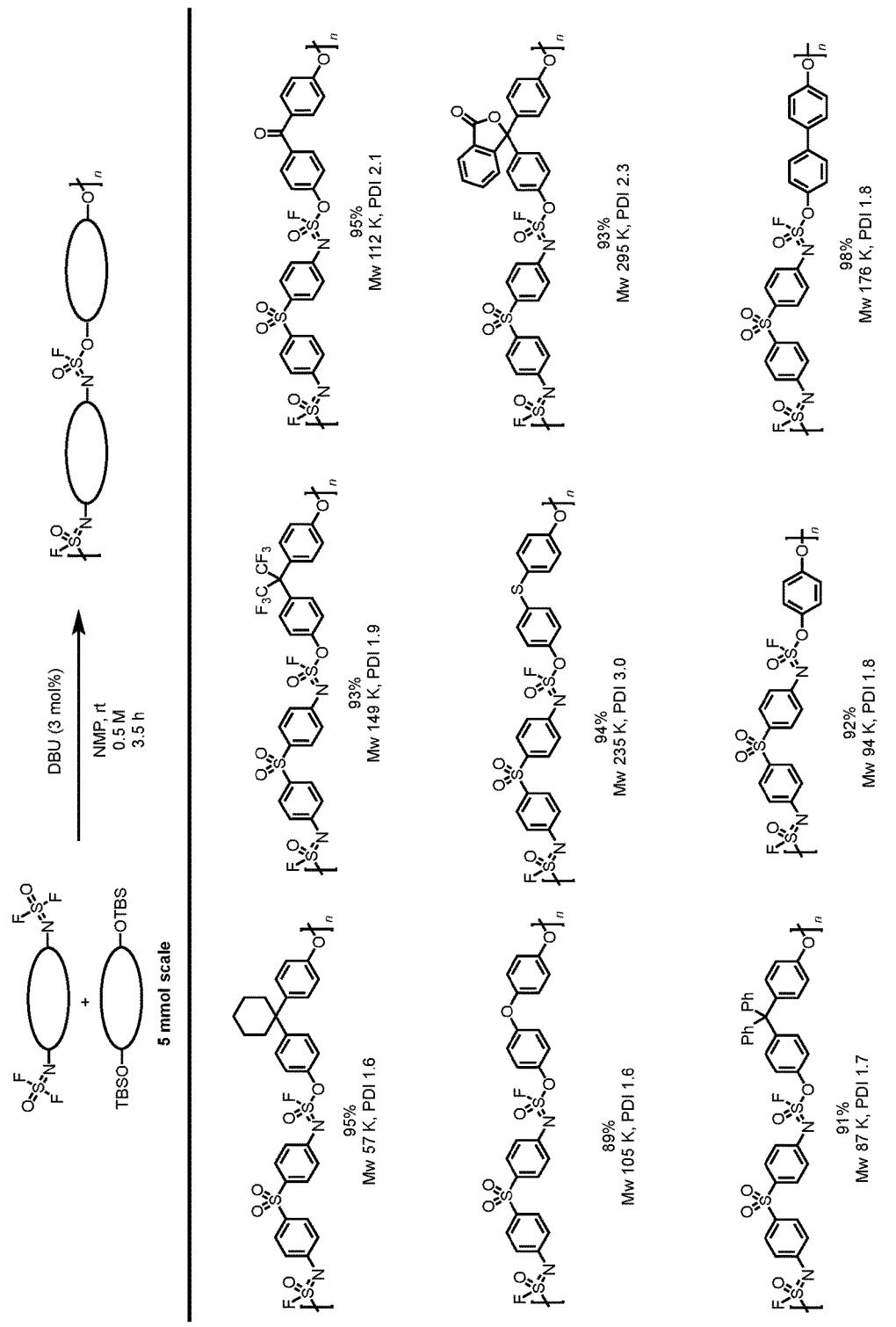
FIG. 12A illustrates the polymerization reaction using different silyl ethers.
Figure 12B:
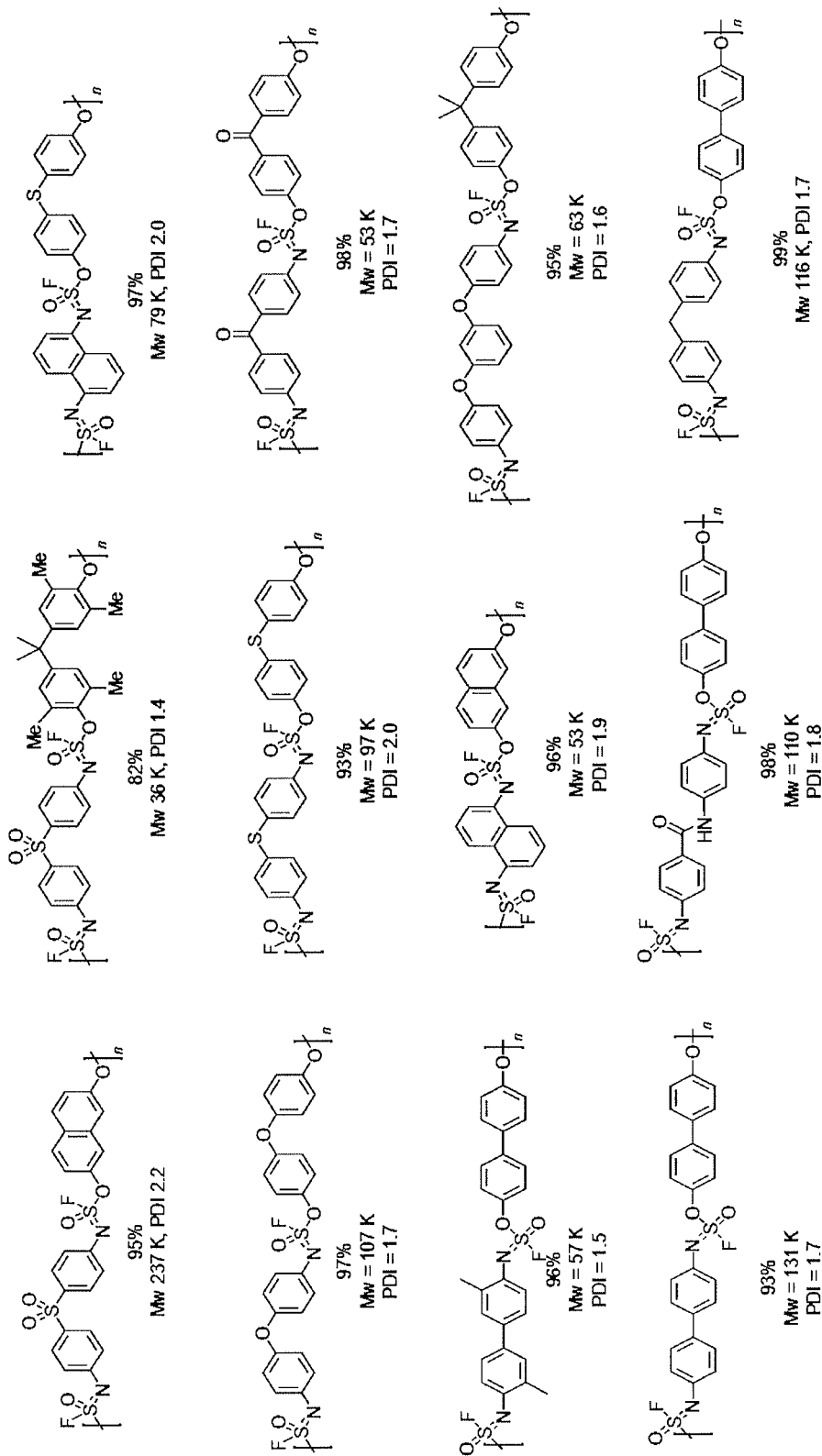
FIG. 12B illustrates additional polymerization reactions using different silyl ethers.
Figure 12C:
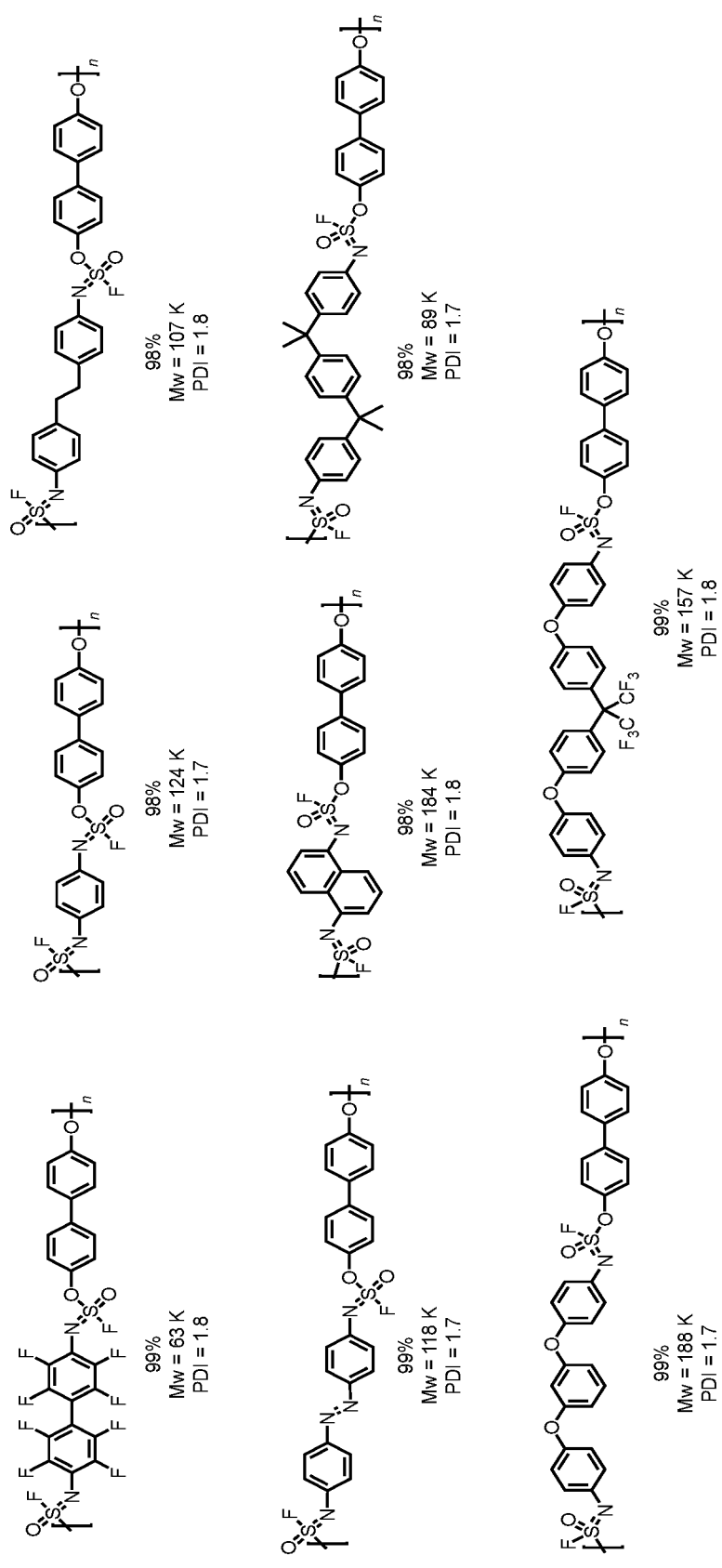
FIG. 12C illustrates more additional polymerization reactions using different silyl ethers.

Polymer-supported $F(HF)_w$, also has been described; see, Cousseau et al., *B. Soc. Chim. Fr.* 1986, p. 910-915. To explore the potential properties of SOF$_4$ based polymers, several substrates were prepared (FIG. 11). The polymerization was conducted with different silyl ethers, all giving excellent yields and molecular weight (FIGS. 12A, 12B, and 12C).

The silyl fluoride byproduct of the reaction of an S—F compound with a silyl ether or silyl amine, such as the polymerization and discrete molecule reactions described above, can be recycled by reaction with a salt (e.g., a sodium or potassium salt) of a phenolic monomer precursor (e.g., bisphenol A) to form a useful bis-silylated monomer (e.g., a bis-silyl bisphenol A) and a fluoride salt (e.g., sodium fluoride). The bis-silylated monomer can be utilized in another polymerization reaction.

The following examples are presented to illustrate certain, embodiments, aspects and features of the invention, but are not to be considered as limiting.

EXAMPLES

Abbreviations

BEMP=2-tert-butylimino-2-diethylamino-1,3-dimethylperhydro-1,3,2-diazaphosphorine; DBU=1,8-diazabicyclo[5.4.0]undec-7-ene; TMS=trimethylsilyl; TBS=tert-butyldimethylsilyl General Information $^1$H spectra were recorded on BRUKER AV-600™, BRUKER AV-400™ instruments; $^{13}$C NMR were recorded on BRUKER AV-600™. $^{19}$F NMR were recorded on BRUKER AV-400™. The chemical shifts (δ) are expressed in parts per million relative to TMS or residual acetonitrile or DMSO as internal standards. Proton magnetic resonance ($^1$H NMR) spectra were recorded at 600 or 400 MHz with chemical shifts rounded to the nearest hundredth of a part per million (ppm). Carbon magnetic resonance ($^{13}$C NMR) spectra were recorded at 150 MHz with chemical shifts rounded to the nearest tenth of a ppm. Fluorine magnetic resonance ($^{19}$F NMR) spectra were recorded at 376 MHz with chemical shifts rounded to the nearest tenth of a ppm. NMR acquisitions were performed at 295 K unless otherwise noted. Abbreviations are: s, singlet; d, doublet; t, triplet; q, quartet; p, pentet; and br s, broad singlet. Infrared spectra were recorded as pure undiluted samples using THERMONICOLET AVATAR™ 370 Fourier transform infrared spectrometer with a SMART MIRACLE™ HATR attachment. Melting points (mp) were determined using a THOMAS-HOOVER™ melting point apparatus and are uncorrected. GC-MS data were recorded on an AGILENT 7890A GC™ system with an AGILENT 5975C INERT™ MSD system or SHIMADZU GCMS-QP2010 SE™ operating in the electron impact (EI+) mode. LC-MS was performed on an AGILENT 1260™ LC/MSD with an AGILENT 6120™ quadrupole mass spectrometer (electrospray ionization, ES) eluting with 0.1% trifluoroacetic acid in H$_2$O and 0.05% trifluoroacetic acid in CH$_3$CN. High resolution mass spectrometry was performed on an AGILENT™ ES-TOF instrument. Pre-coated MERCK™ F-254 silica gel plates were used for thin layer analytical chromatography (TLC) and visualized with short wave UV light or by potassium permanganate stain. Column chromatography was performed using EMD (Merck) Silica Gel 60 (40-63 m).

Ex. 1: Preparation of SOF$_4$

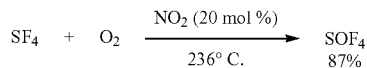

This procedure was slightly modified from the Smith and Engelhardt method (W. C. Smith, V. A. Engelhardt, *J. Am. Chem. Soc.* 1960, 82, 3838.). An autoclave was purchased from Parr Instrument Company. The autoclave main body is Alloy 400, and has a maximum pressure rating of 3000 psi. Stainless steel material will be badly corroded in this reaction. Rupture disc: 526HCPG Inconel (Must be Gold faced—A Rupture disc that is made of Alloy 600 will burst here). Shield should be used during the reaction. NO$_2$ and SF$_4$ are highly toxic, and should be filled into the autoclave in an efficiently ventilated hooded area. The hose used for filling of NO$_2$ and SF$_4$ must be corrosive-resistant (i.e. the A506HC Assembly from Parr). The hose used for filling of O$_2$ is the A495HC Hose Assembly (The same hose must not be used for other reducing gas, i.e. H$_2$).

About 450 mL of the autoclave was cooled by immersing into a dry ice/acetone bath. Next, 10.0 g of NO$_2$ followed by 100 g of SF$_4$ were sequentially transferred into the autoclave. The system was then warmed to room temperature and O$_2$ slowly introduced into the system until the final pressure reached 500 psi. The autoclave was then heated to about 238° C. (oil bath temperature) in an efficiently ventilated and hooded area for 8 hours. The max-pressure reached 1700 psi and then slowly dropped to 1250 psi. The reaction was allowed to cool to room temperature upon standing. The Autoclave was then immersed into a dry ice/acetone bath for 15 minutes, and the excess of O$_2$ was released and passed through an aqueous solution of NaOH (10% in water). After most of the O$_2$ had been released, the valve was closed. The autoclave was then warmed up to about 0° C. in an ice/NaCl bath. $^{19}$F NMR (CD$_2$Cl$_2$) showed that the major F-containing product was SOF$_4$, together with minor quantities of SOF$_2$ and SO$_2$F$_2$. To another autoclave was added 100 mL of DMF (anhydrous) and cooled in a liquid nitrogen bath. The gas was then transferred from the reaction autoclave into the DMF-containing autoclave. The autoclave was then warmed up to room temperature and kept for 1.5 hours. $^{19}$F NMR (CD$_2$Cl$_2$) indicated that most of the SOF$_2$ had been removed and that the residual SO$_2$F$_2$ had no adverse effect on later reactions. The gas was then transferred (use liquid nitrogen bath) and stored in a small gas tank for use (100 g, 87%).

Ex. 2: The Reaction of Amines with SOF$_4$

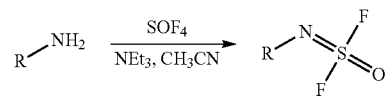

General Procedure I: A round-bottom flask with a magnetic stir bar is charged with amine, acetonitrile (0.2 M) and triethylamine. The flask is then sealed with a SUBA-SEAL® Septum, and an empty balloon, attached to a needle fixed syringe, is inserted into the septum.

A needle linked to a vacuum pump is then inserted into the septum, and the atmosphere in the flask is evacuated under reduced pressure until bubbles form and the balloon collapses around the syringe as a tight seal. The needle connected to the vacuum pump is then removed. Next, approximately one equivalent of SOF$_4$ is introduced into the flask via a separate syringe (i.e., 1 mmol of the amine, used 25 mL flask, after evacuation of the air, the SOF$_4$ is added until tension of the balloon is released). After stirring at room temperature for 0.5 hours, the CH$_3$CN is removed under reduced pressure and rotary evaporation. The product is purified by flash column chromatography over silica gel.

Ex. 3: 1,4-Phenylenedisulfurimidoyl Difluoride

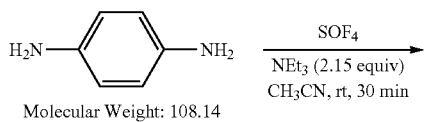

Molecular Weight: 108.14

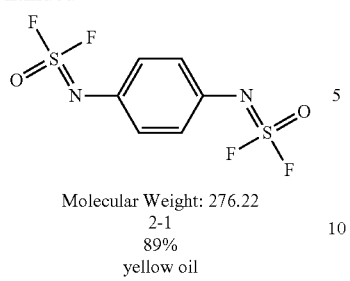

Molecular Weight: 276.22
2-1
89%
yellow oil

Following the General Procedure I: The reaction of benzene-1,4-diamine (108 mg, 1.00 mmol), Et$_3$N (300 μL, d=0.725 g/mL, 2.15 mmol) and SOF$_4$ in 5 mL of CH$_3$CN, afforded 2-1 (247 mg, 89%) as yellow oil. $^1$H NMR (600 MHz, CDCl$_3$) δ 7.13 (s, 4H); $^{13}$C NMR (150 MHz, CDCl$_3$) δ 133.6, 124.3 (t, J=2.9 Hz); $^{19}$F NMR (376 MHz, CDCl$_3$) δ 46.1; EI (m/z): 276 [M]$^+$.

Ex. 4: 1,3-Phenylenedisulfurimidoyl Difluoride

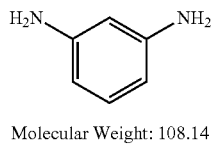

Molecular Weight: 108.14

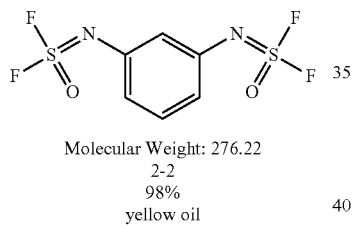

Molecular Weight: 276.22
2-2
98%
yellow oil

Following the General Procedure I: The reaction of benzene-1,3-diamine (108 mg, 1.00 mmol), Et$_3$N (300 μL, d=0.725 g/mL, 2.15 mmol), and SOF$_4$ in 5 mL of CH$_3$CN afforded 2-2 (258.3 mg, 98%) as yellow oil. $^1$H NMR (600 MHz, CDCl$_3$) δ 7.35 (t, J=8.1 Hz, 1H), 7.02 (dd, J=8.1, 2.0 Hz, 2H), 6.91 (d, J=2.6 Hz, 1H); $^{13}$C NMR (150 MHz, CDCl$_3$) δ 137.3, 130.7, 121.17 (m), 119.2 (m); $^{19}$F NMR (376 MHz, CDCl$_3$) δ 46.3; EI (m/z): 276 [M]$^+$.

Following the General Procedure I but without Et$_3$N: The reaction of benzene-1,3-diamine (108 mg, 1.00 mmol) and SOF$_4$ in 5 mL of CH$_3$CN afforded 2-2 (209 mg, 76%) as yellow oil.

Ex. 5: (4-(Fluorosulfonyl)phenyl)iminosulfur Oxydifluoride

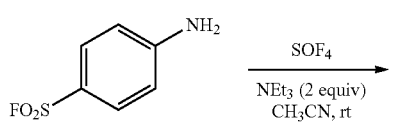

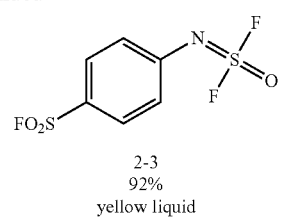

2-3
92%
yellow liquid

Following the General Procedure I: The reaction of 4-aminobenzenesulfonyl fluoride (87.6 mg, 0.50 mmol), Et$_3$N (139 μL, 1.00 mmol) and SOF$_4$ in 5 mL of CH$_3$CN, afforded 2-3 (120 mg, 92%) as yellow liquid. $^1$H NMR (600 MHz, CDCl$_3$) δ 8.04 (d, J=8.7 Hz, 1H), 7.39 (d, J=8.7 Hz, 1H); $^{13}$C NMR (150 MHz, CDCl$_3$) δ 142.8, 130.4, 130.2, 124.7, 124.7; $^{19}$F NMR (376 MHz, CDCl$_3$) δ 66.1, 47.0; EI (m/z): 259 [M]+.

Ex. 6: (4-Ethynylphenyl)sulfurimidoyl Difluoride

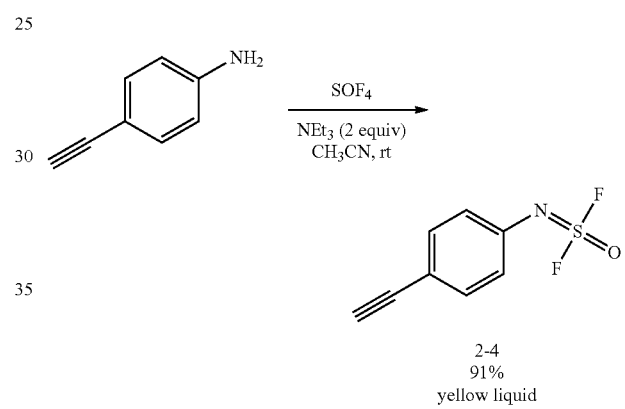

2-4
91%
yellow liquid

Following the General Procedure I: The reaction of 4-ethynylaniline (1.17 g, 10.0 mmol), Et$_3$N (2.02 g, 2.78 mL, d=0.725 g/mL, 20.0 mmol) and SOF$_4$ in 20.0 mL of CH$_3$CN, afforded 2-4 (1.83 g, 91%) as yellow liquid. $^1$H NMR (400 MHz, CDCl$_3$) δ 7.48 (d, J=8.5 Hz, 2H), 7.08 (d, J=8.5 Hz, 2H), 3.10 (s, 1H); $^{13}$C NMR (150 MHz, CDCl$_3$) δ 136.4, 133.5, 123.6, 123.5, 123.5, 120.1, 82.5, 78.0, 77.2, 77.0, 76.8; $^{19}$F NMR (376 MHz, CDCl$_3$) δ 46.7; EI (m/z): 201 [M]$^+$.

Following the General Procedure I but without Et$_3$N: The reaction of 4-ethynylaniline (2.34 g, 20.0 mmol) and SOF$_4$ in 40.0 mL of CH$_3$CN afforded 2-4 (2.82 g, 70%) as yellow liquid.

Ex. 7: (3,4-Dichlorophenyl)sulfurimidoyl Difluoride

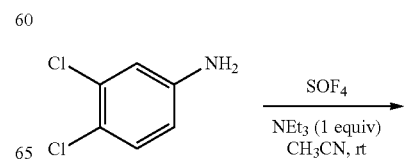

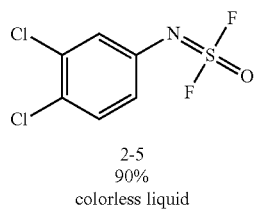

2-5
90%
colorless liquid

Following the General Procedure I: The reaction of 3,4-dichloroaniline (1.78 g, 11.0 mmol), Et₃N (1.11 g, 1.53 mL, d=0.725 g/mL, 11.0 mmol) and SOF₄ in 25 mL of CH₃CN, afforded 2-5 (2.43 g, 90%) as colorless liquid. ¹H NMR (400 MHz, CDCl₃) δ 7.43 (d, J=8.6 Hz, 1H), 7.33-7.17 (m, 1H), 6.99 (dd, J=8.6, 2.5 Hz, 1H); ¹³C NMR (150 MHz, CDCl₃) δ 135.3 (t, J=2.0 Hz), 133.5, 131.2, 130.8, 125.5 (d, J=3.0 Hz), 122.9 (t, J=3.1 Hz); ¹⁹F NMR (376 MHz, CDCl₃) δ 46.5; EI (m/z): 245 [M ($^{35}$Cl, $^{35}$Cl)]⁺, 247 [M ($^{35}$Cl, $^{37}$Cl)]⁺.

Ex. 8: (Sulfonylbis(4,1-phenylene))disulfurimidoyl Difluoride

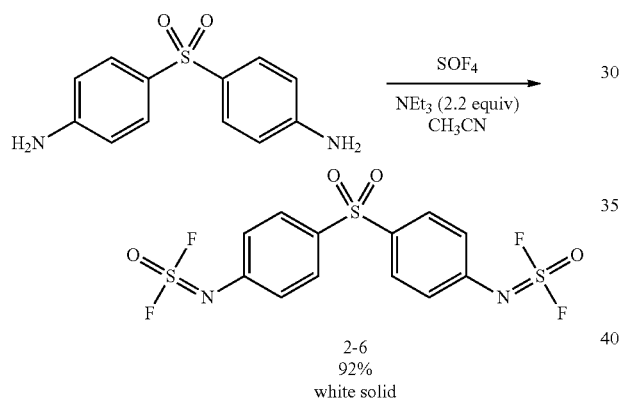

2-6
92%
white solid

A round-bottom flask (500 mL) with a magnetic stir bar was charged with 4,4'-sulfonyldianiline (24.8 g, 0.10 mol), acetonitrile (200 mL) and triethylamine (20.2 g, 27.9 mL, 0.20 mol). The flask was then sealed with a SUBA-SEAL® Septum, and an empty balloon, attached to a needle fixed syringe, was inserted into the flask. A needle linked to a vacuum pump was then inserted into the flask, and the atmosphere evacuated under reduced pressure until bubbles formed and the balloon became tense. The flask was immersed into an ice water bath and allowed to cool. Then, SOF₄ was slowly introduced into the flask via a needle, until the reaction had completed (TLC). The CH₃CN was removed under reduced pressure and rotary evaporation. The mixture was dissolved in EtOAc (500 mL) and washed with PBS buffer (pH=7.0, 2×100 mL) and brine (100 mL). After removing the solvent, the product was purified by flash column chromatography over silica gel (hex/EA=4/1) to give 2-6 (38.3 g 92%) as a white solid. Mp: 111° C.; ¹H NMR (600 MHz, CDCl₃) δ 7.94 (d, J=8.7 Hz, 4H), 7.25 (d, J=8.7 Hz, 4H). ¹³C NMR (150 MHz, CDCl₃) δ 140.8, 138.9, 129.5, 124.5 (m); ¹⁹F NMR (376 MHz, CDCl₃) δ 46.9; ESI-MS (m/z): 417 [M+H]⁺.

Ex. 9: (Propane-2,2-diylbis(4,1-phenylene))disulfurimidoyl Difluoride

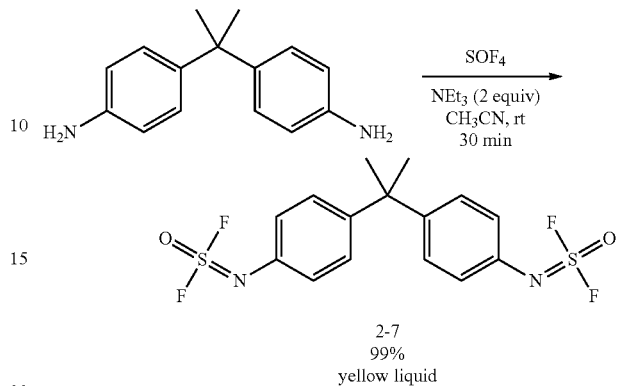

2-7
99%
yellow liquid

Following the General Procedure I: The reaction of 4,4'-(propane-2,2-diyl)dianiline (250 mg, 1.10 mmol), Et₃N (222 mg, 306 μL, d=0.725 g/mL, 2.20 mmol), and SOF₄ in 5.5 mL of CH₃CN afforded 2-7 (432 mg, 99%) as yellow liquid. ¹H NMR (600 MHz, CDCl₃) δ 7.23-7.17 (m, 4H), 7.06-7.00 (m, 4H), 1.66 (s, 6H); ¹³C NMR (150 MHz, CDCl₃) δ 148.2, 133.8, 128.0, 123.1, 123.1, 42.5, 30.7; ¹⁹F NMR (376 MHz, CDCl₃) δ 46.3; EI (m/z): 394 [M]⁺.

Ex. 10: tert-Butyl 3-((difluoro(oxo)-λ⁶-sulfanylidene)amino)azetidine-1-carboxylate

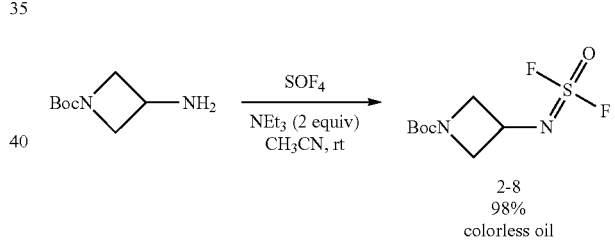

2-8
98%
colorless oil

Following the General Procedure I: The reaction of benzene-1,3-diamine (108 mg, 1.00 mmol), NEt₃ (300 μL, d=0.725 g/mL, 2.00 mmol), and SOF₄ in 5 mL of CH₃CN afforded 2-8 (247 mg, 89%) as colorless oil. ¹H NMR (600 MHz, CDCl₃) δ 4.37 (dddd, J=10.5, 7.2, 4.2, 1.6 Hz, 1H), 4.22 (dd, J=9.1, 7.4 Hz, 2H), 3.96 (dd, J=9.3, 5.0 Hz, 2H), 1.44 (s, 9H); ¹³C NMR (150 MHz, CDCl₃) δ 155.9, 80.1, 57.2, 44.8, 28.3; ¹⁹F NMR (376 MHz, CDCl₃) δ 47.9; ESI-MS (m/z): 257 [M+H]⁺.

Ex. 11: (3-((2-Oxo-2H-chromen-4-yl)oxy)propyl) sulfurimidoyl Difluoride

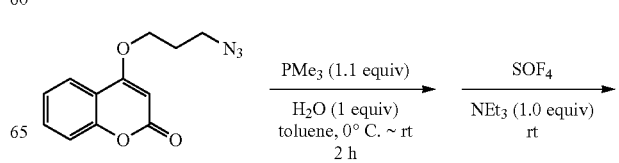

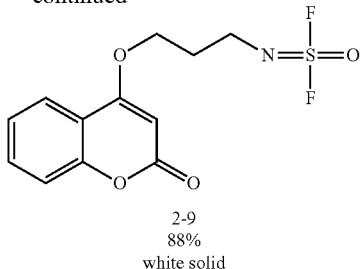

2-9
88%
white solid

Typical Procedure A: A Schlenk tube (25 mL) with a magnetic stir bar was charged with azide (123 mg, 0.50 mmol), toluene (5 mL), and H$_2$O (9.00 μL). The tube was then sealed with a SUBA-SEAL® Septum, and the air in the tube replaced with N$_2$ using a vacuum line and acetone/dry ice bath. PMe$_3$ (1.10 mL, 1.00 M) was added to the tube at 0° C. After addition, the reaction was warmed to room temperature and stirred for 2 hours. Then a balloon was attached to the tube. Et$_3$N (70.0 μL, 0.50 mmol) was added and a needle linked to a vacuum pump inserted into the flask. The atmosphere was evacuated under reduced pressure until bubbles formed and the balloon became tense. The needle connected with the vacuum pump was then removed. Then SOF$_4$ was introduced into the flask via a separate needle. After stirring at room temperature for 0.5 hour, the toluene was removed under reduced pressure and rotary evaporation. The product was purified by flash column chromatography over silica gel (hexanes/EA=2:1-1:1) to give 2-9 (134 mg, 88%) as a white solid. Mp 85-86° C.; $^1$H NMR (400 MHz, CDCl$_3$) δ 7.79 (dd, J=7.9, 1.6 Hz, 1H), 7.55 (ddd, J=8.7, 7.3, 1.6 Hz, 1H), 7.37-7.17 (m, 2H), 5.71 (s, 1H), 4.27 (t, J=5.9 Hz, 2H), 3.65 (tt, J=6.5, 3.9 Hz, 2H), 2.24 (p, J=6.1 Hz, 2H); $^{13}$C NMR (150 MHz, CDCl$_3$) δ 165.1, 162.5, 153.1, 132.3, 123.8, 122.6, 116.6, 115.4, 90.6, 65.5, 42.3, 29.4; $^{19}$F NMR (376 MHz, CDCl$_3$) δ 46.3; ESI-MS (m/z): 304 [M+H]$^+$.

Ex. 12: (2-Phenoxyethyl)sulfurimidoyl Difluoride

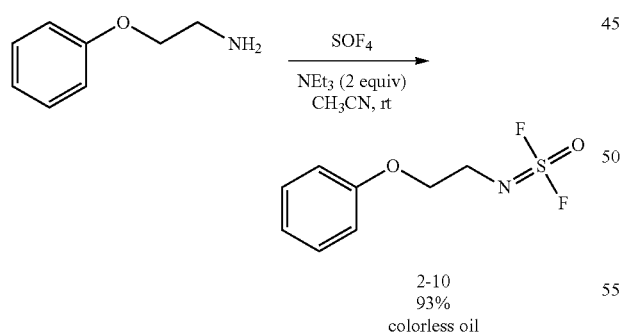

2-10
93%
colorless oil

Following the General Procedure I: The reaction of 2-phenoxyethan-1-amine (68.6 mg, 0.50 mmol), Et$_3$N (140 μL, d=0.725 g/mL, 1.00 mmol), and SOF$_4$ in 5 mL of CH$_3$CN afforded of 2-10 (102 mg, 93%) as colorless oil. $^1$H NMR (600 MHz, CDCl$_3$) δ 7.35-7.23 (m, 2H), 6.97 (tt, J=7.4, 1.1 Hz, 1H), 6.94-6.80 (m, 2H), 4.07 (t, J=5.3 Hz, 2H), 3.70 (tt, J=5.3, 3.9 Hz, 2H); $^{13}$C NMR (150 MHz, CDCl$_3$) δ 158.1, 129.5, 121.3, 114.5, 66.6, 66.6, 45.3; $^{19}$F NMR (376 MHz, CDCl$_3$) δ 47.3; ESI-MS (m/z): 222 [M+H]$^+$.

Following the General Procedure I but without Et$_3$N: The reaction of 2-phenoxyethan-1-amine (137 mg, 1.00 mmol) and SOF$_4$ in 5.00 mL of CH$_3$CN afforded 2-10 (126 mg, 57%) as colorless oil.

Ex. 13: (((3aS,5aR,8aR,8bS)-2,2,7,7-Tetramethyltetrahydro-3aH-bis([1,3]dioxolo)[4,5-b:4',5'-d]pyran-3a-yl)methyl)sulfurimidoyl Difluoride

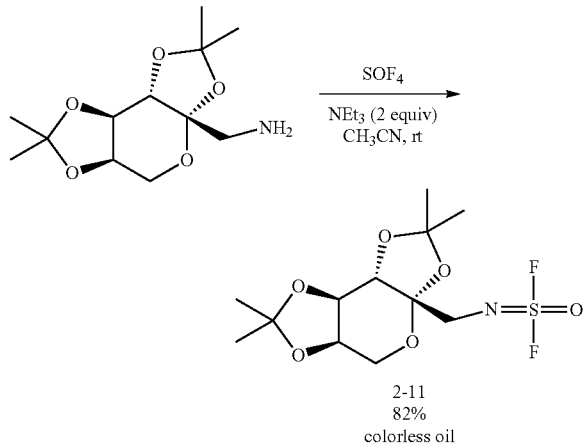

2-11
82%
colorless oil

Following the General Procedure I: The reaction of the amine (259 mg, 1.00 mmol), Et$_3$N (280 μL, d=0.725 g/mL, 1.00 mmol), and SOF$_4$ in 5 mL of CH$_3$CN afforded 2-11 (281 mg, 82%) as colorless oil. $[\alpha]^{25}{}_D$=−33.3 (c=1.00, CHCl$_3$); $^1$H NMR (600 MHz, CDCl$_3$) δ 4.62 (dd, J=7.8, 2.2 Hz, 1H), 4.32 (d, J=2.2 Hz, 1H), 4.24 (d, J=7.9 Hz, 1H), 3.92 (d, J=12.9 Hz, 1H), 3.77 (d, J=13.0 Hz, 1H), 3.65 (d, J=12.9 Hz, 1H), 3.49 (dt, J=12.7, 4.0 Hz, 1H), 1.55 (s, 3H), 1.47 (s, 3H), 1.42 (s, 3H), 1.35 (s, 3H); $^{13}$C NMR (150 MHz, CDCl$_3$) δ 109.1, 109.1, 101.7, 70.8, 70.3, 70.1, 61.6, 50.0, 26.6, 25.8, 25.3, 24.0; $^{19}$F NMR (376 MHz, CDCl$_3$) δ 47.1 (d, J=200.1 Hz), 45.7 (d, J=200.2 Hz); ESI-MS (m/z): 344 [M+H]$^+$.

Ex. 14: Methyl (R)-2-((difluoro(oxo)-λ$^6$-sulfanylidene)amino)-2-phenylacetate

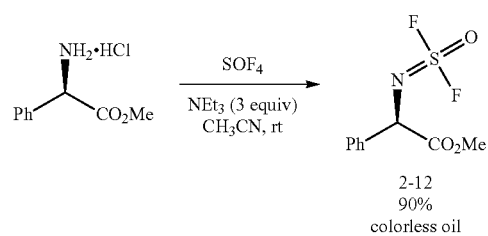

2-12
90%
colorless oil

Following the General Procedure I: The reaction of methyl (R)-2-amino-2-phenylacetate hydrochloride (101 mg, 0.50 mmol), Et$_3$N (210 μL, d=0.725 g/mL, 1.5 mmol), and SOF$_4$ in 5.00 mL of CH$_3$CN afforded 2-12 (112 mg, 90%) as colorless oil. $[\alpha]^{25}{}_D$=−95.4 (c=1.00, CHCl$_3$); $^1$H NMR (600 MHz, CDCl$_3$) δ 7.54-7.21 (m, 5H), 5.28 (s, 1H), 3.73 (s, 3H); $^{13}$C NMR (150 MHz, CDCl$_3$) δ 169.2 (t, J=3.7 Hz), 135.4, 129.0, 128.9, 127.1, 77.2, 77.0, 76.8, 62.2, 53.1;

$^{19}$F NMR (376 MHz, CDCl$_3$) δ 50.5 (d, J=197.6 Hz), 48.8 (d, J=197.2 Hz); ESI-MS (m/z): 272 [M+Na]$^+$.

Ex. 15: (R)-(2-((tert-Butyldimethylsilyl)oxy)-1-phenylethyl)sulfurimidoyl Difluoride

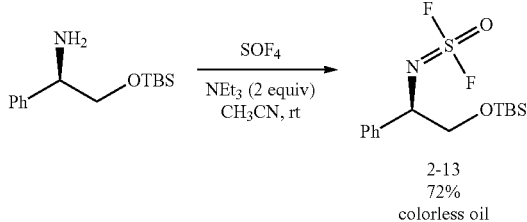 [SMILES: CC(C)(C)[Si](C)(C)OC[C@H](N)c1ccccc1 ; "SOF4" ; CC(C)(C)[Si](C)(C)OC[C@H](N=S(=O)(F)F)c1ccccc1]

2-13
72%
colorless oil

Following the General Procedure I: The reaction of (R)-2-((tert-butyldimethylsilyl)oxy)-1-phenylethan-1-amine (126 mg, 0.50 mmol), Et$_3$N (140 μL, d=0.725 g/mL, 1.00 mmol), and SOF$_4$ in 5 mL of CH$_3$CN afforded 2-13 (120 mg, 72%) as colorless oil. [α]$^{25}_D$=−41.7 (c=1.00, CHCl$_3$); $^1$H NMR (600 MHz, CDCl$_3$) δ 7.43-7.34 (m, 5H), 4.77 (ddt, J=8.7, 4.2, 1.8 Hz, 1H), 3.82-3.70 (m, 2H), 0.95 (s, 9H), 0.10 (d, J=9.2 Hz, 6H); $^{13}$C NMR (150 MHz, CDCl$_3$) δ 137.9, 128.5, 128.2, 126.7, 68.5, 68.4, 63.8, 25.8, 18.3, −5.5, −5.6; $^{19}$F NMR (376 MHz, CDCl$_3$) δ 51.2 (d, J=192.1 Hz), 48.0 (d, J=191.9 Hz); EI (m/z): 320 [M-Me]$^+$.

Ex. 16: (Adamantan-1-yl)sulfurimidoyl Difluoride

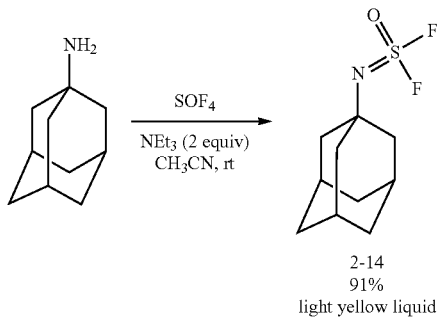 [SMILES: NC12CC3CC(CC(C3)C1)C2 ; "SOF4" ; O=S(F)(F)=NC12CC3CC(CC(C3)C1)C2]

2-14
91%
light yellow liquid

Following the General Procedure I: The reaction of adamantan-1-amine (151 mg, 1.00 mmol), NEt$_3$ (280 μL, d=0.725 g/mL, 2.00 mmol), and SOF$_4$ in 5.00 mL of CH$_3$CN afforded 2-14 (213 mg, 81%) as colorless oil. $^1$H NMR (600 MHz, CDCl$_3$) δ 2.05 (s, 3H), 1.88 (d, J=2.9 Hz, 6H), 1.69-1.51 (m, 6H); $^{13}$C NMR (150 MHz, CDCl$_3$) δ 59.6, 44.3, 35.7, 29.8; $^{19}$F NMR (376 MHz, CDCl$_3$) δ 59.6; EI (m/z): 235 [M]$^+$.

Ex. 17: (1-Ethynylcyclohexyl)sulfurimidoyl Difluoride

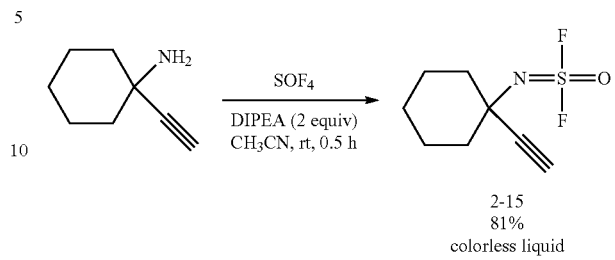

2-15
81%
colorless liquid

Following the General Procedure I: The reaction of 1-ethynylcyclohexan-1-amine (123 mg, 1.00 mmol), DIPEA (259 mg, 348 μL, d=0.742 g/mL, 2.00 mmol), and SOF$_4$ in 5 mL of CH$_3$CN afforded 2-15 (167 mg, 81%) as colorless oil. $^1$H NMR (400 MHz, CDCl$_3$) δ 2.56 (s, 1H), 1.98 (dt, J=11.1, 4.6 Hz, 2H), 1.83-1.48 (m, 7H), 1.37-1.25 (m, 1H); $^{13}$C NMR (150 MHz, CDCl$_3$) δ 83.9, 73.3, 57.3, 40.06, 24.7, 22.5; $^{19}$F NMR (376 MHz, CDCl$_3$) δ 53.6; EI (m/z): 207 [M]$^+$.

Ex. 18: (3,4-Dihydroxyphenethyl)sulfurimidoyl Difluoride

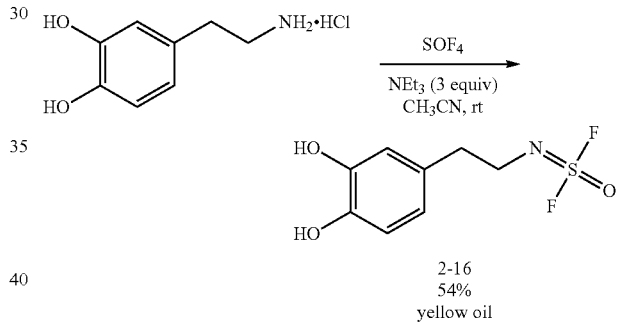

2-16
54%
yellow oil

Following the General Procedure I: The reaction of the dopamine hydrochloride (94.8 mg, 0.50 mmol), Et$_3$N (210 μL, d=0.725 g/mL, 1.50 mmol), and SOF$_4$ in 5 mL of CH$_3$CN afforded 2-16 (64.0 mg, 54%) as yellow oil. $^1$H NMR (600 MHz, CDCl$_3$) δ 6.79 (d, J=8.1 Hz, 1H), 6.72 (s, 1H), 6.64 (d, J=8.1 Hz, 1H), 5.60 (s, 1H), 5.53 (s, 1H), 3.54-3.48 (m, 2H), 2.78 (t, J=7.2 Hz, 2H); $^{13}$C NMR (150 MHz, CDCl$_3$) δ 143.5, 142.1, 131.0, 121.4, 116.0, 115.5, 47.4, 36.4; $^{19}$F NMR (376 MHz, CDCl$_3$) δ 46.9; ESI-MS (m/z): 236 [M−H].

Ex. 19: (2-(1H-indol-3-yl)ethyl)sulfurimidoyl Difluoride

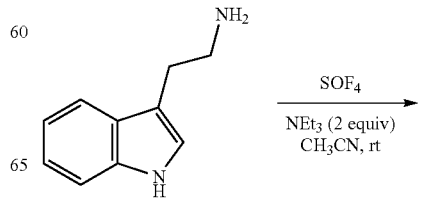

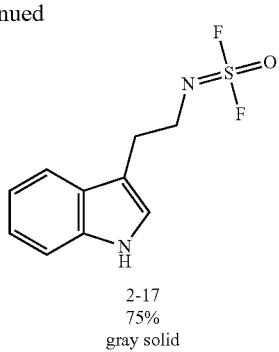

2-17
75%
gray solid

Following the General Procedure I: The reaction of tryptamine (80.1 mg, 0.50 mmol), Et₃N (140 μL, d=0.725 g/mL, 1.0 mmol), and SOF₄ in 5.00 mL of CH₃CN afforded of 2-17 (91.2 mg, 75%) as a as grey solid. Mp. 43-44° C.; ¹H NMR (600 MHz, CDCl₃) δ 7.83 (s, 1H), 7.56 (dd, J=7.9, 1.1 Hz, 1H), 7.28 (dd, J=8.1, 1.0 Hz, 1H), 7.19 (ddd, J=8.1, 6.9, 1.2 Hz, 1H), 7.12 (ddd, J=8.0, 6.9, 1.1 Hz, 1H), 6.94 (d, J=2.4 Hz, 1H), 3.60 (tt, J=7.6, 4.0 Hz, 2H), 3.04 (t, J=7.5 Hz, 2H); ¹³C NMR (150 MHz, CDCl₃) δ 136.1, 127.0, 122.4, 122.1, 119.5, 118.8, 111.9, 111.2, 46.5, 26.8; ¹⁹F NMR (376 MHz, CDCl₃) δ 47.0; ESI-MS (m/z): 245 [M+H]⁺.

Ex. 20: (((1R,4aS,10aR)-7-Isopropyl-1,4a-dimethyl-1,2,3,4,4a,9,10,10a-octahydrophenanthren-1-yl)methyl)sulfurimidoyl Difluoride

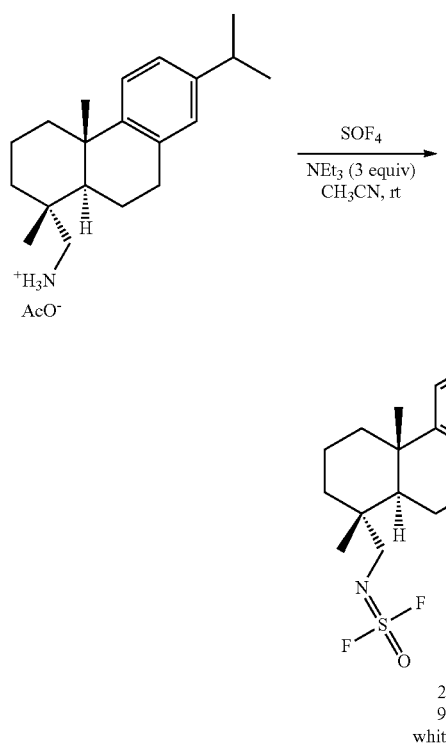

2-18
91%
white solid

Following the General Procedure I: The reaction of the amine (173 mg, 0.50 mmol), Et₃N (210 μL, d=0.725 g/mL, 1.50 mmol), and SOF₄ in 5 mL of CH₃CN afforded 2-18 (168 mg, 91%) as white solid. Mp. 73-74° C.; [α]²⁵_D=51.1 (c=1.00, CHCl₃); ¹H NMR (600 MHz, CDCl₃) δ 7.17 (d, J=8.2 Hz, 1H), 6.99 (dd, J=8.3, 2.0 Hz, 1H), 6.88 (d, J=2.1 Hz, 1H), 3.29 (dt, J=12.3, 3.8 Hz, 1H), 3.00 (dt, J=12.3, 4.0 Hz, 1H), 2.91-2.83 (m, 2H), 2.85-2.78 (m, 1H), 2.27 (dd, J=13.0, 3.4 Hz, 1H), 1.82-1.63 (m, 5H), 1.51-1.41 (m, 1H), 1.39 (td, J=13.2, 9.4 Hz, 2H), 1.24-1.19 (m, 9H), 0.93 (s, 3H); ¹³C NMR (150 MHz, CDCl₃) δ 147.0, 145.6, 134.5, 126.8, 124.3, 123.9, 56.7, 44.2, 38.2, 37.3, 37.3, 35.6, 33.4, 30.0, 25.2, 24.0, 18.8, 18.6, 18.3; ¹⁹F NMR (376 MHz, CDCl₃) δ 46.3; EI (m/z): 369 [M]⁺.

Ex. 21: Octadecylsulfurimidoyl Difluoride

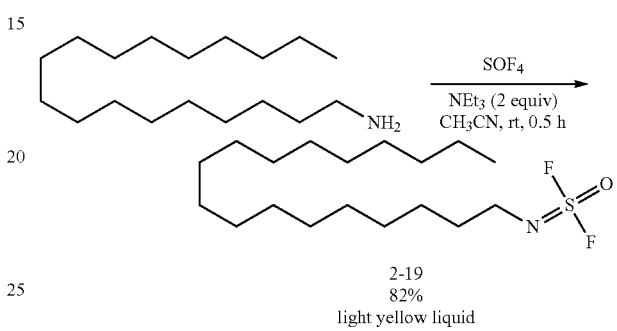

2-19
82%
light yellow liquid

Following the General Procedure I: The reaction of the amine (270 mg, 1.00 mmol), Et₃N (280 μL, d=0.725 g/mL, 2.00 mmol), and SOF₄ in 5.00 mL of CH₃CN afforded 2-19 (290 mg, 82%) as light yellow liquid. ¹H NMR (600 MHz, CDCl₃) δ 3.34 (tt, J=6.9, 4.0 Hz, 2H), 1.61 (p, J=7.0 Hz, 2H), 1.26 (s, 30H), 0.88 (t, J=7.0 Hz, 3H); ¹³C NMR (150 MHz, CDCl₃) δ 46.3, 31.9, 29.7, 29.7, 29.6, 29.6, 29.5, 29.4, 29.0, 26.5, 22.7, 14.1; ¹⁹F NMR (376 MHz, CDCl₃) δ 46.6; HRMS (ESI-TOF) Calculated for $C_{18}H_{38}F_2NOS^+$[M+H]+: 354.2637; found: 354.2634.

Ex. 22: ((Ethane-1,2-diylbis(oxy))bis(ethane-2,1-diyl))disulfurimidoyl Difluoride

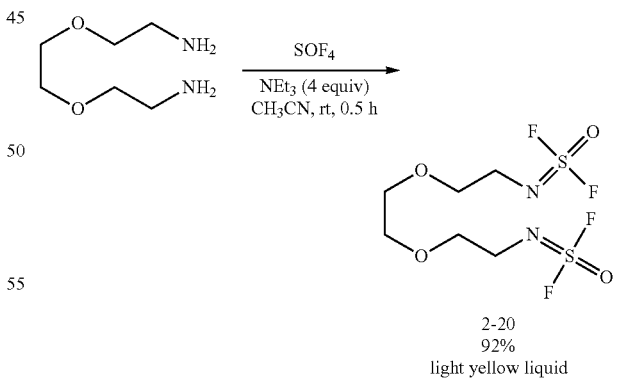

2-20
92%
light yellow liquid

Following the General Procedure I: The reaction of the amine (148 mg, 1.00 mmol), Et₃N (560 μL, d=0.725 g/mL, 4.00 mmol), and SOF₄ in 5 mL of CH₃CN afforded 2-20 (291 mg, 92%) as light yellow liquid. ¹H NMR (600 MHz, CDCl₃) δ 3.68-3.61 (m, 8H), 3.56-3.48 (m, 4H); ¹³C NMR (150 MHz, CDCl₃) δ 70.6, 70.2, 45.9; ¹⁹F NMR (376 MHz, CDCl₃) δ 47.2; ESI-MS (m/z): 317 [M+H]⁺.

Ex. 23: ((8R,9S,13S)-13-Methyl-17-oxo-7,8,9,11,12,13,14,15,16,17-decahydro-6H-cyclopenta[a]phenanthren-3-yl)sulfurimidoyl Difluoride

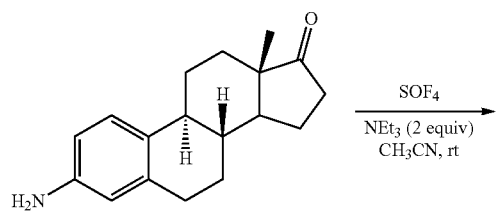

Following the General Procedure I: The reaction of the amine (81.0 mg, 0.30 mmol), Et$_3$N (84.0 μL, d=0.725 g/mL, 0.60 mmol), and SOF$_4$ in 5 mL of CH$_3$CN afforded 2-21 (101 mg, 95%) as white solid. Mp. 66-67° C.; $[\alpha]^{25}_D$=126.8 (c=1.00, CHCl$_3$); $^1$H NMR (600 MHz, CDCl$_3$) δ 7.26 (d, J=8.3 Hz, 1H), 6.91 (d, J=8.3 Hz, 1H), 6.86 (s, 1H), 2.90 (dd, J=8.5, 3.6 Hz, 2H), 2.51 (dd, J=19.1, 8.8 Hz, 1H), 2.42-2.37 (m, 1H), 2.27 (s, 1H), 2.18-2.12 (m, 1H), 2.09-2.00 (m, 2H), 1.97 (d, J=11.6 Hz, 1H), 1.72-1.32 (m, 6H), 0.91 (s, 3H); $^{13}$C NMR (150 MHz, CDCl$_3$) δ 220.5, 138.2, 137.8, 133.7, 126.6, 123.6, 120.7, 50.4, 47.9, 44.0, 37.9, 35.8, 31.5, 29.2, 26.2, 25.7, 21.5, 13.8; $^{19}$F NMR (376 MHz, CDCl$_3$) δ 46.2; ESI-MS (m/z): 354 [M+H]$^+$.

Ex. 24: ((3S,8R,9S,10R,13S,14S,17R)-17-Ethyl-10,13-dimethyl-17-((R)-6-methylheptan-2-yl)-2,3,4,7,8,9,10,11,12,13,14,15,16,17-tetradecahydro-1H-cyclopenta[a]phenanthren-3-yl)sulfurimidoyl Difluoride

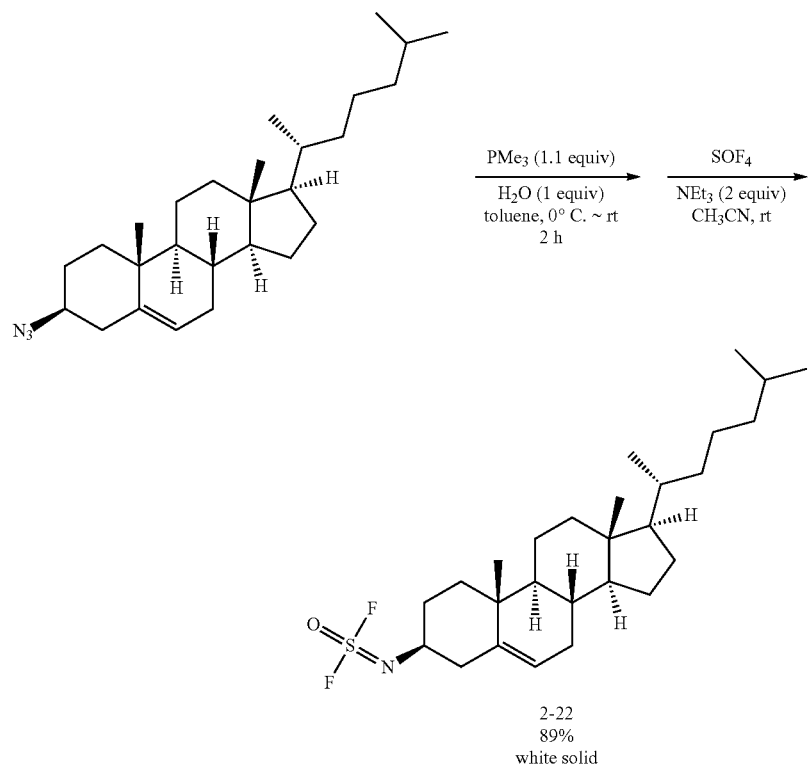

-continued

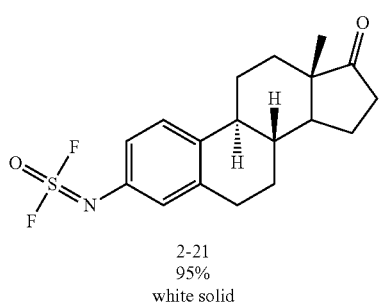

2-21
95%
white solid

Following the Typical Procedure A: The difluoride 2-22 (209 mg, 89%), was produced as a white solid from 206 mg (0.50 mmol) of the azide. Mp 107-108° C.; $[ca]^{25}_D$=−4.8 (c=1.00, CHCl$_3$); $^1$H NMR (600 MHz, CDCl$_3$) δ 5.39 (s, 1H), 3.41 (t, J=11.3 Hz, 1H), 2.42 (t, J=12.6 Hz, 1H), 2.29 (d, J=11.8 Hz, 1H), 2.04-1.95 (m, 2H), 1.90-1.80 (m, 3H), 1.76-1.66 (m, 1H), 1.63-0.79 (m, 36H), 0.68 (s, 3H); $^{13}$C NMR (150 MHz, CDCl$_3$) δ 139.8, 122.6, 58.0, 56.7, 56.1, 50.1, 42.3, 40.7, 39.7, 39.5, 37.6, 36.4, 36.2, 35.8, 31.9, 31.8, 30.6, 28.1, 28.0, 24.3, 23.8, 22.8, 22.6, 21.0, 19.3, 18.7, 11.9; $^{19}$F NMR (376 MHz, CDCl$_3$) δ 50.5; EI (m/z): 469 [M]$^+$.

Ex. 25: ((2S,3S,5R)-5-(5-Methyl-2,4-dioxo-3,4-dihydropyrimidin-1(2H)-yl)-2-((prop-2-yn-1-yloxy)methyl)tetrahydrofuran-3-yl)sulfurimidoyl Difluoride

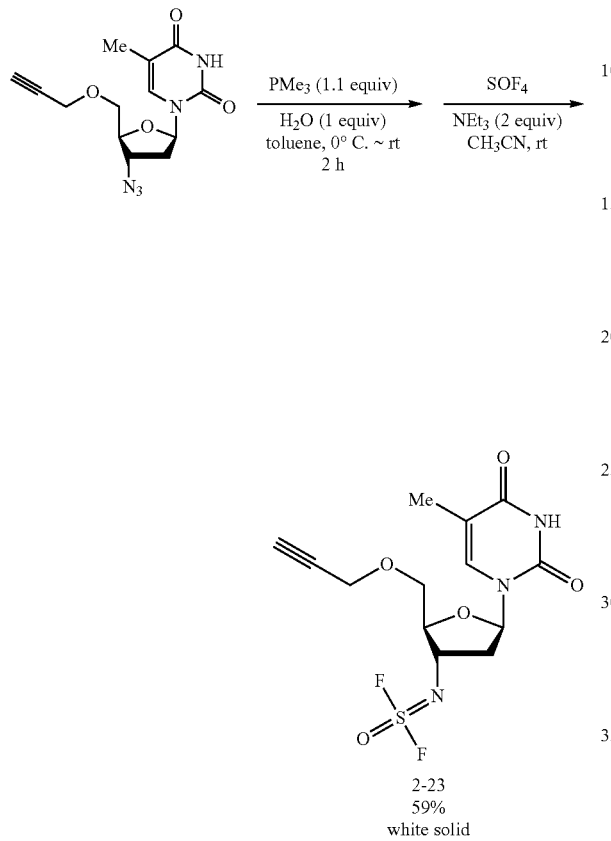

2-23
59%
white solid

Following the Typical Procedure A except that THF as solvent and 3.00 equiv of H$_2$O were used: The difluoride 2-23 (107 mg, 59%), was produced a white solid from 153 mg (0.50 mmol) of AZT. Mp 72-73° C.; [α]$^{25}_D$=46.1 (c=1.00, CHCl$_3$); $^1$H NMR (400 MHz, CDCl$_3$) δ 8.71 (s, 1H), 7.64-7.59 (m, 1H), 6.26 (t, J=5.8 Hz, 1H), 4.34 (d, J=6.6 Hz, 1H), 4.26 (d, J=2.4 Hz, 2H), 4.11 (dt, J=5.1, 2.3 Hz, 1H), 3.92 (dd, J=10.8, 2.3 Hz, 1H), 3.75 (dd, J=10.8, 2.4 Hz, 1H), 2.54-2.31 (m, 3H), 1.95 (d, J=1.3 Hz, 3H); $^{13}$C NMR (150 MHz, CDCl$_3$) δ 164.0, 150.3, 135.5, 110.9, 84.8, 84.4, 78.5, 75.5, 67.8, 58.6, 54.7, 39.8, 12.6; $^{19}$F NMR (376 MHz, CDCl$_3$) δ 49.0 (d, J=201.3 Hz), 47.3 (d, J=202.8 Hz); ESI-MS (m/z): 264 [M+H]$^+$.

Figure 14:
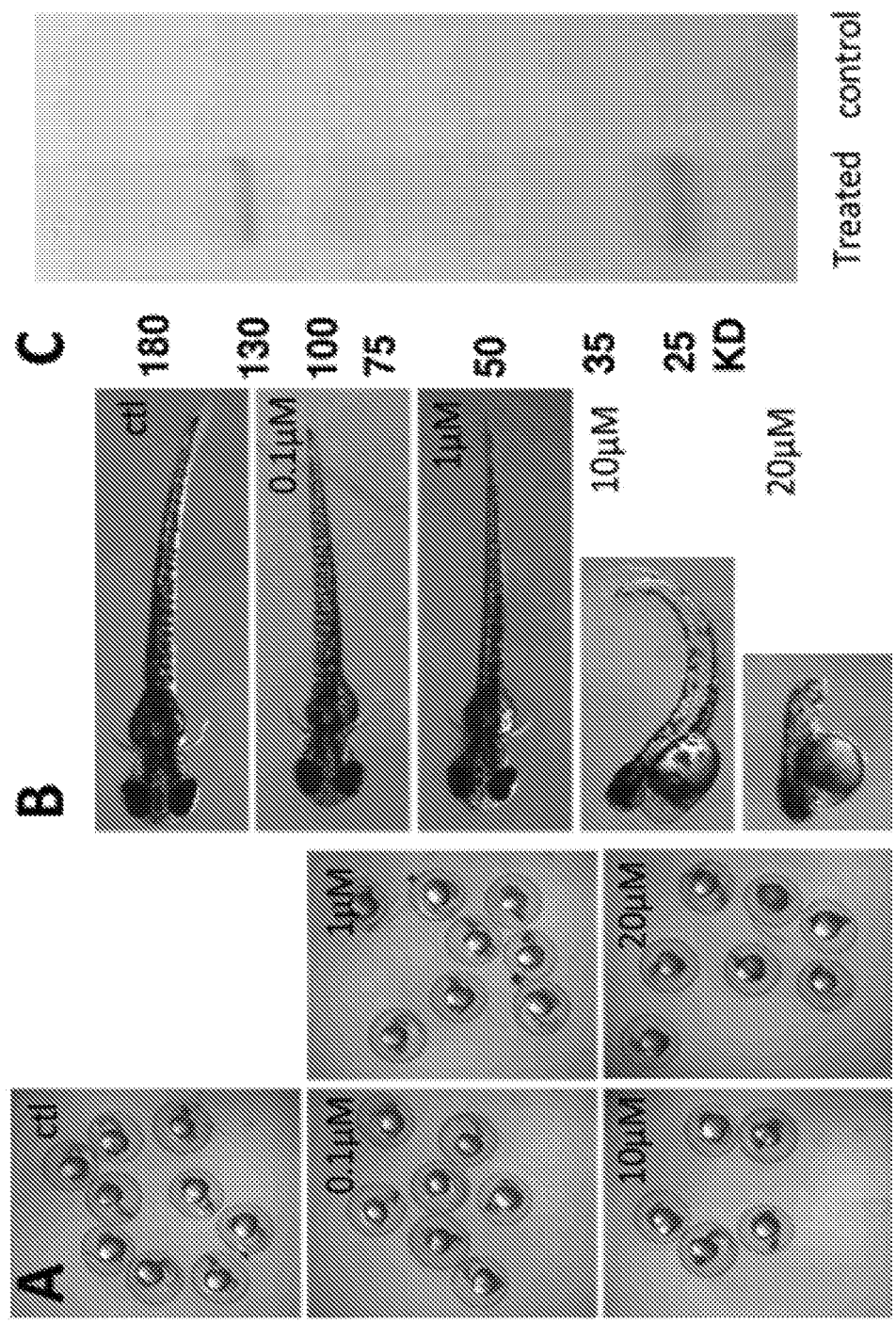
FIG. 14 provides micrographic images of zebrafish embryos: (A) and (B) Phenotypes generated by incubating zebrafish embryos with Compound 2-23 at various concentration; (C) Lysates from Compound 2-23 treated or untreated embryos at 24 hpf were reacted with biotin-azide, pull-down with streptavidin beads and analyzed using SDS-PAGE.

FIG. 14 provides micrographic images of zebrafish embryos. Panels (A) and (B) illustrate phenotypes generated by incubating zebrafish embryos with Compound 2-23 at various concentrations. As seen in the images, there were significant phenotypical changes in the embryos treated at concentrations of 10 and 20 μM. Panel (C) provides SDS-PAGE images of lysates from Compound 2-23 treated or untreated embryos at 24 hours post fertilization (hpf). The lysates were treated with biotin-azide and a copper(I) catalyst to react with the terminal alkyne via a copper-catalyzed azide-alkyne Click reaction and thereby attach biotin to any Compound 2-23 that may have been bound to a protein in the lysate. The biotinated lysate was then pulled-down with streptavidin beads and analyzed using SDS-PAGE. The results indicate that Compound 2-23 bound to a protein of approximately 130 KDa size and perhaps some smaller peptides between 25 and 30 KDa in size.

Ex. 26: (9-((3aR,4R,6R,6aR)-6-(((tert-Butyldimethylsilyl)oxy)methyl)-2,2-dimethyltetrahydrofuro[3,4-d][1,3]dioxol-4-yl)-9H-purin-6-yl)sulfurimidoyl Difluoride

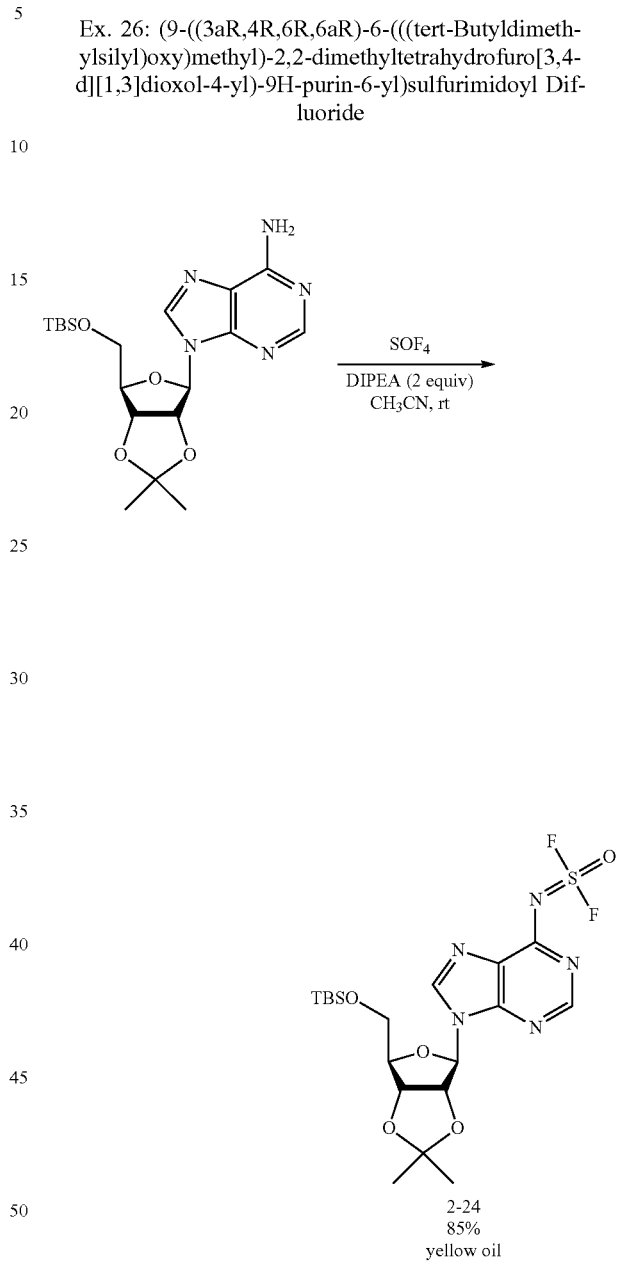

2-24
85%
yellow oil

Following the General Procedure I: The reaction of the amine (210 mg, 0.50 mmol), DIPEA (129 mg, d=0.742 g/mL, 174 μL, 1.00 mmol), and SOF$_4$ in 5 mL of CH$_3$CN afforded 2-24 (214 mg, 85%) as a yellow oil. [α]$^{25}_D$=−36.3 (c=1.00, CHCl$_3$); $^1$H NMR (600 MHz, CDCl$_3$) δ 8.72 (s, 1H), 8.37 (s, 1H), 6.24 (d, J=2.6 Hz, 1H), 5.20 (dd, J=6.2, 2.5 Hz, 1H), 4.93 (dd, J=6.2, 2.1 Hz, 1H), 4.49 (d, J=3.0 Hz, 1H), 3.90 (dd, J=11.4, 3.3 Hz, 1H), 3.78 (dd, J=11.4, 3.6 Hz, 1H), 1.63 (s, 3H), 1.40 (s, 3H), 0.80 (s, 9H); $^{13}$C NMR (150 MHz, CDCl$_3$) δ 152.2, 152.1, 148.4, 143.0, 126.7, 114.0, 92.0, 87.4, 85.2, 81.4, 63.6, 27.1, 25.7, 25.2, 18.2, −5.6, −5.7; $^{19}$F NMR (376 MHz, CDCl$_3$) δ 48.8; ESI-MS (m/z): 506 [M+H]$^+$.

Ex. 27: (4R)-2-Cyclohexyl-1-fluoro-4-((S)-(4-(4-fluorophenyl)piperazin-1-yl)(phenyl)methyl)-2,4-dihydro-3H-1λ⁶,2,5-thiadiazol-3-one 1-oxide

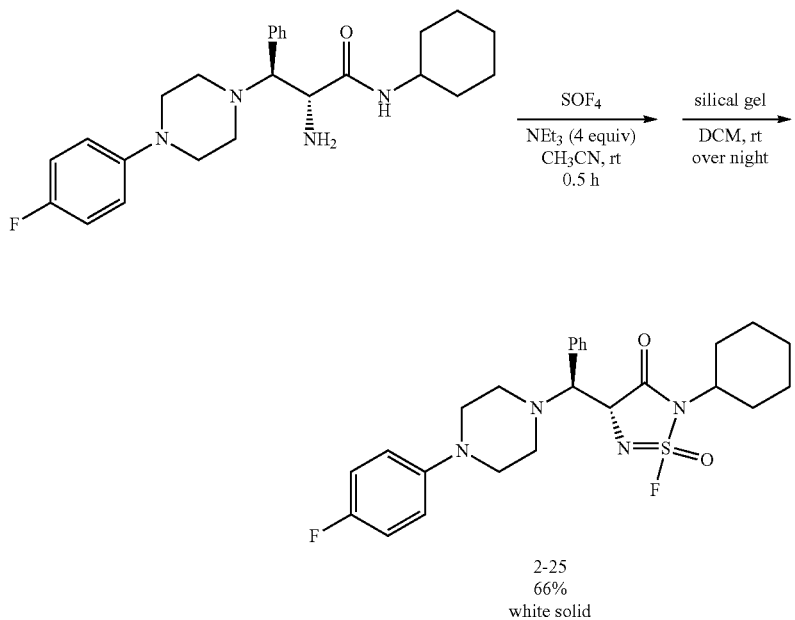

2-25
66%
white solid

Following the General Procedure I: The reaction of the amine (106 mg, 0.25 mmol), triethylamine (140 μL, 1.00 mmol), and SOF$_4$ in 5 mL of CH$_3$CN afforded a mixture. The CH$_3$CN was then removed under reduced pressure and rotary evaporation. The mixture was dissolved in 5 mL of CH$_2$Cl$_2$ and 5.00 g of silica gel was added and stirring at room temperature overnight. The product was purified by flash column chromatography over silica gel (hexanes/EA=4:1) to give 2-25 (80.0 mg, 66%, d.r.=1.57:1) as a white solid. Mp: 139-140° C.; [α]$^{25}$D=11.6 (c=1.00, CHCl$_3$); $^1$H NMR (600 MHz, CDCl$_3$) δ 7.54 (ddd, J=8.0, 3.0, 1.4 Hz, 2H), 7.39-7.28 (m, 3H), 6.91 (t, J=8.7 Hz, 2H), 6.77 (ddd, J=9.2, 4.6, 3.1 Hz, 2H), 4.71-4.52 (m, 1H), 4.34-4.28 (m, 1H), 4.08-3.96 (m, 1H), 3.05-2.90 (m, 6H), 2.41-2.35 (m, 2H), 2.09-1.82 (m, 6H), 1.69 (dq, J=10.3, 3.5 Hz, 1H), 1.42-1.30 (m, 2H), 1.28-1.18 (m, 1H); $^{13}$C NMR (150 MHz, CDCl$_3$) δ 172.9, 172.8, 157.8, 156.2, 147.9, 147.8, 135.6, 129.5, 129.4, 128.2, 128.2, 128.0, 127.9, 117.5, 117.5, 117.5, 117.4, 115.5, 115.4, 115.3, 115.3, 71.6, 71.6, 68.4, 67.9, 67.8, 56.9, 56.6, 52.1, 52.0, 50.6, 50.2, 30.6, 29.9, 29.7, 29.3, 25.7, 25.7, 25.6, 24.8, 24.7; $^{19}$F NMR (376 MHz, CDCl$_3$) δ 79.6, 78.1, −125.3; ESI-MS (m/z): 489 [M+H]$^+$.

Ex. 28: 4-((Difluoro(oxo)-λ⁶-sulfanylidene)amino)phenyl Sulfurofluoridate

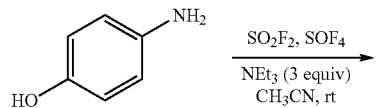

-continued

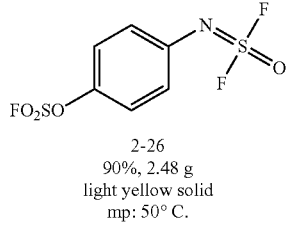

2-26
90%, 2.48 g
light yellow solid
mp: 50° C.

General Procedure II: A 500 mL round-bottom flask with a magnetic stir bar was charged with 4-aminophenol (1.09 g, 10.0 mmol), acetonitrile (20 mL), and triethylamine (3.03 g, 4.18 mL, 30.0 mmol). The flask was then sealed with a SUBA-SEAL® Septum, and an empty balloon, attached to a needle fixed syringe, was inserted into the flask. A needle linked to a vacuum pump was then inserted into the flask, and the atmosphere evacuated under reduced pressure until bubbles formed and the balloon became tense. The needle connected to the vacuum pump was then removed. Next a balloon containing SO$_2$F$_2$ (~250 mL) mounted on a separate needle fixed syringe was inserted in the seal, then the SOF$_4$ gas was introduced into the reaction flask until the completion of the reaction (TLC). The reaction mixture was further stirred at room temperature for 15 minutes, and then the CH$_3$CN was removed under reduced pressure and rotary evaporation. The product was purified by flash column chromatography over silica gel (hexanes/EA=5:1) affording 2-26 (2.48 g, 90%) as light yellow solid. Mp: 50° C.; $^1$H NMR (600 MHz, CDCl$_3$) δ 7.39-7.32 (m, 2H), 7.25-7.21 (m, 2H); $^{13}$C NMR (150 MHz, CDCl$_3$) δ 147.5, 136.4, 125.4, 122.4; $^{19}$F NMR (376 MHz, CDCl$_3$) δ 46.2, 37.1; ESI-MS (m/z): 276 [M+H]$^+$.

Ex. 29: 3-((Difluoro(oxo)-λ⁶-sulfanylidene)amino) phenyl Sulfurofluoridate

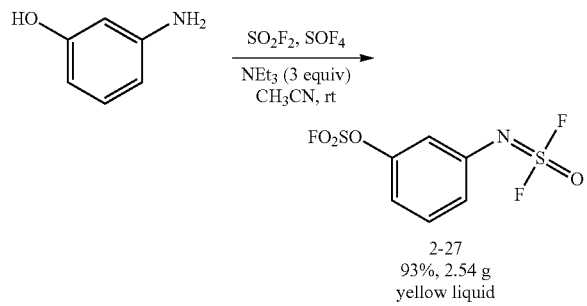

2-27
93%, 2.54 g
yellow liquid

Following the General Procedure II: The reaction of 4-aminophenol (1.09 g, 10.0 mmol), acetonitrile (20 mL) and triethylamine (3.03 g, 4.18 mL, 30.0 mmol) gave 2-27 (2.60 g, 93%) as yellow liquid. $^1$H NMR (600 MHz, CDCl$_3$) δ 7.49 (t, J=8.2 Hz, 1H), 7.28-7.23 (m, 1H), 7.21 (ddd, J=8.1, 2.1, 0.9 Hz, 1H), 7.14 (td, J=2.3, 0.7 Hz, 1H); $^{19}$F NMR (376 MHz, CDCl$_3$) δ 46.4, 37.7; $^{13}$C NMR (150 MHz, CDCl$_3$) δ 150.3, 137.9, 131.3, 123.7 (t, J=2.4 Hz), 118.6, 116.8 (t, J=3.4 Hz); EI (m/z): 275 [M]$^+$.

Ex. 30: 2-((Difluoro(oxo)-λ⁶-sulfanylidene)amino) phenyl Sulfurofluoridate

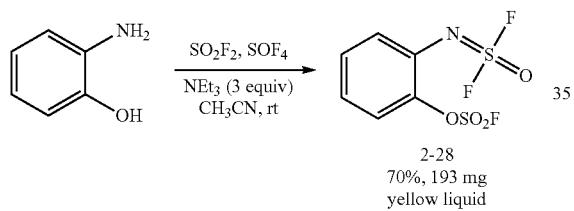

2-28
70%, 193 mg
yellow liquid

Following the General Procedure II: The reaction of 4-aminophenol (109 mg, 1.00 mmol), acetonitrile (5 mL) and triethylamine (303 mg, 0.418 mL, 3 mmol) gave 2-28 (193.3 mg, 70%) as yellow liquid. $^1$H NMR (600 MHz, CDCl$_3$) δ 7.48-7.38 (m, 2H), 7.38-7.29 (m, 2H); $^{13}$C NMR (150 MHz, CDCl$_3$) δ 143.2 (t, J=3.7 Hz), 129.7, 128.9, 127.5, 125.3 (t, J=1.8 Hz), 122.7; $^{19}$F NMR (376 MHz, CDCl$_3$) δ 47.7, 39.9; EI (m/z): 275 [M]$^+$.

Ex. 31: (4-Hydroxyphenyl)sulfurimidoyl Difluoride

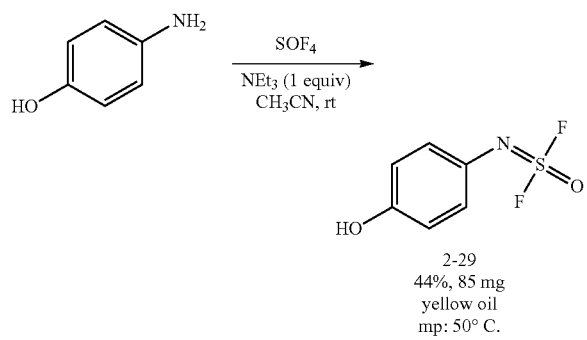

2-29
44%, 85 mg
yellow oil
mp: 50° C.

Following the General Procedure I: The reaction of 4-aminophenol (109 mg, 1.00 mmol), NEt$_3$ (101 mg, d=0.725 g/mL, 140 μL, 1.00 mmol), and SOF$_4$ in 5 mL of CH$_3$CN afforded 2-29 (84.8 mg, 44%) mg as a yellow oil. $^1$H NMR (400 MHz, CDCl$_3$) δ 6.99 (d, J=8.1 Hz, 2H), 6.81 (d, J=8.2 Hz, 2H), 6.10 (s, 1H); $^{13}$C NMR (150 MHz, CDCl$_3$) δ 153.6, 129.0, 124.6 (t, J=3.2 Hz), 116.3; $^{19}$F NMR (376 MHz, CDCl$_3$) δ 45.59; EI (m/z): 193 [M]$^+$.

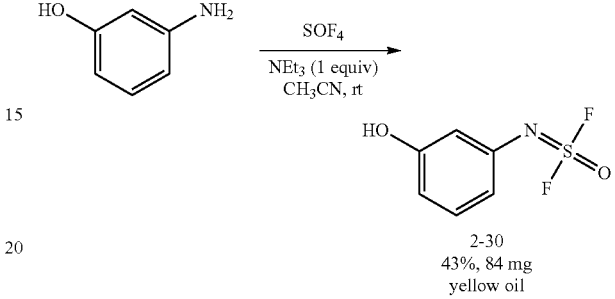

2-30
43%, 84 mg
yellow oil

Following the General Procedure I: The reaction of 3-aminophenol (109 mg, 1.00 mmol), NEt$_3$ (101 mg, d=0.725 g/mL, 140 μL, 1.0 mmol), and SOF$_4$ in 5 mL of CH$_3$CN afforded 2-30 (83.9 mg, 43%) as a yellow oil. $^1$H NMR (600 MHz, CDCl$_3$) δ 7.19 (t, J=8.1 Hz, 1H), 6.77-6.66 (m, 2H), 6.64 (t, J=2.2 Hz, 1H), 6.05 (s, 1H); $^{13}$C NMR (150 MHz, CDCl$_3$) δ 156.5, 137.0, 130.5, 115.8 (d, J=3.7 Hz), 113.4, 110.9 (t, J=3.2 Hz); $^{19}$F NMR (376 MHz, CDCl$_3$) δ 46.0; ESI-MS (m/z): 194 [M+H]$^+$.

Ex. 32: ((1R,3s,5S)-8-methyl-8-azabicyclo[3.2.1] octan-3-yl)sulfurimidoyl Difluoride

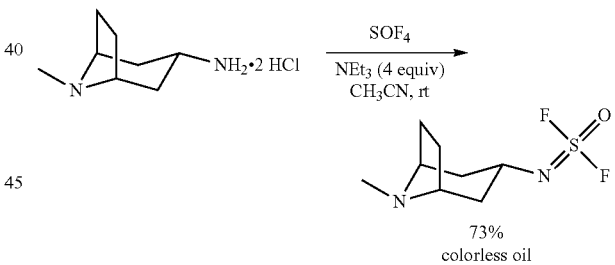

73%
colorless oil

Following the General Procedure I: the reaction of the amine (106.6 mg, 0.5 mmol), NEt$_3$ (280 μL, d=0.725 g/mL, 2.0 mmol), and SOF$_4$ in 5 mL of CH$_3$CN afforded 82.1 mg (73%) as colorless oil.

Ex. 33: The Reaction of Iminosulfur Oxydifluorides with Amines

General Procedure III: A 3 mL vial with a magnetic stir bar was charged with iminosulfur oxydifluoride (0.10 mmol), 1 mL of CH$_3$CN, and the amine (2 equiv). The mixture was stirred at room temperature for 0.5 hours then diluted with ethyl acetate (10 mL). The solution was washed with cold aq. HCl (0.1 M, 5 mL), water and brine, then dried over anhydrous MgSO$_4$. After filtration, the solvent was removed under reduced pressure and rotary evaporation. Where required the products could be purified by flash column chromatography over silica gel.

Ex. 34: N'-(4-Ethynylphenyl)-N,N-dimethylsulfuramidimidoyl Fluoride

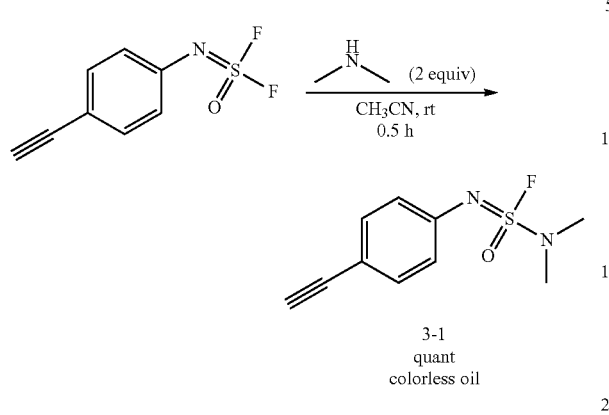

3-1
quant
colorless oil

Following the General Procedure III: The reaction of the iminosulfur oxydifluoride 2-4 (20.1 mg, 0.10 mmol) with dimethylamine (9.00 mg, 0.20 mmol) gave 3-1 (24.1 mg) as colorless oil. $^1$H NMR (400 MHz, CDCl$_3$ δ 7.37-7.30 (m, 2H), 7.02-6.94 (m, 2H), 3.02 (d, J=2.1 Hz, 6H), 2.96 (s, 1H); $^{13}$C NMR (150 MHz, CDCl$_3$) δ 140.9 (d, J=2.4 Hz), 133.1, 123.14 (d, J=3.1 Hz), 116.9, 83.5, 76.6, 38.8; $^{19}$F NMR (376 MHz, CDCl$_3$) δ 45.4; $^{19}$F NMR (376 MHz, CDCl$_3$) δ 45.4; ESI-MS (m/z): 227 [M+H]$^+$.

Ex. 35: N-Benzyl-N'-(4-ethynylphenyl)-N-methylsulfuramidimidoyl Fluoride

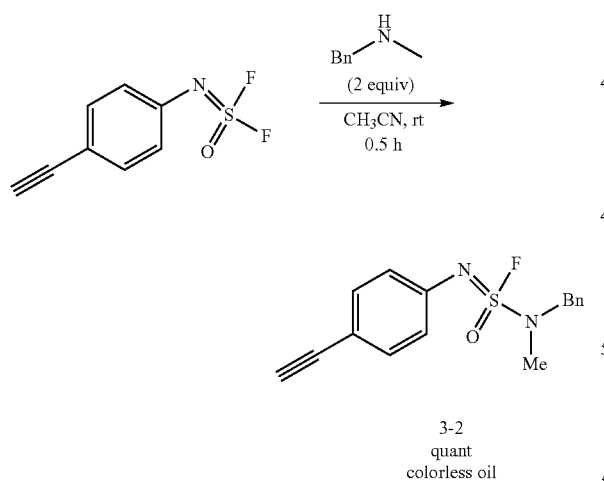

3-2
quant
colorless oil

Following the General Procedure III: The reaction of the iminosulfur oxydifluoride 2-4 (20.1 mg, 0.10 mmol) with N-methyl-1-phenylmethanamine (24.2 mg, 0.20 mmol) gave 3-2 (32.6 mg) as colorless oil. $^1$H NMR (400 MHz, CDCl$_3$) δ 7.38-7.25 (m, 5H), 7.01 (d, J=8.5 Hz, 2H), 4.53 (dd, J=3.2, 1.5 Hz, 2H), 2.96 (s, 1H), 2.89 (d, J=2.1 Hz, 3H); $^{13}$C NMR (150 MHz, CDCl$_3$) δ 141.0, 134.2, 133.2, 128.9, 128.5, 128.4, 123.2, 123.2, 117.0, 83.5, 76.7, 76.7, 55.1, 35.4; $^{19}$F NMR (376 MHz, CDCl$_3$) δ 52.4; ESI-MS (m/z): 303 [M+H]$^+$.

Ex. 36: N'-(4-Ethynylphenyl)-N-methyl-N-(prop-2-yn-1-yl)sulfuramidimidoyl Fluoride

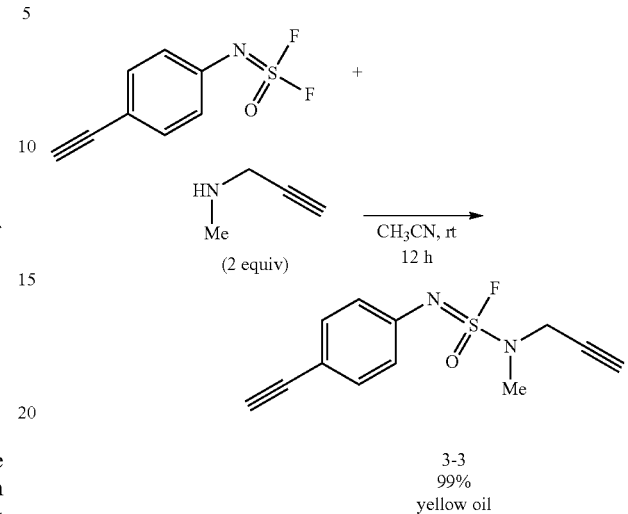

3-3
99%
yellow oil

Following the General Procedure III: The reaction of the iminosulfur oxydifluoride 2-4 (20.1 mg, 0.10 mmol) with N-methylprop-2-yn-1-amine (13.8 mg, 0.20 mmol) gave 3-3 (24.1 mg, 96%) as yellow oil after column chromatographic purification over silica gel (Hexanes/EA=10:1). $^1$H NMR (600 MHz, CDCl$_3$) δ 7.47-7.41 (m, 2H), 7.12-7.04 (m, 2H), 4.34 (dt, J=17.8, 2.0 Hz, 1H), 4.24 (dt, J=17.8, 2.4 Hz, 1H), 3.19 (d, J=1.6 Hz, 3H), 3.07 (s, 1H), 2.47 (t, J=2.5 Hz, 1H); $^{13}$C NMR (150 MHz, CDCl$_3$) δ 140.5, 133.2, 123.2 (d, J=3.1 Hz), 117.3, 83.4, 76.7, 75.6, 75.0, 41.4, 35.6; $^{19}$F NMR (376 MHz, CDCl$_3$) δ 52.2; ESI-MS (m/z): 251 [M+H]$^+$.

Ex. 37: N-(4-Ethynylphenyl)azetidine-1-sulfonimidoyl Fluoride

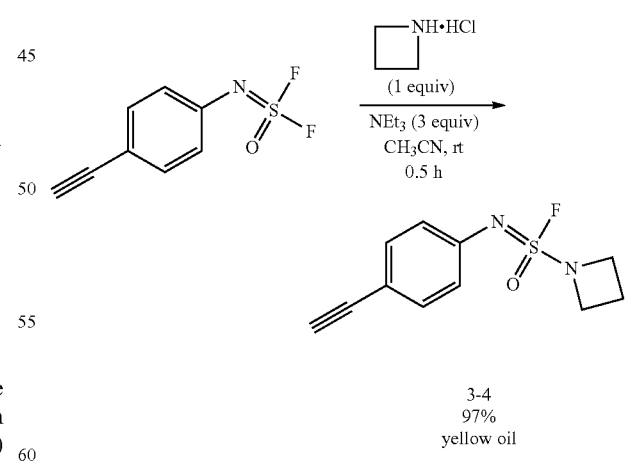

3-4
97%
yellow oil

Following the General Procedure III: The reaction of the iminosulfur oxydifluoride 2-4 (20.1 mg, 0.10 mmol) with azetidine (9.4 mg, 0.10 mmol) in the presence of triethylamine (42 μL, 0.30 mmol) gave 3-4 (23.1 mg, 97%) as yellow oil. $^1$H NMR (600 MHz, CDCl$_3$) δ 7.35-7.30 (m, 2H), 6.99-6.93 (m, 2H), 4.13 (dqd, J=17.3, 8.0, 1.4 Hz, 4H), 2.96 (s, 1H), 2.28 (q, J=7.8 Hz, 2H); ¹³C NMR (150 MHz, CDCl₃) δ 140.6 (d, J=4.2 Hz), 133.1, 123.3 (d, J=3.2 Hz), 117.1, 83.5, 76.6, 52.9, 15.3; ESI-MS (m/z): 239 [M+H]⁺.

Ex. 38: N-(4-Ethynylphenyl)pyrrolidine-1-sulfonimidoyl Fluoride

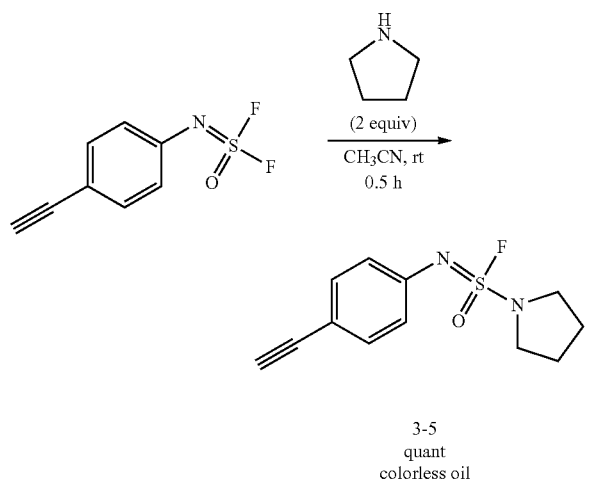

3-5
quant
colorless oil

Following the General Procedure III: The reaction of the iminosulfur oxydifluoride 2-4 (20.1 mg, 0.10 mmol) with pyrrolidine (14.2 mg, 0.20 mmol) gave 3-5 (25.4 mg) as colorless oil. ¹H NMR (400 MHz, CDCl₃) δ 7.32 (d, J=8.5 Hz, 2H), 7.02-6.95 (m, 2H), 3.50 (dp, J=6.7, 3.3 Hz, 4H), 2.96 (s, 1H), 1.99-1.90 (m, 4H); ¹³C NMR (150 MHz, CDCl₃) δ 141.24 (d, J=3.2 Hz), 133.10, 123.15 (d, J=2.6 Hz), 116.8, 83.6, 76.5, 49.5, 25.7; ¹⁹F NMR (376 MHz, CDCl₃) δ 47.7; ESI-MS (m/z): 253 [M+H]⁺.

Ex. 39: N-(4-Ethynylphenyl)piperidine-1-sulfonimidoyl Fluoride

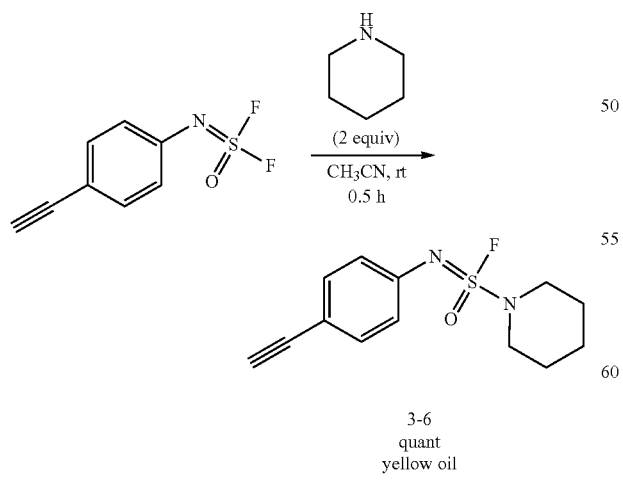

3-6
quant
yellow oil

Following the General Procedure III: The reaction of the iminosulfur oxydifluoride 2-4 (20.1 mg, 0.10 mmol) with piperidine (17.0 mg, 0.20 mmol) gave 3-6 (27.9 mg) as colorless oil. ¹H NMR (600 MHz, CDCl₃) δ 7.42-7.37 (m, 2H), 7.08-7.03 (m, 2H), 3.58-3.47 (m, 4H), 3.03 (s, 1H), 1.72 (dtt, J=8.6, 4.6, 2.2 Hz, 4H), 1.65-1.50 (m, 2H); ¹³C NMR (150 MHz, CDCl₃) δ 141.2 (d, J=2.1 Hz), 133.1, 123.1 (d, J=3.1 Hz), 116.8, 83.6, 76.6, 48.2, 24.8, 23.3; ¹⁹F NMR (376 MHz, CDCl₃) δ 50.1; ESI-MS (m/z): 267 [M+H]⁺.

Ex. 40: N-(4-Ethynylphenyl)-4-oxopiperidine-1-sulfonimidoyl Fluoride

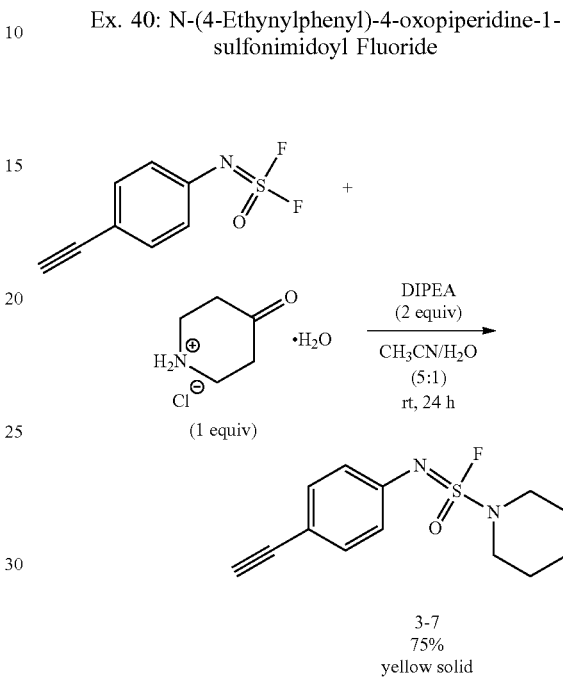

3-7
75%
yellow solid

Following the General Procedure III: The reaction of the iminosulfur oxydifluoride 2-4 (20.1 mg, 0.10 mmol) with 4-piperidone hydrochloride monohydrate (15.3 mg, 0.10 mmol) and DIPEA (25.9 mg, 35 µL, d=0.742 g/mL) in 1 mL of CH₃CN and 0.20 mL of H₂O gave 3-7 (21.0 mg, 75%) as a yellow solid after flash column chromatographic purification over silica gel (Hexanes/EA=2:1). Mp: 70° C.; ¹H NMR (600 MHz, CDCl₃) δ 7.45-7.40 (m, 2H), 7.11-7.04 (m, 2H), 3.97-3.88 (m, 4H), 3.05 (s, 1H), 2.65 (td, J=6.2, 3.3 Hz, 4H); ¹³C NMR (150 MHz, CDCl₃) δ 204.1, 140.3 (d, J=3.3 Hz), 133.3, 123.2 (d, J=2.8 Hz), 117.6, 83.3, 76.9, 46.7, 40.1; ¹⁹F NMR (376 MHz, CDCl₃) δ 56.6; ESI-MS (m/z): 281 [M+H]⁺.

Ex. 41: N-(4-Ethynylphenyl)morpholine-4-sulfonimidoyl Fluoride

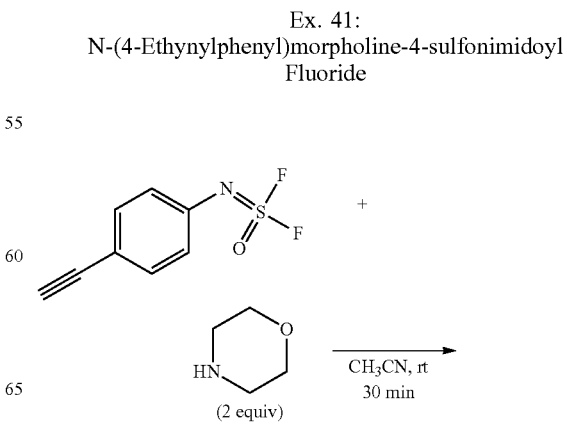

-continued

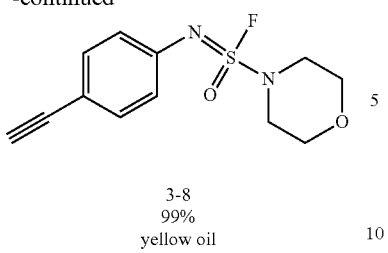

3-8
99%
yellow oil

Following the General Procedure III: the reaction of the iminosulfur oxydifluoride 2-4 (20.1 mg, 0.10 mmol) with piperidine (17.4 mg, 0.20 mmol) gave 3-8 (26.5 mg, 99%) as yellow oil. $^1$H NMR (600 MHz, CDCl$_3$) δ 7.43-7.38 (m, 2H), 7.08-7.02 (m, 2H), 3.86-3.76 (m, 4H), 3.60-3.47 (m, 4H), 3.04 (s, 1H); $^{13}$C NMR (150 MHz, CDCl$_3$) δ 140.4 (d, J=3.2 Hz), 133.2, 123.2 (d, J=3.1 Hz), 117.3, 83.4, 76.8, 65.7, 47.1; $^{19}$F NMR (376 MHz, CDCl$_3$) δ 48.1; ESI-MS (m/z): 269 [M+H]$^+$.

Ex. 42: N-(4-Ethynylphenyl)-4,6,6-trimethyl-2-azabicyclo[2.2.2]octane-2-sulfonimidoyl Fluoride

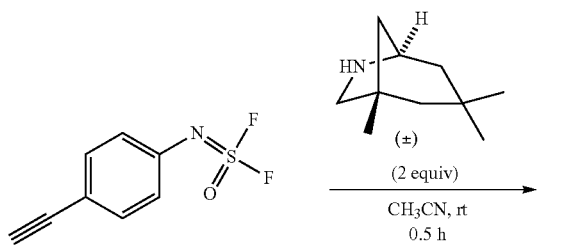

3-9
88%
colorless oil

Following the General Procedure III: The reaction of the iminosulfur oxydifluoride 2-4 (20.1 mg, 0.10 mmol) with the amine (30.6 mg, 0.20 mmol) gave of 3-9 (29.3 mg, 88%, d.r.=1.19:1). as colorless oil after column purification (hexanes/EA=4:1). $^1$H NMR (600 MHz, CDCl$_3$) δ 7.32 (dd, J=8.5, 2.6 Hz, 2H), 6.98 (dd, J=8.4, 4.0 Hz, 2H), 4.39-4.34 (m, 1H), 3.39 (m, 1H), 3.19 (dt, J=9.7, 2.5 Hz, 1H), 2.95 (d, J=1.5 Hz, 1H), 1.92-1.69 (m, 2H), 1.55-1.23 (m, 5H), 1.10 (d, J=13.0 Hz, 3H), 1.05 (d, J=4.6 Hz, 3H), 0.89 (s, 2H); $^{13}$C NMR (150 MHz, CDCl$_3$) δ 141.6, 133.1, 123.2, 116.6, 116.6, 83.7, 76.5, 65.8, 61.7, 60.1, 59.9, 58.3, 51.2, 43.8, 43.5, 43.1, 42.6, 40.7, 40.6, 36.3, 36.3, 31.6, 31.6, 29.9, 29.9, 24.7, 24.6; $^{19}$F NMR (376 MHz, CDCl$_3$) δ 53.0, 51.3; ESI-MS (m/z): 335 [M+H]$^+$.

Ex. 43: Methyl (N-(4-ethynylphenyl)-S-fluorosulfonimidoyl)-L-prolinate

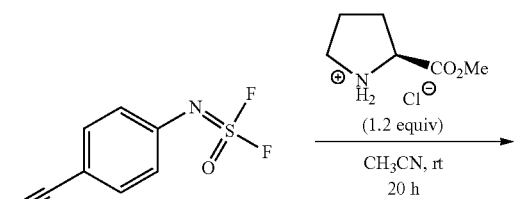

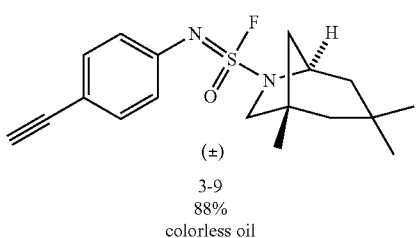

3-10
97%
colorless oil

Following the General Procedure III: The reaction of the iminosulfur oxydifluoride 2-4 (20.1 mg, 0.10 mmol) with methyl prolinate hydrochloride (20 mg, 0.12 mmol) gave 3-10 (30.0 mg, 97%, dr=1.24:1), as colorless oil after column chromatographic purification over silica gel (hexanes/EA=3:1). [α]$^{25}_D$=−55.8 (c=1.00, CHCl$_3$); $^1$H NMR (600 MHz, CDCl$_3$) δ 7.42-7.35 (m, 2H), 7.05 (d, J=8.6 Hz, 1H), 7.02-6.97 (m, 1H), 4.58 (dddd, J=19.2, 8.7, 3.6, 1.9 Hz, 1H), 3.77 (d, J=12.5 Hz, 4H), 3.69 (ddt, J=9.6, 6.9, 2.3 Hz, 1H), 3.03 (d, J=1.1 Hz, 1H), 2.42-2.29 (m, 1H), 2.23-2.01 (m, 3H); $^{13}$C NMR (150 MHz, CDCl$_3$) δ 171.3, 171.2, 140.7, 140.6 (d, J=2.8 Hz), 133.1, 133.1, 123.2 (d, J=2.2 Hz), 123.1 (d, J=2.5 Hz), 117.0, 83.5, 76.6, 62.5, 61.7, 52.7, 52.6, 50.2, 49.4, 30.9, 30.9, 24.7, 24.6; $^{19}$F NMR (376 MHz, CDCl$_3$) δ 55.0, 54.5; ESI-MS (m/z): 311 [M+H]$^+$.

Ex. 44: N-(((1R,4aS,10aR)-7-Isopropyl-1,4a-dimethyl-1,2,3,4,4a,9,10,10a-octahydrophenanthren-1-yl)methyl)piperidine-1-sulfonimidoyl Fluoride

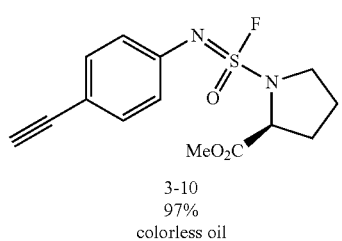

-continued

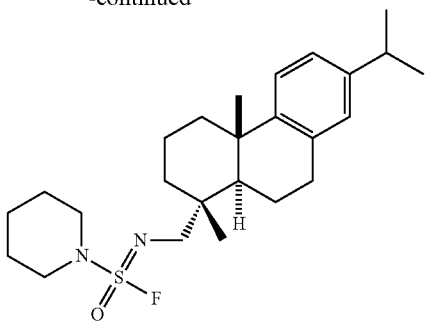

3-11
98%
colorless oil

Following the General Procedure III: The reaction of the iminosulfur oxydifluoride 2-18 (37.3 mg, 0.10 mmol) with morpholine (17.4 mg, 0.20 mmol) gave 3-11 (26.5 mg, 99%, d.r.=1:1) as colorless oil. $[\alpha]^{25}_D$=19.0 (c=1.00, CHCl$_3$); $^1$H NMR (600 MHz, CDCl$_3$) δ 7.22 (dd, J=8.2, 1.9 Hz, 1H), 7.03 (dt, J=8.2, 2.6 Hz, 1H), 6.92 (d, J=2.4 Hz, 1H), 3.67-2.75 (m, 8H), 2.37-2.19 (m, 1H), 1.94-1.34 (m, 15H), 1.32-1.19 (m, 9H), 0.95 (d, J=1.7 Hz, 3H); $^{13}$C NMR (150 MHz, CDCl$_3$) δ 147.5, 147.4, 145.3, 145.3, 135.1, 134.9, 126.8, 126.8, 124.4, 124.3, 123.7, 123.6, 54.8, 48.1, 48.0, 44.6, 44.2, 38.5, 38.4, 37.5, 37.5, 37.4, 35.8, 35.7, 33.4, 30.4, 30.3, 25.5, 25.4, 24.8, 24.7, 24.0, 23.9, 23.5, 18.8, 18.8, 18.72, 18.7, 18.6; $^{19}$F NMR (376 MHz, CDCl$_3$) δ 50.9, 50.2; HRMS (ESI-TOF) Calcd for C$_{25}$H$_{40}$FN$_2$OS$^+$[M+H]+: 435.2840; found: 435.2839.

Ex. 45: N-(3-((2-Oxo-2H-chromen-4-yl)oxy)propyl)piperidine-1-sulfonimidoyl Fluoride

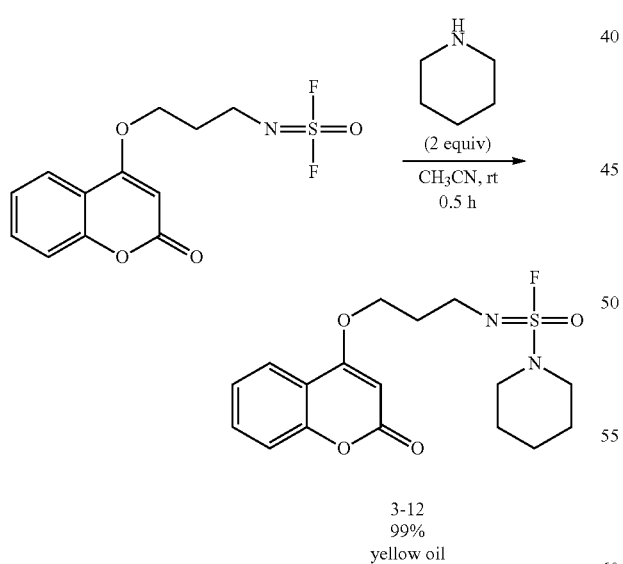

3-12
99%
yellow oil

Following the General Procedure III: the reaction of the iminosulfur oxydifluoride 2-9 (30.3 mg, 0.1 mmol) with piperidine (17.0 mg, 0.2 mmol) gave 3-12 (36.5 mg, 99%) as yellow oil. $^1$H NMR (400 MHz, CDCl$_3$) δ 7.83 (dd, J=7.9, 1.7 Hz, 1H), 7.63-7.46 (m, 1H), 7.35-7.23 (m, 2H), 5.71 (s, 1H), 4.26 (t, J=6.2 Hz, 2H), 3.56-3.48 (m, 1H), 3.40 (q, J=4.6 Hz, 4H), 2.17 (q, J=6.2 Hz, 2H), 1.68 (dq, J=9.0, 3.2, 2.7 Hz, 4H), 1.58 (q, J=5.6 Hz, 2H); $^{13}$C NMR (150 MHz, CDCl$_3$) δ 165.6, 163.0, 153.3, 132.3, 123.8, 122.9, 116.7, 115.7, 90.5, 66.5, 48.1, 40.3, 30.6, 24.8, 23.3; $^{19}$F NMR (376 MHz, CDCl$_3$) δ 49.8; ESI-MS (m/z): 369 [M+H]$^+$.

Ex. 46: N-((2S,3S,5R)-5-(5-Methyl-2,4-dioxo-3,4-dihydropyrimidin-1(2H)-yl)-2-((prop-2-yn-1-yloxy)methyl)tetrahydrofuran-3-yl)azetidine-1-sulfonimidoyl Fluoride

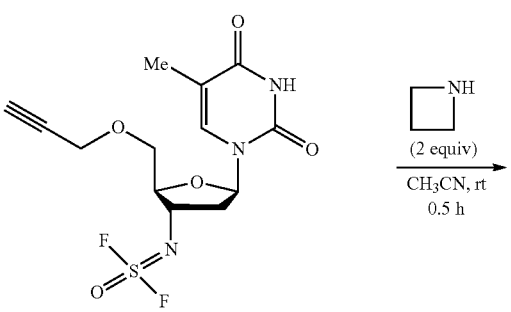

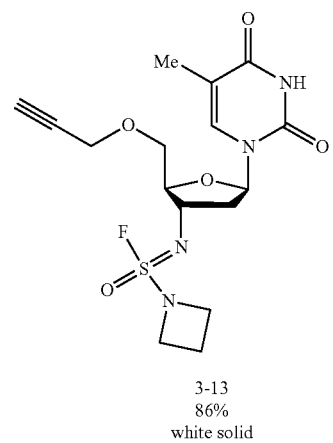

3-13
86%
white solid

Following the General Procedure III: The reaction of the iminosulfur oxydifluoride 2-23 (36.3 mg, 0.10 mmol) with azetidine (11.4 mg, 0.20 mmol) gave 3-13 (34.5 mg, 86%, d.r.=1.08:1) as white solid after flash column chromatographic purification over silica gel (hexanes/EA=1:1). Mp: 105-106° C.; $[\alpha]^{25}_D$=37.7 (c=1.00, CHCl$_3$); $^1$H NMR (600 MHz, CDCl$_3$) δ 9.06 (d, J=7.0 Hz, 1H), 7.68 (dd, J=11.6, 1.5 Hz, 1H), 6.26 (dd, J=6.5, 5.1 Hz, 1H), 4.30-4.18 (m, 3H), 4.18-4.07 (m, 4H), 3.98 (dq, J=5.6, 2.7 Hz, 1H), 3.90 (ddd, J=10.7, 4.9, 2.3 Hz, 1H), 3.71 (dt, J=10.7, 2.7 Hz, 1H), 2.49 (q, J=2.3 Hz, 1H), 2.38-2.19 (m, 4H), 1.95 (s, 3H); $^{13}$C NMR (150 MHz, CDCl$_3$) δ 163.9, 150.4, 150.3, 135.9, 110.6, 85.5, 85.4, 85.3, 84.8, 84.7, 78.9, 78.9, 75.2, 75.2, 68.4, 68.4, 58.6, 52.8, 52.6, 52.4, 40.8, 40.8, 15.3, 15.3, 12.6; $^{19}$F NMR (377 MHz, CDCl$_3$) δ 44.6, 42.6; ESI-MS (m/z): 401 [M+H]$^+$.

Ex. 47: 4-(2-Chlorodibenzo[b][1,4]oxazepin-11-yl)-N-(4-ethynylphenyl)piperazine-1-sulfonimidoyl Fluoride

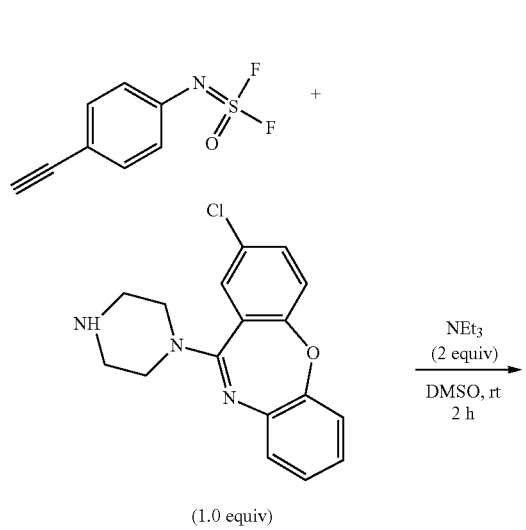

3-14
99%
yellow solid

Following the General Procedure III: the reaction of the iminosulfur oxydifluoride 2-4 (20.1 mg, 0.10 mmol) with amoxapine (31.3 mg, 0.10 mmol) and NEt$_3$ (28 kL, 0.20 mmol) gave 3-14 (48.8 mg, 99%) as yellow solid. Mp: 72-75° C.; $^1$H NMR (600 MHz, CDCl$_3$) δ 7.45-7.38 (m, 3H), 7.31 (d, J=2.6 Hz, 1H), 7.20 (d, J=8.6 Hz, 1H), 7.16 (dd, J=8.2, 1.7 Hz, 1H), 7.13-7.09 (m, 2H), 7.09-7.00 (m, 3H), 3.67 (s, 8H), 3.04 (s, 1H); $^{13}$C NMR (150 MHz, CDCl$_3$) δ 159.4, 158.3, 151.7, 140.5, 139.4, 133.2, 133.1, 130.6, 128.6, 127.1, 125.9, 125.4, 124.5, 123.2, 122.9, 120.2, 117.3, 83.4, 46.8, 46.5; $^{19}$F NMR (376 MHz, CDCl$_3$) δ 50.2; ESI-MS (m/z): 495 [M ($^{35}$Cl)+H]$^+$; 497 [M ($^{35}$Cl)+H]$^+$.

Ex. 48: The Reaction of Iminosulfur Oxydifluorides with Amino Acids

General Procedure IV: A 5 mL vial with a magnetic stir bar was charged with 1 mL of CH$_3$CN, 1 mL PBS buffer (pH=7.0), amino acid (0.5 M in H$_2$O, 0.4 mL), DIPEA (0.50 mmol), iminosulfur oxydifluoride (0.10 mmol) in order. The mixture was stirred at room temperature for 20 hours then diluted with ethyl acetate (10 mL). The solution was washed with cold aq. HCl (1 M, 10 mL), water and brine, then dried over anhydrous MgSO$_4$. After filtration, the solvent was removed under reduced pressure and rotary evaporation. The products obtained required no further purification.

Ex. 49: (N-(4-ethynylphenyl)sulfamoyl)glycine

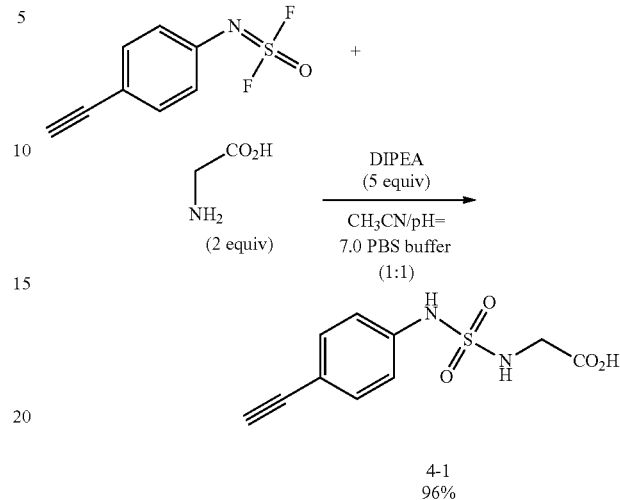

4-1
96%

Following the General Procedure IV: The reaction of the iminosulfur oxydifluoride 2-4 (20.1 mg, 0.1 mmol) with glycine (0.2 mmol) gave 4-1 (24.3 mg, 96%) as yellow solid. Mp: 113-115° C.; $^1$H NMR (600 MHz, CD$_3$CN) δ 7.85 (s, 1H), 7.44 (d, J=8.6 Hz, 2H), 7.16 (d, J=8.7 Hz, 2H), 5.97 (s, 1H), 3.73 (s, 2H), 3.34 (s, 1H); $^{13}$C NMR (150 MHz, CD$_3$CN) δ 170.8, 139.7, 133.9, 119.9, 117.9, 83.9, 78.4, 44.5; ESI-MS (m/z): 255 [M+H]$^+$.

Ex. 50: (N-(4-Ethynylphenyl)sulfamoyl)-L-alanine

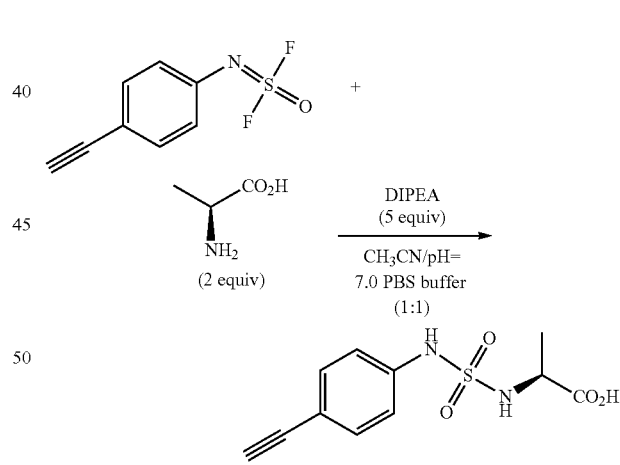

4-2
97%

Following the General Procedure IV: The reaction of the iminosulfur oxydifluoride 2-4 (20.1 mg, 0.10 mmol) with alanine (0.20 mmol) gave 4-2 (26.1 mg, 97%) as yellow solid. Mp: 163-165° C.; [α]$^{25}_D$=0.5 (c=1.00, MeOH); $^1$H NMR (400 MHz, CD$_3$CN) δ 7.88 (s, 1H), 7.49-7.42 (m, 2H), 7.21-7.12 (m, 2H), 6.12 (d, J=8.5 Hz, 1H), 3.99 (dq, J=8.6, 7.2 Hz, 1H), 1.28 (d, J=7.2 Hz, 3H); $^{13}$C NMR (150 MHz, CD$_3$CN) δ 173.8, 139.7, 133.9, 119.6, 117.7, 83.87, 78.4, 52.3, 18.9; ESI-MS (m/z): 269 [M+H]$^+$.

Ex. 51: (N-(4-Ethynylphenyl)sulfamoyl)-L-phenylalanine

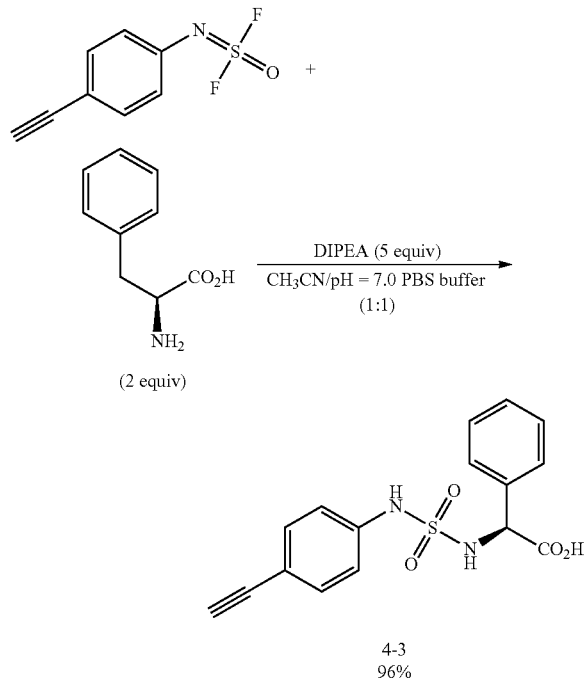

4-3
96%

Following the General Procedure IV: The reaction of the iminosulfur oxydifluoride 2-4 (20.1 mg, 0.10 mmol) with phenylalanine (0.20 mmol) gave 4-3 (33.0 mg, 96%) as yellow solid. Mp: 115-117° C.; $[\alpha]^{25}_D$=−21.3 (c=1.00, MeOH); $^1$H NMR (600 MHz, CD$_3$CN) δ 7.80 (s, 1H), 7.38-7.30 (m, 2H), 7.25-7.15 (m, 3H), 7.15-7.08 (m, 2H), 7.02-6.91 (m, 2H), 6.07 (d, J=9.2 Hz, 1H), 4.20-4.07 (m, 1H), 3.34 (s, 1H), 3.01 (dd, J=14.0, 5.6 Hz, 1H), 2.84 (dd, J=14.0, 8.2 Hz, 1H); $^{13}$C NMR (150 MHz, CD$_3$CN) δ 172.9, 139.5, 137.2, 133.8, 130.3, 129.3, 127.8, 119.4, 118.3, 117.6, 83.9, 78.3, 58.2, 38.9, 1.7, 1.6, 1.5, 1.3, 1.2, 1.2, 1.0, 0.9; ESI-MS (m/z): 345 [M+H]$^+$.

Ex. 52: The Reaction of Iminosulfur Oxydifluorides with Phenols

General Procedure V: A 3 mL vial with a magnetic stir bar was charged with iminosulfur oxydifluoride (0.10 mmol), ArOTBS (1 equiv), and 1 mL of CH$_3$CN. After all the starting materials dissolved, DBU or BEMP (5.00 μmol) was added. On completion of the reaction (TLC), the product was purified by flash column chromatography over silica gel.

Ex. 53: [1,1'-biphenyl]-4-yl (4-ethynylphenyl)sulfurofluoridoimidate

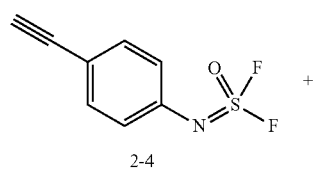

2-4

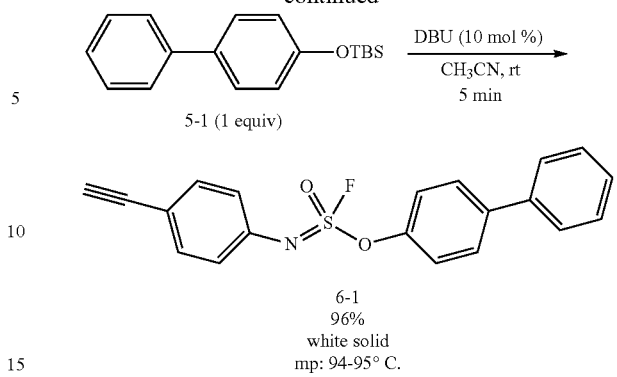

6-1
96%
white solid
mp: 94-95° C.

Following the General Procedure V: The reaction of the iminosulfur oxydifluoride 2-4 (50.3 mg, 0.25 mmol) with phenoxysilane (71 mg, 0.25 mmol) gave 6-1 (84.3 mg, 96%) as white solid. Mp: 94-95° C.; $^1$H NMR (600 MHz, CDCl$_3$) δ 7.51 (d, J=8.6 Hz, 2H), 7.44 (d, J=7.6 Hz, 2H), 7.38-7.32 (m, 4H), 7.28 (d, J=6.9 Hz, 3H), 7.02 (d, J=8.4 Hz, 2H), 2.97 (s, 1H); $^{13}$C NMR (150 MHz, CDCl$_3$) δ 149.4, 141.5, 139.3, 139.1 (d, J=3.5 Hz), 139.1, 133.3, 128.9, 128.77, 127.9, 127.1, 123.6 (d, J=3.5 Hz), 121.5, 118.6, 83.1, 77.4; $^{19}$F NMR (376 MHz, CDCl$_3$) δ 50.3; ESI-MS (m/z): 352 [M+H]$^+$.

Ex. 54: phenyl (3,4-dichlorophenyl)sulfurofluoridoimidate

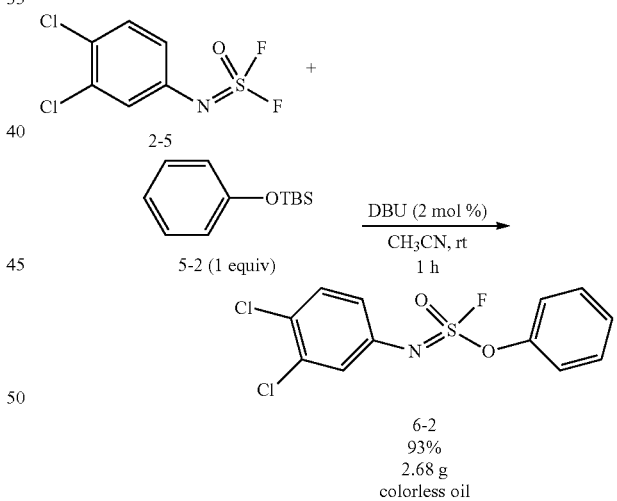

6-2
93%
2.68 g
colorless oil

Following the General Procedure V: the reaction of the iminosulfur oxydifluoride 2-5 (2.214 g, 9.00 mmol) with phenoxysilane (1.880 g, 9.00 mmol) in the presence of DBU (27.0 mg, 0.18 mmol) gave 6-2 (2.681 g, 93%) as colorless oil. $^1$H NMR (600 MHz, CDCl$_3$) δ 7.49-7.43 (m, 2H), 7.43-7.35 (m, 2H), 7.33 (dt, J=8.6, 1.1 Hz, 2H), 7.24 (d, J=2.5 Hz, 1H), 7.00 (dd, J=8.6, 2.5 Hz, 1H); $^{13}$C NMR (150 MHz, CDCl$_3$) δ 150.1, 130.8, 130.3, 128.7, 128.4, 125.6, 125.6, 123.2, 121.2; $^{19}$F NMR (376 MHz, CDCl$_3$) δ 49.4; ESI-MS (m/z): 320 [M ($^{35}$Cl, $^{35}$Cl)+H]$^+$; 322 [M ($^{35}$Cl, $^{37}$Cl)+H]$^+$.

Ex. 55: (8R,9S,13S)-13-Methyl-17-oxo-7,8,9,11,12,13,14,15,16,17-decahydro-6H-cyclopenta[a]phenanthren-3-yl ((2S,3S,5R)-5-(5-methyl-2,4-dioxo-3,4-dihydropyrimidin-1(2H)-yl)-2-((prop-2-yn-1-yloxy)methyl)tetrahydrofuran-3-yl)sulfurofluoridoimidate

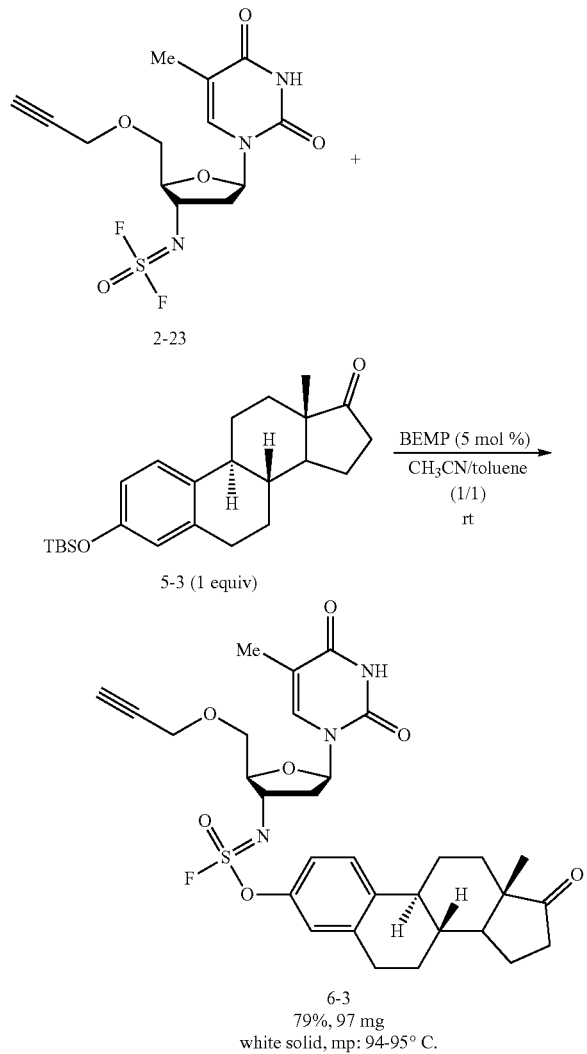

Following the General Procedure V: The reaction of the iminosulfur oxydifluoride 2-23 (73.0 mg, 0.20 mmol) with phenoxysilane (77.0 mg, 0.20 mmol) in the presence of BEMP (10.0 µL, 1 M/hexanes) gave 6-3 (97 mg, 79%, d.r.=1:1) as white solid. Mp: 94-95° C.; [α]$^{25}_D$=107.8 (c=1.00, CHCl$_3$); $^1$H NMR (600 MHz, CDCl$_3$) δ 9.55 (d, J=4.6 Hz, 1H), 7.69 (s, 1H), 7.35 (t, J=7.5 Hz, 1H), 7.13-7.04 (m, 2H), 6.25 (t, J=5.7 Hz, 1H), 4.34 (dd, J=15.7, 7.2 Hz, 1H), 4.25 (dt, J=11.2, 2.6 Hz, 2H), 4.07 (ddd, J=18.7, 5.7, 2.8 Hz, 1H), 3.92 (ddd, J=10.9, 4.6, 2.3 Hz, 1H), 3.79-3.69 (m, 1H), 2.95 (dt, J=8.6, 4.2 Hz, 2H), 2.56-2.25 (m, 6H), 2.21-1.88 (m, 8H), 1.68-1.44 (m, 6H), 0.92 (s, 3H); $^{13}$C NMR (150 MHz, CDCl$_3$) δ 220.3, 164.1, 150.3, 147.9, 139.9, 139.1, 135.8, 127.0, 126.9, 121.0, 120.9, 118.1, 118.1, 110.5, 84.8, 84.8, 84.8, 78.8, 78.7, 75.3, 75.3, 68.1, 67.9, 58.6, 54.1, 53.9, 50.2, 47.7, 43.9, 40.2, 40.2, 37.7, 35.7, 31.4, 29.3, 25.9, 25.6, 21.4, 13.7, 12.6; $^{19}$F NMR (376 MHz, CDCl$_3$) δ 51.0, 49.6; MS [M+H]$^+$614.

Ex. 56: 4'-(Prop-2-yn-1-yloxy)-[1,1'-biphenyl]-4-yl (3-((2-oxo-2H-chromen-4-yl)oxy)propyl)sulfurofluoridoimidate

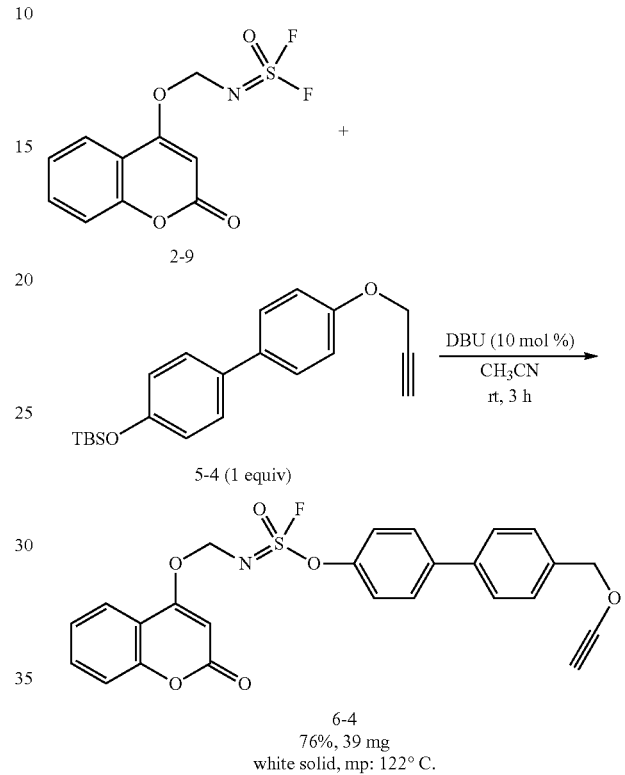

Following the General Procedure V: The reaction of the iminosulfur oxydifluoride 2-9 (30.3 mg, 0.10 mmol) with phenoxysilane (33.9 mg, 0.10 mmol) gave 6-4 (38.5 mg, 76%) as white solid. Mp: 122° C.; $^1$H NMR (600 MHz, CDCl$_3$) δ 7.81 (dd, J=7.9, 1.6 Hz, 1H), 7.57-7.50 (m, 3H), 7.50-7.43 (m, 2H), 7.35-7.21 (m, 4H), 7.10-7.01 (m, 2H), 5.69 (s, 1H), 4.74 (d, J=2.4 Hz, 2H), 4.25 (td, J=6.0, 1.4 Hz, 2H), 3.64 (td, J=6.2, 4.1 Hz, 2H), 2.55 (t, J=2.4 Hz, 1H), 2.20 (pd, J=6.0, 1.3 Hz, 2H); $^{13}$C NMR (150 MHz, CDCl$_3$) δ 165.4, 162.7, 157.5, 153.3, 149.1, 140.6, 132.7, 132.3, 128.2, 128.2, 123.8, 122.8, 121.4, 116.7, 115.6, 115.3, 90.6, 78.3, 75.7, 66.00, 55.8, 42.1, 29.9; $^{19}$F NMR (376 MHz, CDCl$_3$) δ 48.5; LC-MS [M+H]$^+$ 508.

Ex. 57: [1,1'-Biphenyl]-4-yl (4-(fluorosulfonyl)phenyl)sulfurofluoridoimidate

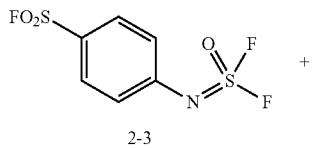

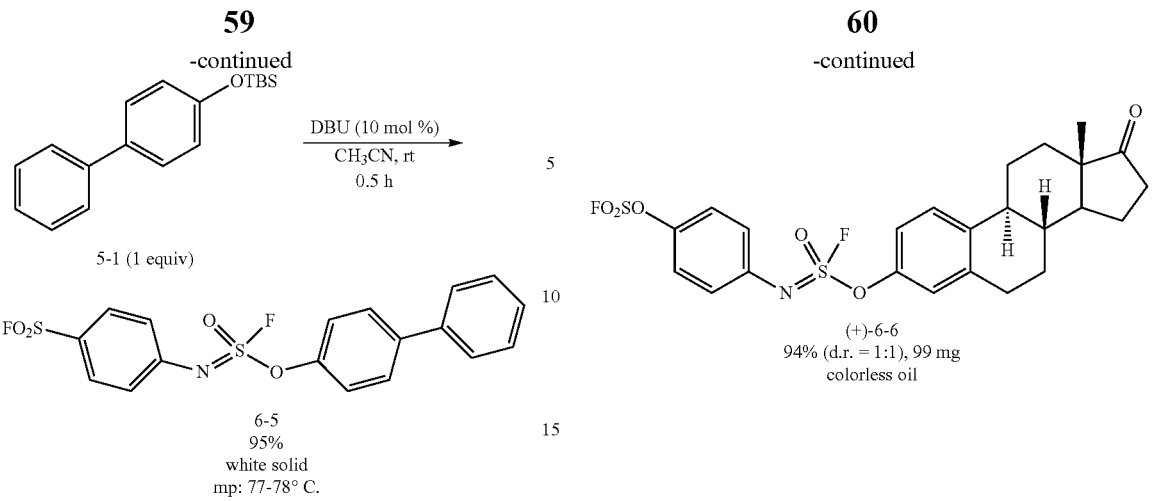

Following the General Procedure V: The reaction of the iminosulfur oxydifluoride 2-3 (27.5 mg, 0.10 mmol) with phenoxysilane (28.4 mg, 0.10 mmol) in the presence of DBU (10.0 μL, 1 M/CH$_3$CN, fresh prepared) gave 6-5 (39 mg, 95%) as white solid. Mp: 77-78° C.; $^1$H NMR (600 MHz, CDCl$_3$) δ 7.98 (d, J=8.5 Hz, 2H), 7.66 (d, J=8.4 Hz, 2H), 7.56 (d, J=7.7 Hz, 2H), 7.47 (t, J=7.5 Hz, 2H), 7.44-7.31 (m, 5H); $^{13}$C NMR (150 MHz, CDCl$_3$) δ 149.2, 145.9 (d, J=3.3 Hz), 141.9, 139.2, 130.1, 129.0, 128.9, 128.5 (d, J=25.3 Hz), 128.1, 127.2, 124.5 (d, J=2.6 Hz), 121.5; $^{19}$F NMR (376 MHz, CDCl$_3$) δ 66.2, 50.5; HRMS (ESI-TOF) Calcd for C$_{18}$H$_{14}$F$_2$NO$_4$S$_2$$^+$ [M+H]$^+$: 410.0327; found: 410.0326.

Ex. 58: 4-((Fluoro(((8R,9S,13S)-13-methyl-17-oxo-7,8,9,11,12,13,14,15,16,17-decahydro-6H-cyclopenta[a]phenanthren-3-yl)oxy)(oxo)-λ$^6$-sulfanylidene)amino)phenyl Sulfurofluoridate

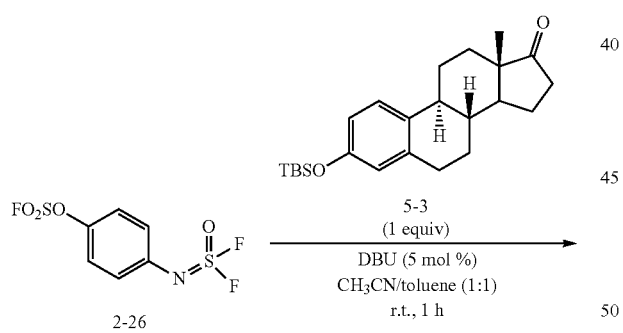

Following the General Procedure V: the reaction of the iminosulfur oxydifluoride 2-26 (55 mg, 0.2 mmol) with estrone silane 5-3 (77 mg, 0.2 mmol) gave 6-6 (98.9 mg, 94%, d.r.=1:1) as colorless oil. $[\alpha]^{25}_D$=70.4 (c=1.00, CHCl$_3$); $^1$H NMR (600 MHz, CDCl$_3$) δ 7.35 (d, J=8.7 Hz, 1H), 7.31-7.27 (m, 2H), 7.25-7.19 (m, 2H), 7.10 (dt, J=8.7, 2.7 Hz, 1H), 7.05 (d, J=2.6 Hz, 1H), 2.93 (dd, J=9.2, 4.3 Hz, 2H), 2.57-2.47 (m, 1H), 2.40 (dd, J=13.0, 4.2 Hz, 1H), 2.30 (d, J=4.2 Hz, 1H), 2.21-2.11 (m, 1H), 2.11-2.01 (m, 2H), 1.98 (dt, J=12.7, 2.8 Hz, 1H), 1.70-1.39 (m, 6H), 0.92 (s, 3H); $^{13}$C NMR (150 MHz, CDCl$_3$) δ 220.2, 147.9, 146.5, 140.3, 139.2, 139.2 (d, J=3.1 Hz), 127.1, 125.2 (d, J=3.2 Hz), 121.8, 120.9 (d, J=3.2 Hz), 118.1 (d, J=2.3 Hz), 50.3, 47.7, 44.0, 37.7, 35.7, 31.4, 29.3, 25.9, 25.6, 21.5, 13.7; $^{19}$F NMR (376 MHz, CDCl$_3$) δ 49.2, 49.1, 36.8; ESI-MS (m/z): 526 [M+H]$^+$.

Ex. 59: (8R,9S,13S)-13-Methyl-17-oxo-7,8,9,11,12,13,14,15,16,17-decahydro-6H-cyclopenta[a]phenanthren-3-yl (4-(((3-ethynylphenoxy)sulfonyl)oxy)phenyl)sulfurofluoridoimidate

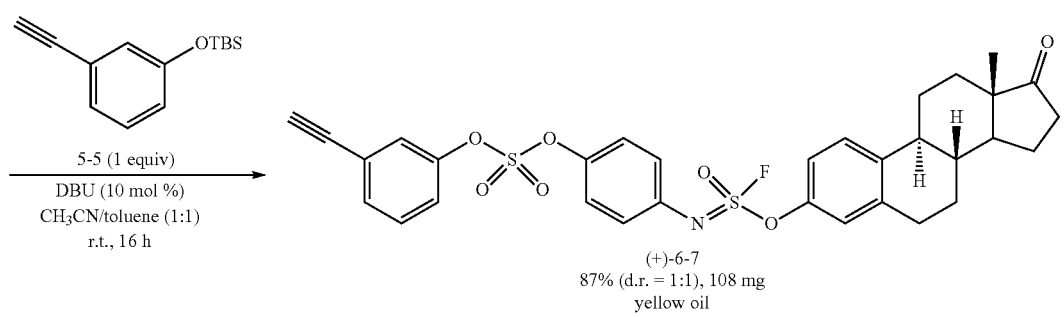

Following the General Procedure V: The reaction of the 6-6 (105 mg, 0.20 mmol) with silyl ether 5-5 (46.4 mg, 0.20 mmol) gave 6-7 (108.3 mg, 87%, d.r.=1:1) as yellow oil. $[\alpha]^{25}_D$=61.9 (c=1.00, CHCl$_3$); $^1$H NMR (600 MHz, CDCl$_3$) δ 7.49-7.42 (m, 2H), 7.39 (t, J=8.0 Hz, 1H), 7.36-7.30 (m, 2H), 7.29-7.24 (m, 2H), 7.22-7.16 (m, 2H), 7.09 (dt, J=8.7, 2.9 Hz, 1H), 7.04 (d, J=2.5 Hz, 1H), 3.16 (s, 1H), 2.98-2.87 (m, 2H), 2.56-2.46 (m, 1H), 2.39 (dd, J=12.8, 4.2 Hz, 1H), 2.29 (d, J=4.2 Hz, 1H), 2.14 (dd, J=19.1, 9.0 Hz, 1H), 2.05 (dddd, J=10.6, 8.3, 5.6, 4.3 Hz, 2H), 2.00-1.94 (m, 1H), 1.68-1.38 (m, 6H), 0.91 (s, 3H); $^{13}$C NMR (150 MHz, CDCl$_3$) δ 220.4, 149.9, 148.0, 146.9, 140.2, 139.2, 131.3, 130.0, 127.1, 125.0, 125.0, 124.5, 124.3, 122.0, 121.6, 121.0 (d, J=4.0 Hz), 118.2 (d, J=3.3 Hz), 81.7, 79.2, 50.3, 47.8, 44.0, 37.7, 35.7, 31.4, 29.3, 26.0, 25.6, 21.5, 13.7; $^{19}$F NMR (376 MHz, CDCl$_3$) δ 49.0, 49.0; ESI-MS (m/z): 624 [M+H]$^+$.

Connections of Primary Amines with Two Phenols or One Phenol and One Secondary Amine

Ex. 60: [1,1'-Biphenyl]-4-yl phenyl (3,4-dichlorophenyl)sulfurimidate

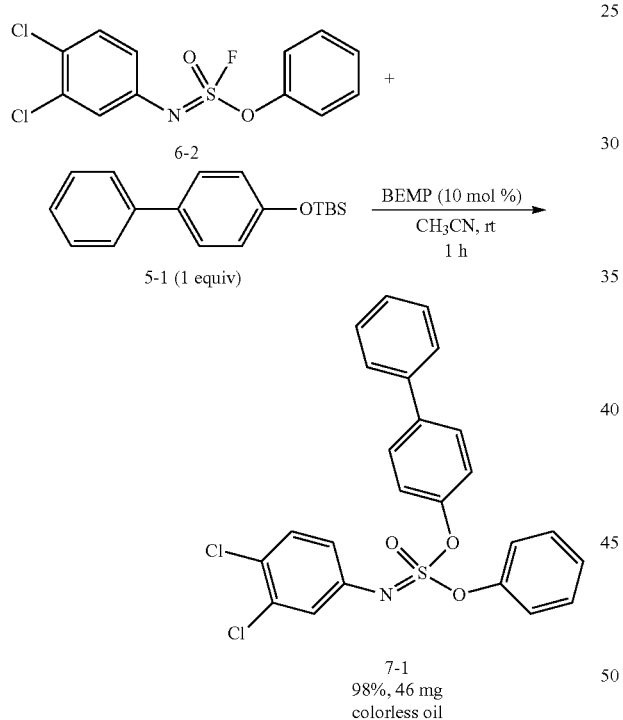

7-1
98%, 46 mg
colorless oil

To a 3 mL vial charged with a magnetic stir bar was added the sulfurofluoridoimidate 6-2 (32 mg, 0.10 mmol), ArOTBS 5-1 (28 mg, 0.10 mmol), and 1 mL of CH$_3$CN. After all the starting materials were dissolved, BEMP (10.0 μL, 1 M/hexanes) was added. After the completion of the reaction (TLC), the product was purified by flash column chromatography over silica gel to give 7-1 (46 mg, 98%) as colorless oil. $^1$H NMR (600 MHz, CDCl$_3$) δ 7.62-7.57 (m, 2H), 7.54 (d, J=7.4 Hz, 2H), 7.46-7.29 (m, 10H), 7.25 (d, J=2.6 Hz, 1H), 7.00 (dd, J=8.6, 2.6 Hz, 1H), 0.09 (s, 1H); $^{13}$C NMR (150 MHz, CDCl$_3$) δ 150.2, 149.5, 140.8, 140.6, 139.6, 132.6, 130.6, 129.9, 128.9, 128.6, 127.8, 127.6, 127.2, 127.1, 125.3, 123.0, 121.9, 121.7; ESI-MS (m/z): 470 [M ($^{35}$Cl, $^{35}$Cl)+H]$^+$, 472 [M ($^{37}$Cl, $^{35}$Cl)+H]$^+$.

Ex. 61: Di([1,1'-biphenyl]-4-yl) (4-ethynylphenyl)sulfurimidate

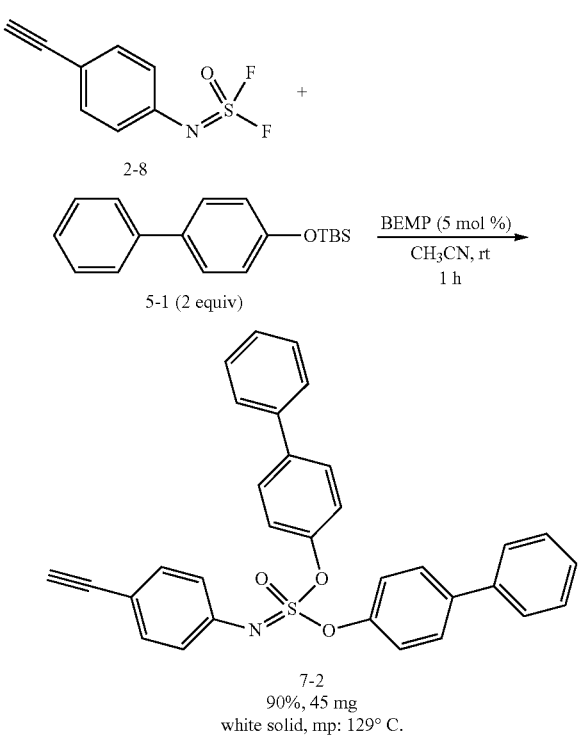

7-2
90%, 45 mg
white solid, mp: 129° C.

A 3 mL vial with a magnetic stir bar was charged with iminosulfur oxydifluoride 2-4 (20.1 mg, 0.10 mmol), ArOTBS 5-1 (57 mg, 0.10 mmol), and 1 mL of CH$_3$CN. After all the starting materials dissolved, BEMP (5.00 μL, 1 M/hexanes) was added. After the completion of the reaction (TLC), the product was purified by flash column chromatography over silica gel (hexanes/EA=10:1) to give 7-2 (45 mg, 90%) as white solid. Mp: 129° C.; $^1$H NMR (600 MHz, CDCl$_3$) δ 7.62-7.57 (m, 4H), 7.57-7.51 (m, 4H), 7.46-7.40 (m, 6H), 7.40-7.33 (m, 6H), 7.18-7.13 (m, 2H), 3.05 (s, 1H); $^{13}$C NMR (150 MHz, CDCl$_3$) δ 149.6, 149.6, 141.6, 140.7, 140.7, 139.7, 133.2, 128.9, 128.6, 127.7, 127.1, 127.1, 123.4, 122.0, 117.2, 83.5, 76.8; ESI-MS (m/z): 502 [M+H]$^+$.

Ex. 62: Phenyl N-(3,4-dichlorophenyl)pyrrolidine-1-sulfonimidate

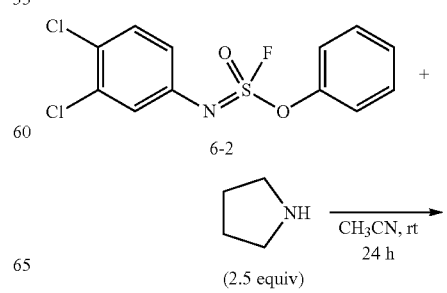

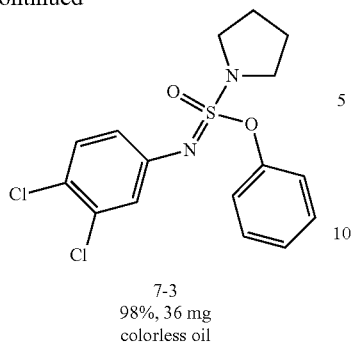

7-3
98%, 36 mg
colorless oil

A 3 mL vial with a magnetic stir bar was charged with sulfurofluoridoimidate 6-2 (32 mg, 0.10 mmol), 1 mL of CH₃CN, and pyrrolidine (17.8 mg, 0.25 mmol) and the reaction mixture stirred at room temperature. After the completion of the reaction (TLC), the product was purified by flash column chromatography over silica gel (hexanes/EA=10:1) to give 7-3 (36.2 mg, 98%) as colorless oil. $^1$H NMR (600 MHz, CDCl₃) δ 7.40-7.34 (m, 2H), 7.30-7.22 (m, 4H), 7.17 (d, J=2.5 Hz, 1H), 6.92 (dd, J=8.6, 2.5 Hz, 1H), 3.44 (t, J=5.5 Hz, 4H), 1.73-1.54 (m, 6H); $^{13}$C NMR (150 MHz, CDCl₃) δ 150.5, 142.9, 132.3, 130.3, 130.3, 129.6, 126.7, 125.5, 124.9, 122.7, 122.05, 48.2, 25.1, 23.5; ESI-MS (m/z): 371 [M ($^{35}$Cl, $^{35}$Cl)+H]⁺, 373 [M ($^{37}$Cl, $^{35}$Cl)+H]⁺.

Ex. 63: Phenyl N-(3,4-dichlorophenyl)morpholine-4-sulfonimidate

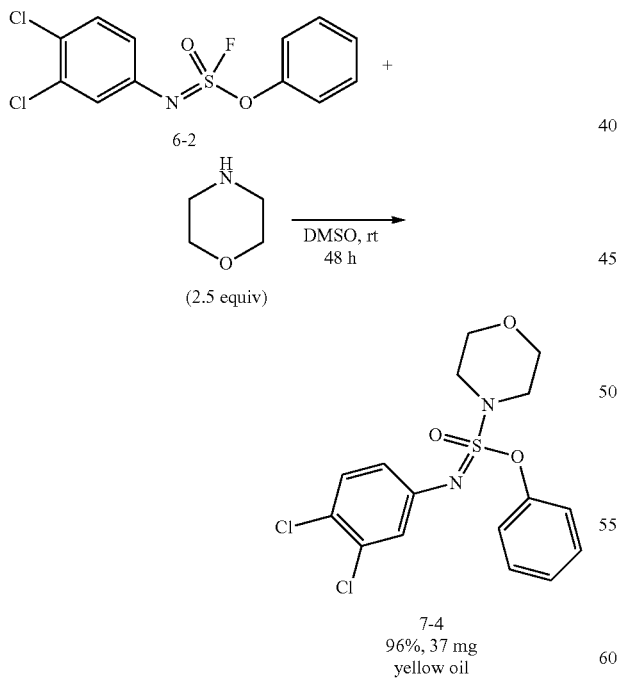

A 3 mL vial with a magnetic stir bar was charged with sulfurofluoridoimidate 6-2 (32 mg, 0.10 mmol), 1 mL of DMSO, and morpholine (21.8 mg, 0.25 mmol) and the reaction mixture was stirred at room temperature. After the completion of the reaction (TLC) (48 hours), the product was purified by flash column chromatography over silica gel (hexanes/EA=5:1) to give 7-4 (37.0 mg, 96%) as yellow oil. $^1$H NMR (600 MHz, CDCl₃) δ 7.43-7.35 (m, 2H), 7.31-7.23 (m, 4H), 7.16 (d, J=2.5 Hz, 1H), 6.90 (dd, J=8.6, 2.5 Hz, 1H), 3.77 (q, J=4.6 Hz, 4H), 3.48 (t, J=4.8 Hz, 4H); $^{13}$C NMR (150 MHz, CDCl₃) δ 150.2, 142.3, 132.4, 130.4, 129.7, 126.9, 125.9, 124.9, 122.6, 121.9, 66.0, 65.9, 47.3, 47.3; ESI-MS (m/z): 320 [M ($^{35}$Cl, $^{35}$Cl)+H]⁺; 322 [M ($^{35}$Cl, $^{37}$Cl)+H]⁺.

Ex. 64: Phenyl N-(3,4-dichlorophenyl)piperidine-1-sulfonimidate

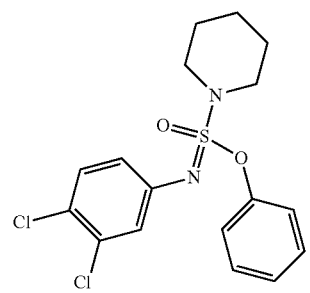 [SMILES: O=S(=Nc1ccc(Cl)c(Cl)c1)(Oc1ccccc1)N1CCCCC1]

Following a similar procedure as used with 7-3 and 7-4 above using piperidine in place of pyrrolidine or morpholine, phenyl N-(3,4-dichlorophenyl)piperidine-1-sulfonimidate was obtained. $^1$H NMR (600 MHz, Chloroform-d) δ 7.40-7.34 (m, 2H), 7.30-7.22 (m, 4H), 7.17 (d, J=2.5 Hz, 1H), 6.92 (dd, J=8.6, 2.5 Hz, 1H), 3.44 (t, J=5.5 Hz, 4H), 1.73-1.54 (m, 6H); $^{13}$C NMR (151 MHz, CDCl₃) δ 150.47, 142.91, 132.28, 130.29, 130.28, 129.60, 126.67, 125.48, 124.87, 122.65, 122.05, 48.20, 25.11, 23.54.

Ex. 65: The Reaction of Iminosulfur Oxydifluorides with Catechols

General Procedure VI: A 3 mL vial with a magnetic stir bar was charged with iminosulfur oxydifluoride 2-4 (0.10 mmol), silyl ether (0.10 mmol, 1 equiv), and 1 mL of CH₃CN. After all the starting materials dissolved, DBU (5.00 μmol) was added. After the completion of the reaction (TLC), the product was purified by flash column chromatography over silica gel.

Ex. 66: 2-((4-Ethynylphenyl)imino)-2λ⁴-benzo[d][1,3,2]dioxathiole 2-oxide

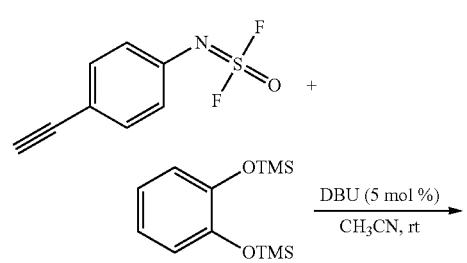

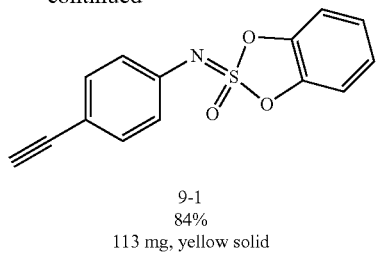

9-1
84%
113 mg, yellow solid

Following the General Procedure VI: the reaction of the iminosulfur oxydifluoride 2-4 (100 mg, 0.50 mmol) with silyl ether (254 mg, 0.50 mmol) in the presence of DBU (3.80 mg, 25 μmol) gave 9-1 (113 mg, 84%) as yellow solid. Mp: 97-98° C.; $^1$H NMR (400 MHz, CDCl$_3$) δ 7.39 (d, J=8.3 Hz, 2H), 7.15 (s, 4H), 7.07 (d, J=8.3 Hz, 2H), 3.03 (s, 1H); $^{13}$C NMR (150 MHz, CDCl$_3$) δ 143.2, 139.7, 133.2, 124.8, 124.1, 118.8, 111.7, 111.7, 82.9, 77.4; ESI-MS (m/z): 272 [M+H]$^+$.

Ex. 67: 2-((4-Ethynylphenyl)imino)-4,7-dimethyl-2λ$^4$-benzo[d][1,3,2]dioxathiole 2-oxide

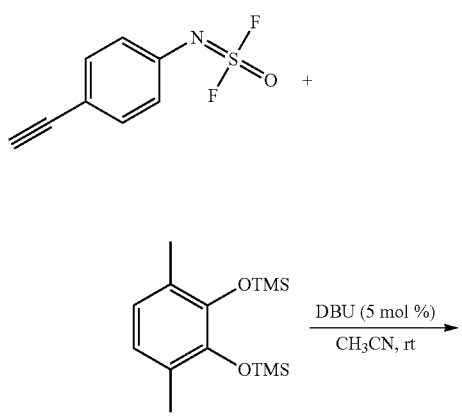

9-2
96%
28.7 mg, yellow solid

Following the General Procedure VI: the reaction of the iminosulfur oxydifluoride 2-4 (20 mg, 0.10 mmol) with silyl ether (25 mg, 0.10 mmol) in the presence of DBU (5.00 μL, 1 M/CH$_3$CN, fresh prepared) gave 9-2 (28.7 mg, 96%) as white solid. Mp: 101° C.; $^1$H NMR (600 MHz, CDCl$_3$) δ 7.39 (d, J=8.4 Hz, 2H), 7.06 (d, J=8.4 Hz, 2H), 6.84 (s, 2H), 3.03 (s, 1H), 2.27 (s, 6H); $^{13}$C NMR (150 MHz, CDCl$_3$) δ 141.7, 140.1, 133.2, 125.8, 125.8, 124.0, 119.4, 118.5, 83.1, 77.3, 14.6; ESI-MS (m/z): 300 [M+H]$^+$.

Ex. 68: Ethyl (E)-3-(2-((4-ethynylphenyl)imino)-2-oxido-2λ$^4$-benzo[d][1,3,2]dioxathiol-5-yl)acrylate

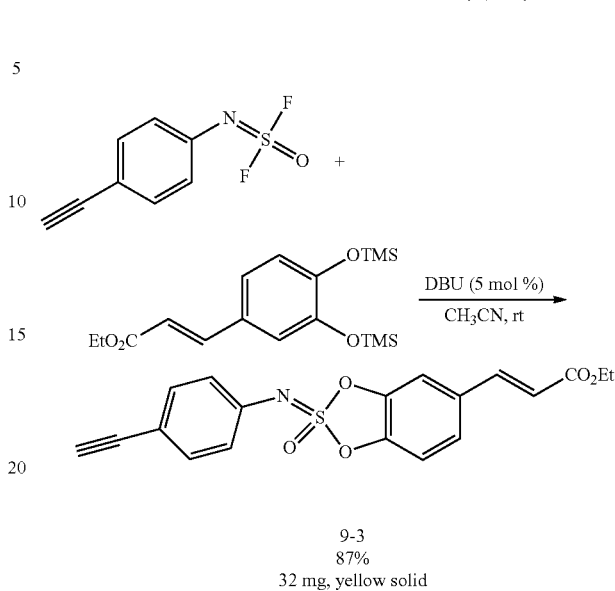

9-3
87%
32 mg, yellow solid

Following the General Procedure VI: The reaction of the iminosulfur oxydifluoride 2-4 (20.1 mg, 0.10 mmol) with silyl ether (35.3 mg, 0.10 mmol) in the presence of DBU (5.00 L, 1 M/CH$_3$CN, fresh prepared) gave 9-3 (32.0 mg, 87%) as yellow solid. Mp: 72-73° C.; $^1$H NMR (600 MHz, CDCl$_3$) δ 7.58 (d, J=16.0 Hz, 1H), 7.42-7.37 (m, 2H), 7.32 (d, J=1.8 Hz, 1H), 7.31-7.25 (m, 1H), 7.16 (d, J=8.4 Hz, 1H), 7.09-7.04 (m, 2H), 6.35 (d, J=16.0 Hz, 1H), 4.27 (q, J=7.1 Hz, 2H), 3.04 (s, 1H), 1.34 (t, J=7.1 Hz, 3H); $^{13}$C NMR (150 MHz, CDCl$_3$) δ 166.3, 143.9, 143.5, 142.2, 139.2, 133.3, 131.9, 125.4, 124.1, 119.8, 119.0, 111.9, 111.9, 111.9, 110.0, 109.9, 82.9, 77.5, 60.8, 14.3; ESI-MS (m/z): 370 [M+H]$^+$.

Ex. 69: 6-((4-Ethynylphenyl)imino)-6λ$^4$-dibenzo[d,f][1,3,2]dioxathiepine 6-oxide

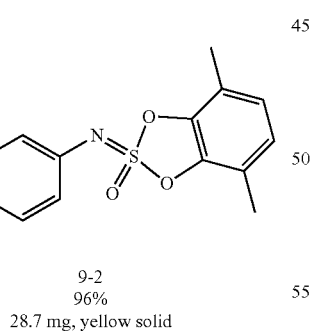

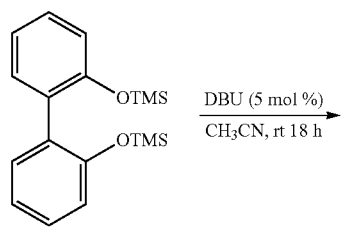

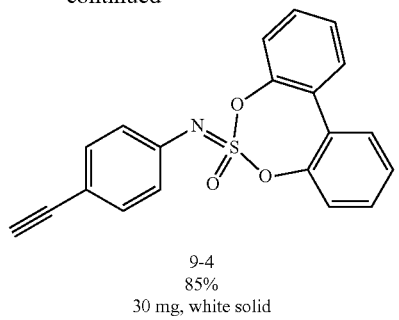

9-4
85%
30 mg, white solid

Following the General Procedure VI: The reaction of the iminosulfur oxydifluoride 2-4 (20.1 mg, 0.10 mmol) with silyl ether (33.0 mg, 0.10 mmol) in the presence of DBU (5.00 L, 1 M/CH$_3$CN, fresh prepared) gave 9-4 (29.7 mg, 87%) as white solid. Mp: 138-139° C.; $^1$H NMR (600 MHz, CDCl$_3$) δ 7.59-7.54 (m, 2H), 7.44-7.37 (m, 4H), 7.33-7.26 (m, 4H), 7.01 (d, J=8.5 Hz, 2H), 2.96 (s, 1H); $^{13}$C NMR (150 MHz, CDCl$_3$) δ 148.2, 141.2, 133.0, 130.3, 129.2, 129.0, 128.2, 123.6, 122.5, 122.5, 117.1, 83.5, 76.7; ESI-MS (m/z): 348 [M+H]$^+$.

Ex. 70: 2-Hydroxyphenyl N-(4-ethynylphenyl)piperidine-1-sulfonimidate

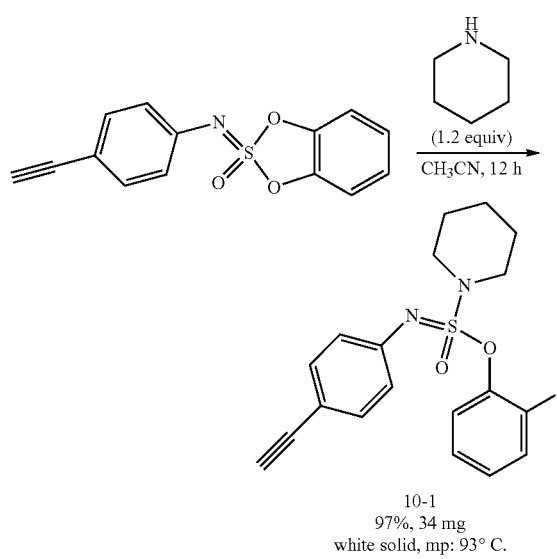

10-1
97%, 34 mg
white solid, mp: 93° C.

General Procedure VII: A vial (3.00 mL) with a magnetic stir bar was charged with the cyclic imidosulfates 9-1 (27.1 mg, 0.10 mmol), 1 mL of CH$_3$CN, and piperidine (10.2 mg, 0.12 mmol). The reaction was stirred at room temperature and monitored with TLC. After the completion of the reaction, the product was purified by flash column chromatography over silica gel (hexanes/EA=10:1) to give 10-1 (34.0 mg, 97%) as white solid. Mp: 93° C.; $^1$H NMR (600 MHz, CDCl$_3$) δ 9.41 (s, 1H), 7.37 (s, 2H), 7.19 (td, J=7.8, 1.6 Hz, 1H), 7.13 (dd, J=8.1, 1.6 Hz, 1H), 7.06 (dd, J=8.1, 1.6 Hz, 1H), 7.03-6.97 (m, 2H), 6.88 (td, J=7.8, 1.6 Hz, 1H), 3.52 (td, J=7.1, 4.1 Hz, 4H), 3.01 (s, 1H), 1.72-1.56 (m, 4H); $^{13}$C NMR (150 MHz, CDCl$_3$) δ 149.6, 142.6, 138.3, 133.1, 128.7, 123.9, 122.2, 120.6, 119.8, 116.2, 83.6, 76.5, 48.5, 25.0, 23.40; ESI-MS (m/z): 356 [M+H]$^+$.

Ex. 71: tert-Butyl 4-(N-(4-ethynylphenyl)-S-(2-hydroxyphenoxy)sulfonimidoyl)piperazine-1-carboxylate

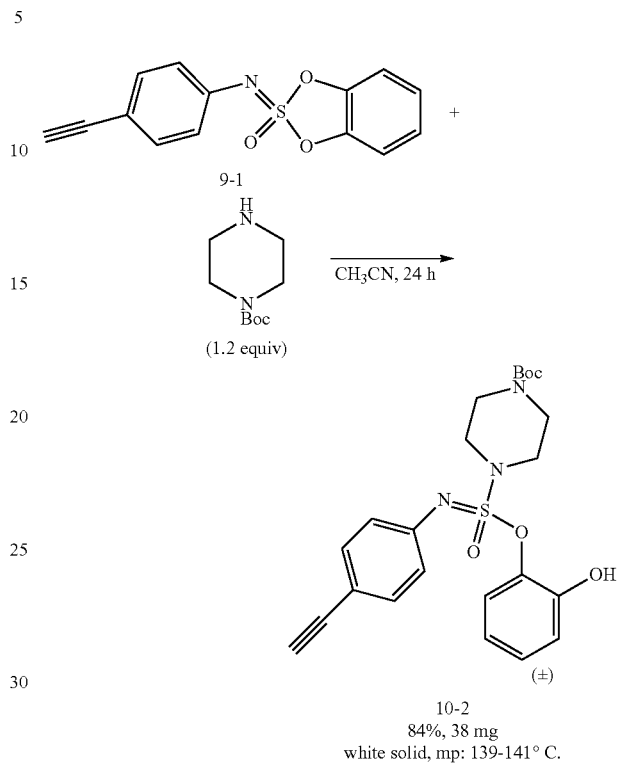

10-2
84%, 38 mg
white solid, mp: 139-141° C.

Following the General Procedure VII: The reaction of 9-1 (27.0 g, 0.10 mmol), 1-Boc-piperazine (22.4 mg, 0.12 mmol) in acetonitrile (1 mL) gave 10-2 (38.0 mg, 84%) as white solid. Mp: 139-141° C.; $^1$H NMR (600 MHz, CDCl$_3$) δ 9.06 (s, 1H), 7.45-7.32 (m, 2H), 7.20 (ddd, J=8.1, 7.4, 1.6 Hz, 1H), 7.13 (dd, J=8.1, 1.6 Hz, 1H), 7.07 (dd, J=8.2, 1.6 Hz, 1H), 7.04-6.96 (m, 2H), 6.90 (ddd, J=8.1, 7.4, 1.6 Hz, 1H), 3.53 (td, J=9.4, 8.8, 4.1 Hz, 8H), 3.03 (s, 1H), 1.46 (s, 9H); $^{13}$C NMR (150 MHz, CDCl$_3$) δ 154.2, 149.4, 141.9, 138.0, 133.2, 129.0, 123.8, 122.4, 120.8, 119.8, 116.8, 83.40, 80.7, 77.2, 77.0, 76.8, 76.7, 47.3, 28.3; ESI-MS (m/z): 458 [M+H]$^+$.

Ex. 72: General Procedure for Making the Polymer

A vial (60 mL) with magnetic stir bar was charged with the difluoride (5 mmol), bisphenol-TBS (5 mmol) and 10 mL of anhydrous NMP. The vial was sealed with a SUBA-SEAL® Septum and the atmosphere evacuated with a needle linked with a pump until there were no bubbles formed in the solution (5-10 minutes). Then DBU (0.15 mmol, d=1.018 g/mL) was added into the vial via a needle. After stirring at room temperature for 15 minutes, the solution thickened and the stir bar stopped stirring. After staying at room temperature for 3.5 hours, 10 mL of DMF was added while shaking the flask to promote the dissolution. The resulting solution was poured into 150 mL of MeOH slowly with mechanical stir. The solution was stirring in MeOH for 20 minutes and then filtered. The white solid was washed with MeOH three times (50 mL×3) and dried in the vacuum oven (60° C.) for 24 hours to give the polymer.

Ex. 73: Polymer Synthesis Based on the Iminosulfur Oxydifluoride

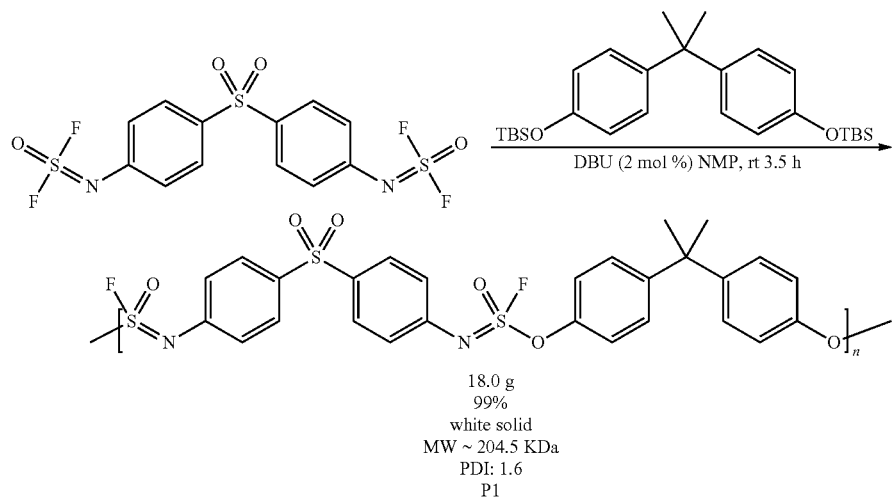

A round-bottom flask (250 mL) with magnetic stir bar was charged with the difluoride (12.49 g, 30 mmol), BPA-TBS (13.70 g, 30 mmol) and 40 mL of anhydrous NMP. The flask was sealed with a SUBA-SEAL® Septum and the atmosphere evacuated with a needle linked with a pump until there were no bubbles formed in the solution (5-10 minutes). Then DBU (91.3 mg, 90 jL, 0.6 mmol, d=1.018 g/mL) was added into the flask via a needle. After stirring at room temperature for 15 minutes, the solution thickened and the stir bar stopped stirring. After staying at room temperature for 3 hours, 50 mL of DMF was added while shaking the flask to promote the dissolution. The resulting solution was poured into 600 mL of MeOH slowly with mechanical stir. The solution was stirred in MeOH for 20 minutes and then filtered. The white solid was washed with MeOH three times (150 mL×3) and dried in the vacuum oven (60° C.) for 24 hours to give 18.0 g of the polymer P1 (99%). TGA: 261.18° C.; DSC: 150.78° C. $^1$H NMR (600 MHz, DMF-$d_7$) δ 8.23 (d, J=8.7 Hz, 4H), 7.63 (m, 12H), 1.88 (s, 6H); $^{13}$C NMR (151 MHz, DMF) δ 150.54, 147.94, 143.03, 137.79, 129.20, 128.75, 124.32, 120.90, 118.23, 116.03, 42.51, 29.74; $^{19}$F NMR (376 MHz, DMF-$d_7$) δ 50.68;

The polymerization works well for the substrates derived from both meta and para dibenzylamines, although in a low rate and the reaction time is 24 hours.

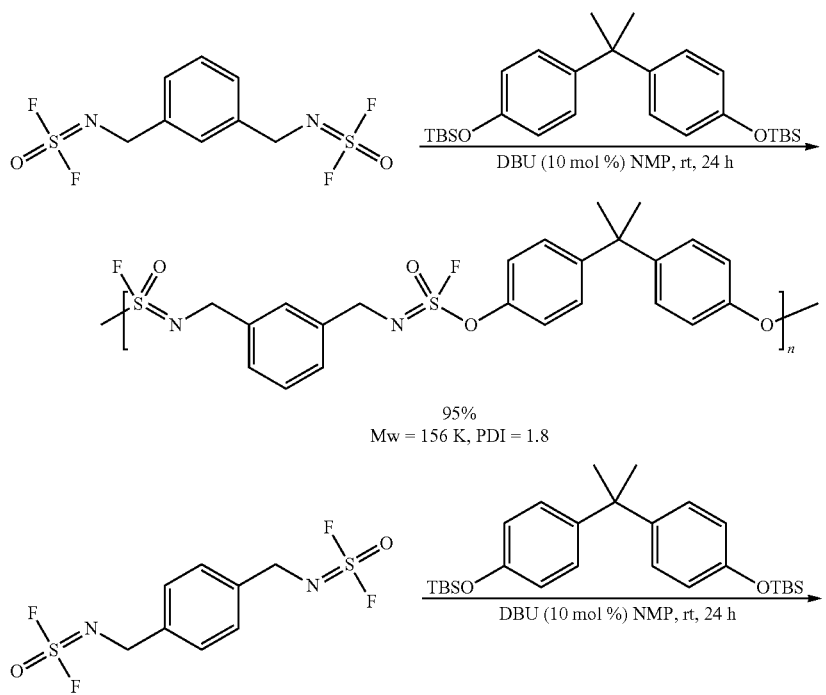

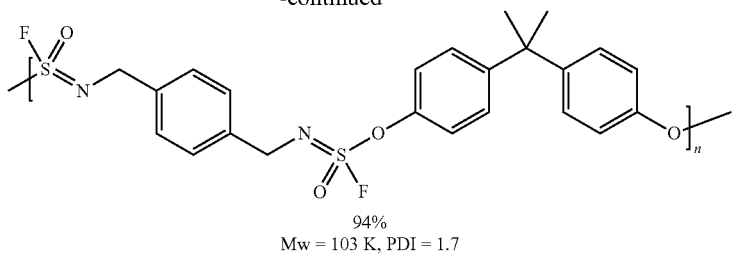

94%
Mw = 103 K, PDI = 1.7

Ex. 74: Derivatization of Polymer with Ethynyl Phenyl Substituent

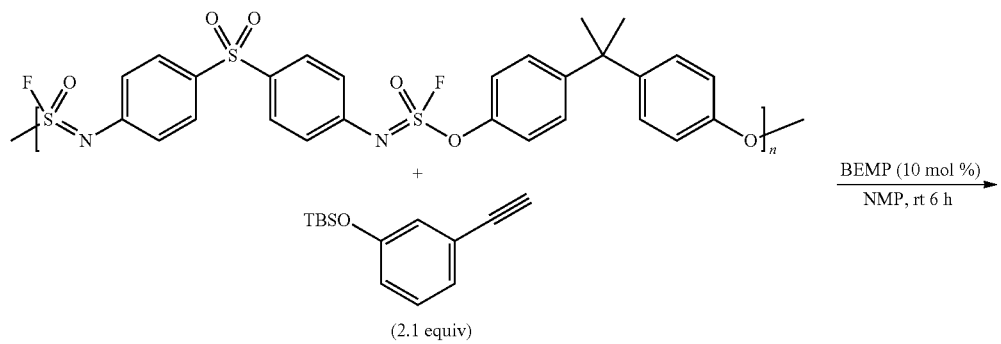

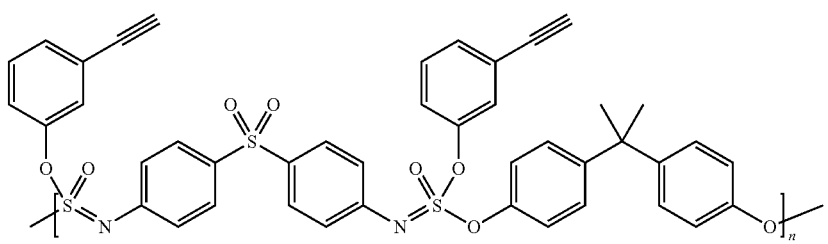

~ 93% of the S—F was substitued based on the ratio of hydrogen in methyl Vs. teminal alkyne the $^1$H NMR.
No F signal in $^{19}$F NMR.
P2

To a vial (50 mL) with a magnetic stir bar was added the polymer (604 mg, 1 mmol), ArOTBS (511 mg, 2.2 mmol), and 10 mL of anhydrous NMP. The flask was sealed with a SUBA-SEAL® Septum, the atmosphere evacuated with a needle linked with a pump until there were no bubbles formed in the solution (5-10 minutes). Then BEMP (0.1 mL, 1M) was added into the vial via a needle. After stirring at room temperature for 9 hours, the resulting solution was poured into 150 mL of MeOH slowly with stirring. The polymer was filtered. The white solid was washed with MeOH three times (10 mL×3) and dried in the vacuum oven (60° C.) for 24 hours to give 742 mg of the polymer P2 (93%) as white solid. $^1$H NMR (600 MHz, DMF-$d_7$) δ 8.19-8.13 (m, 4H), 7.79-7.68 (m, 8H), 7.63-7.51 (m, 12H), 4.49 (s, 2H), 1.85 (s, 6H); $^{13}$C NMR (151 MHz, DMF) δ 149.81, 131.24, 130.62, 128.94, 128.45, 124.58, 123.96, 123.78, 122.27, 121.06, 81.50, 81.37, 42.38, 29.82.

Ex. 75: Click Derivatization of Ethynyl Phenyl Substituted Polymer a CuAAC Reaction

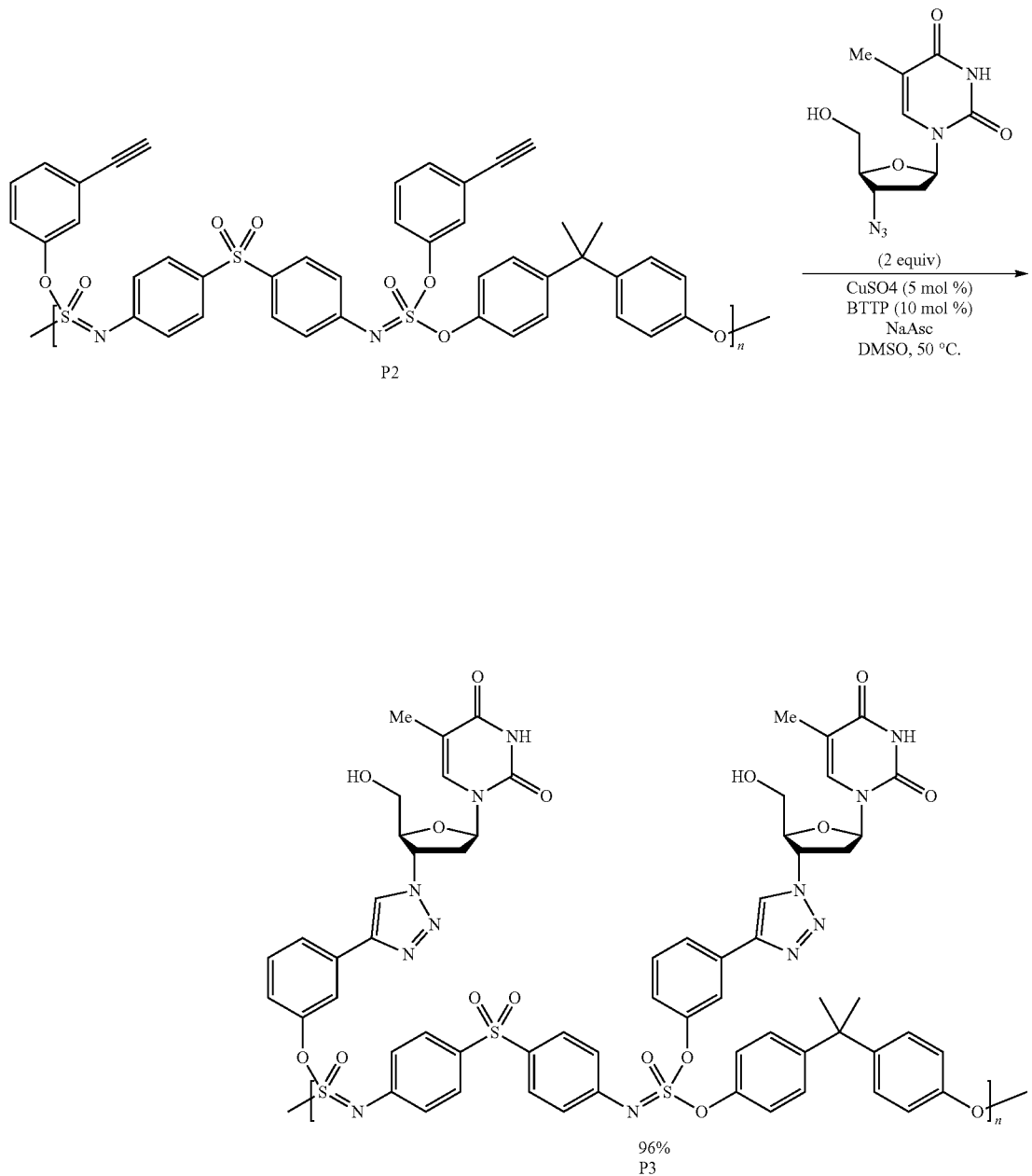

To a vial (20 mL) with magnetic stir was added the polymer P2 (160 mg), AZT (107 mg, 0.4 mmol), and 4 mL of DMSO. The mixture was stirred at room temperature until the solid was dissolved. To a 1 mL microcentrifuge tube was added CuSO$_4$ (0.01 mmol, 0.1 mL, 0.1 mol/L in H$_2$O), BTTP (9.0 mg, 0.02 mmol) and DMSO (0.1 mL). The mixture was shaken until all the BTTP was dissolved and then 25 mg of sodium ascorbate was added to this blue solution and the color was changed to light yellow immediately. This mixture was transferred to the 20 mL vial and the mixture was heated to 50° C. (oil bath) for 20 hours. The resulting solution was poured into 100 mL of MeOH slowly with stirring. The polymer was filtrated. The white solid was washed with MeOH three times (3 mL×3) and dried in the vacuum oven (60° C.) for 24 hours to give 255.5 mg of the polymer P3 (96%). $^1$H NMR (600 MHz, DMSO-d$_6$) δ 11.35 (s, 2H), 8.87 (s, 2H), 7.97-7.74 (m, 10H), 7.54 (t, J=7.9 Hz, 2H), 7.28 (d, J=8.1 Hz, 14H), 6.44 (t, J=6.6 Hz, 2H), 5.54-5.10 (m, 4H), 4.27 (q, J=4.1 Hz, 2H), 3.69 (ddd, J=41.5, 12.1, 3.6 Hz, 4H), 2.74 (dq, J=54.7, 6.9, 6.5 Hz, 4H), 1.80 (s, 6H), 1.57 (s, 6H); $^{13}$C NMR (151 MHz, DMSO) 163.72, 150.43, 150.19, 149.57, 147.50, 145.29, 145.01, 136.21, 135.95, 132.85, 131.08, 129.00, 128.51, 124.55, 123.80, 121.94, 121.10, 120.74, 117.78, 109.65, 84.40, 83.90, 60.71, 59.51, 42.33, 40.06, 37.14, 30.16, 12.26.

Ex. 76: Preparation of a Cross-Linking Polymer Using a Substrate with Three Iminosulfur Oxydifluoride Groups
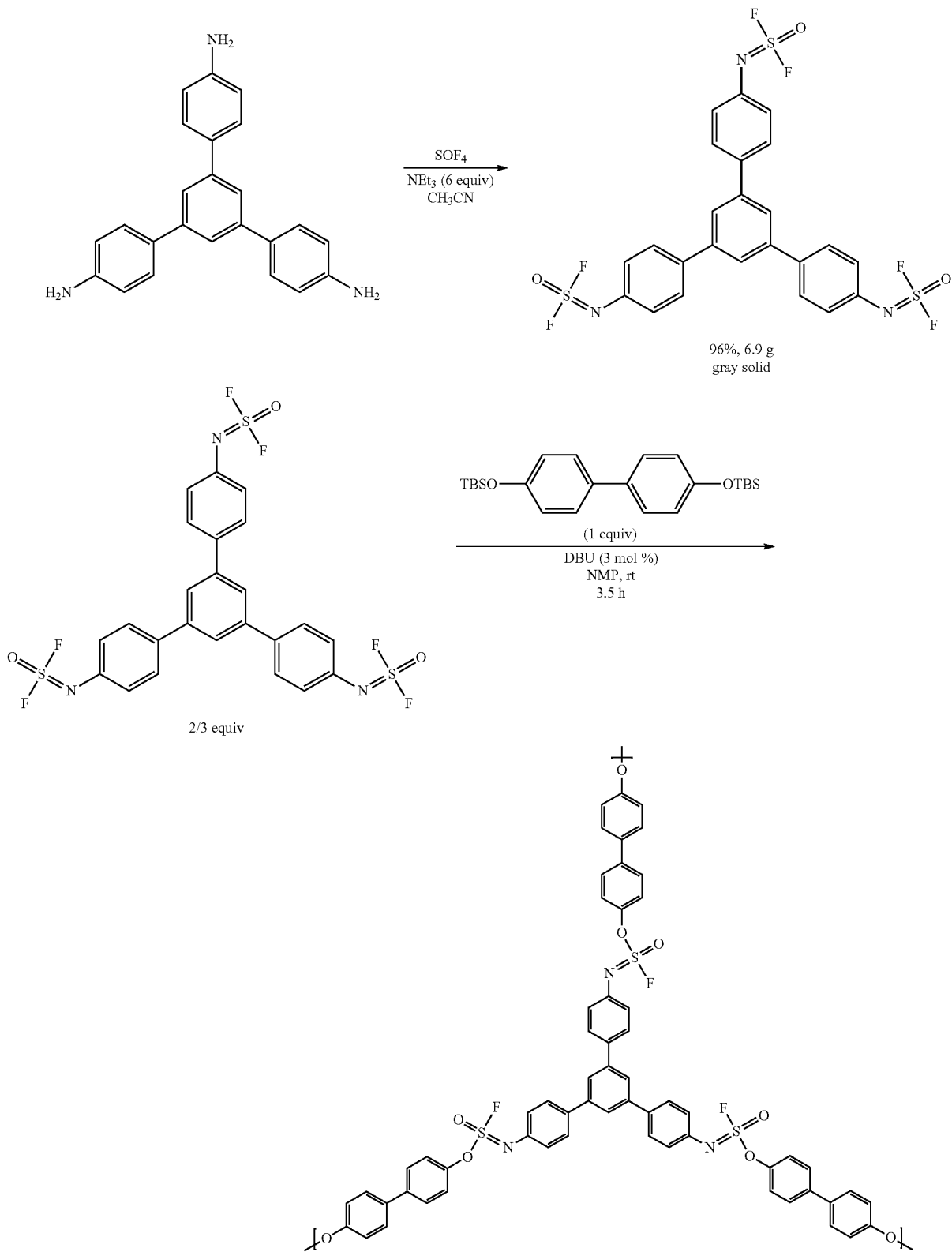

1,3,5-Tris(4-iminosulfuroxydifluorophenyl)benzene was prepared from the corresponding amino compound by the general method of Example 4 and reacted with 4,4'-bis-(t-butyldimethylsilyoxy)biphenyl according to the general method of Example 72 to form a crosslinked polymer. The final product was a gel with NMP and could not be dissolved in any common solvents.

Ex. 77: Reaction of Iminosulfur Oxyfluoride Polymer with Secondary Amine

The fluoride of any of the polymers described herein can be modified with a secondary amine as illustrated below.

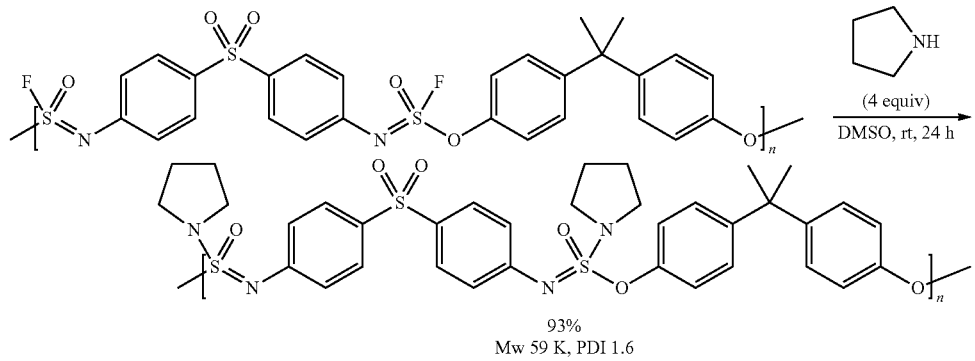

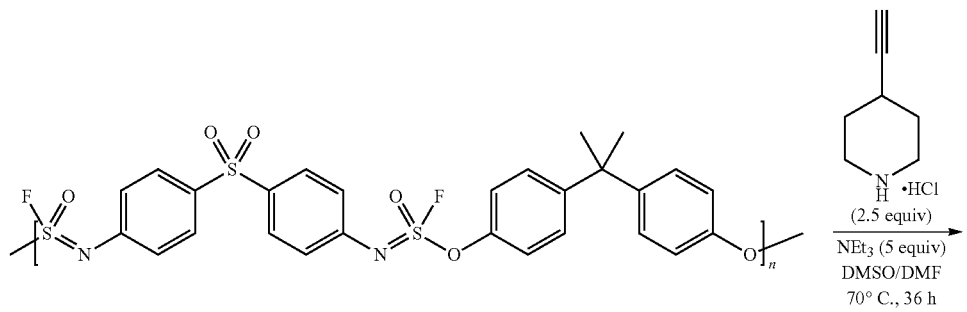

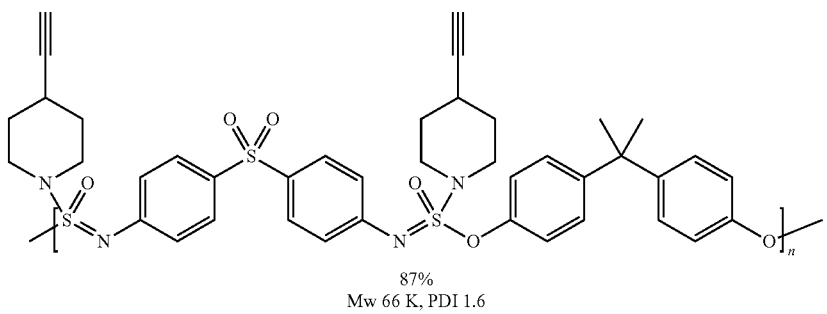

General Procedure: The starting polymer (1 mmol) and a secondary amine (or amine HCl salt with triethylamine) were dissolved in 5 mL of DMSO. The reaction was stirred at room temperature until the completion of substitution of all fluoride in the starting polymer (checked with $^{19}$F NMR). The resulting solution was poured into 50 mL of MeOH slowly with stirring. The solution was stirring in MeOH for 20 minutes and filtrated. The white solid was washed with MeOH three times (15 mL×3) and dried in the vacuum oven (60° C.) for 24 hours to give the polymer.

Ex. 78: Installation of Vancomycin into the Polymer Chain with a CuAAC Reaction

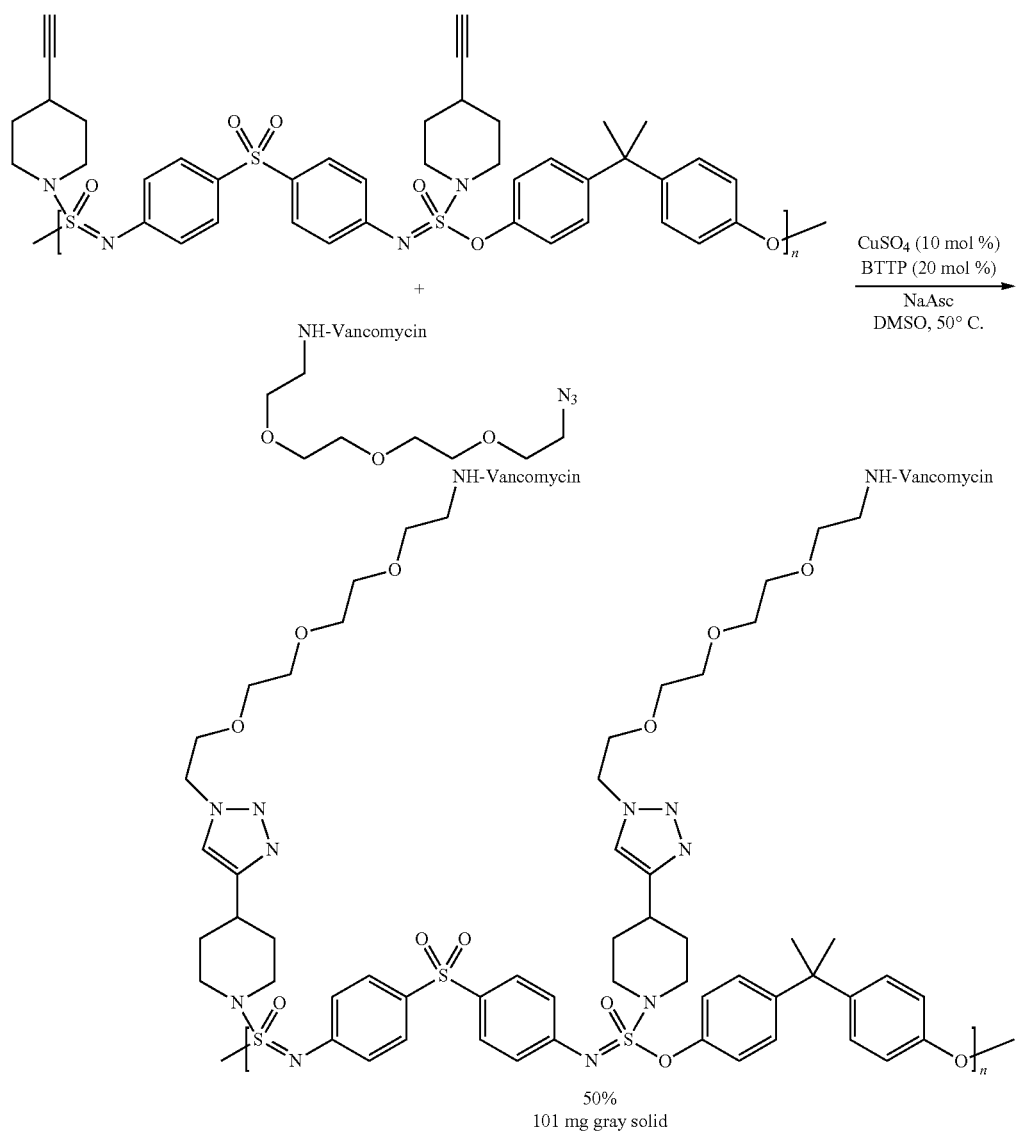

A vial (20 mL) with magnetic stirrer was added the polymer (39 mg), Vancomycin-azide (165 mg, 0.1 mmol) and 2 mL of DMSO. The mixture was stirred at room temperature until the solid was dissolved. To a 1 mL of microcentrifuge tube was added CuSO₄ (0.005 mmol, 0.05 mL, 0.1 mol/L in H₂O), BTTP (4.3 mg, 0.01 mmol) and DMSO (0.05 mL). The mixture was shaken until all the BTTP was dissolved and then 13 mg of sodium ascorbate was added to this blue solution and the color was changed to light yellow immediately. This mixture was transferred to the 20 mL vial and the mixture was heated to 50° C. (oil bath) for 20 hours. The resulting solution was poured into 15 mL of cold MeOH slowly with stirring. The polymer was filtrated. The white solid was washed with MeOH three times (2 mL×3) and dried in the vacuum oven (40° C.) for 24 hours to give the vancomycin polymer (101 mg, 50%) as gray solid.

Ex. 79: General Procedure for Making a Polymer with a N=S(=O)(—F)—N Type Linker

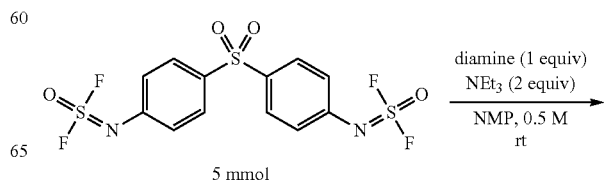

-continued

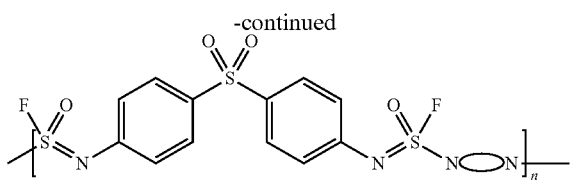

Figure 13:
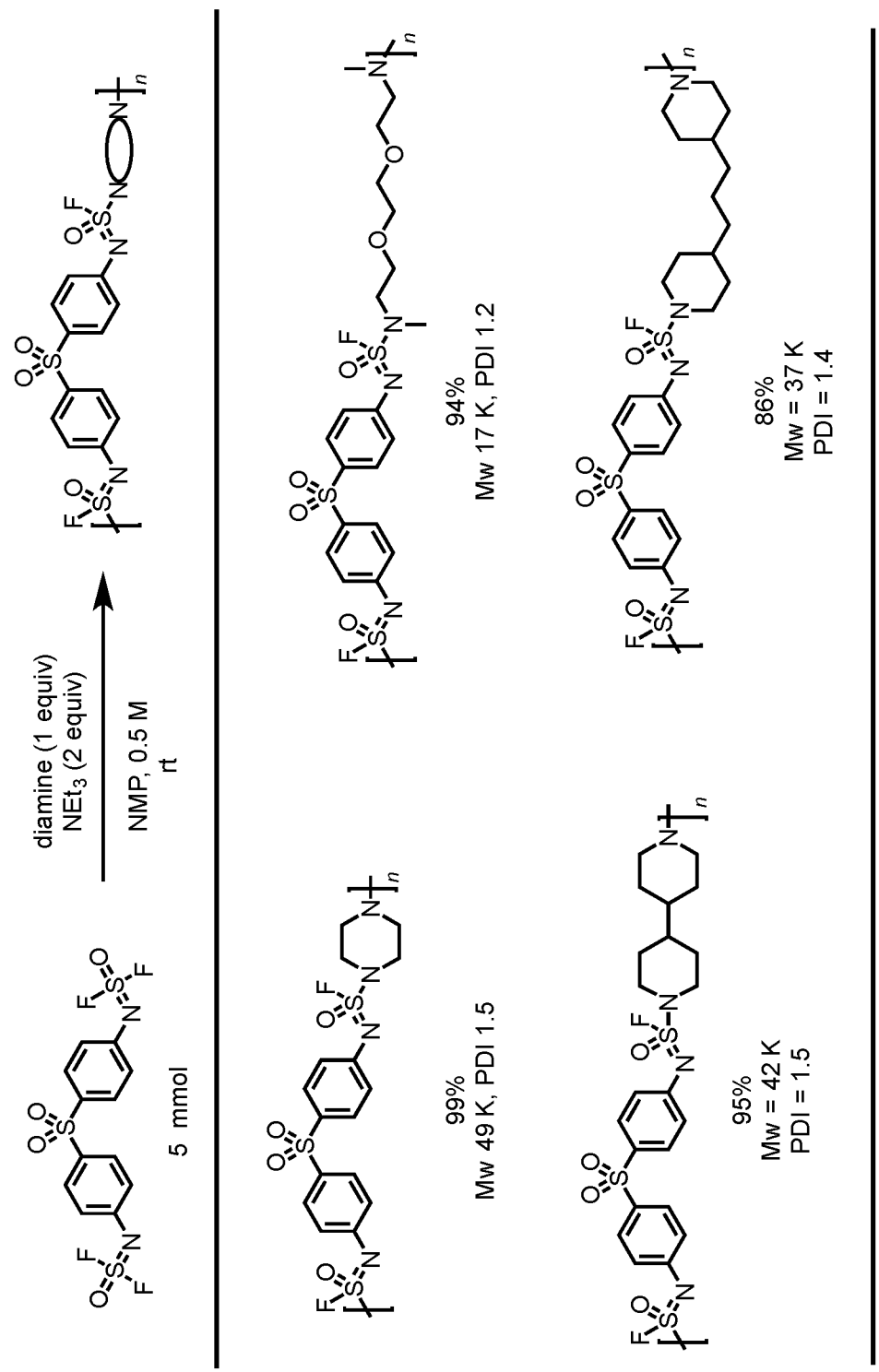
FIG. 13 illustrates the polymerization reaction using a N=S(=O)(—F)—N type linker.

A vial (20 mL) with magnetic stirrer was added the polymer (5 mmol), 10 mL of DMSO and triethylamine (10 mmol). Bis-amine (5 mmol) was added after the solid was dissolved. This mixture was stirring at room temperature for 3 hours and then the mixture was poured into 150 mL of MeOH slowly with stirring. The solution was stirring in MeOH for 20 minutes and filtrated. The solid was washed with MeOH three times (50 mL×3) and dried in the vacuum oven (60° C.) for 24 hours to give the N=S(=O)(—F)—N type linked polymer as a solid. Examples of polymers formed by this method are shown in FIG. 13.

Ex. 80: Preparation of Sulfonimidoyl Fluorides

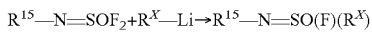

General Procedure: A 12 mL screw-capped borosilicate glass tube (Outer Diameter (O.D.)=16 mm, Length (L)=100 mm) equipped with a magnetic stir bar is flame-dried under vacuum and then filled with $N_2$ gas supplied by a balloon attached through a syringe. After the tube has cooled to room temperature, an iminosulfur oxydifluoride (0.2 mmol) and an aprotic solvent (e.g., cyclopentyl methyl ether, tetrahydrofuran, dibutyl ether, a hydrocarbon such as hexane, and the like, about 2 mL) are added. The tube is then cooled to about −78° C. in a dry ice/acetone bath, and an excess amount (e.g., about 1.3 to 2.2 equiv.) of an organo lithium compound ($R^X$—Li, preferably an aryl lithium compound, ArLi) in an aprotic solvent (e.g., cyclopentyl methyl ether, tetrahydrofuran, dibutyl ether, a hydrocarbon such as hexane, and the like) is added dropwise under vigorous stirring. The reaction is allowed to run for about 5 mins at the same temperature, and then is quenched by adding an acid (e.g., about 2 mL of 10 wt % acetic acid in methanol). The resulting mixture is warmed to room temperature and then transferred to a 50 mL round-bottomed flask. Solvent is removed on a rotary evaporator, and the sulfonimidoyl fluoride product is isolated via column chromatography. $R^{15}$ is a first organic group; $R^X$ can be any organic group compatible with organo lithium reagents, and preferably is an aryl group (Ar). The Ar group can be unsubstituted aromatic hydrocarbon, a substituted aromatic hydrocarbon, a heteroaromatic group, a substituted heteroaromatic group, and the like. The method is generally applicable to any combination of $R^{15}$, $R^X$, and Ar.

Compounds prepared by the General Procedure include Compounds II-1, II-2, II-3, II-4, II-13, II-22, II-23, II-25 and II-28 below, in the yields indicated.

II-1

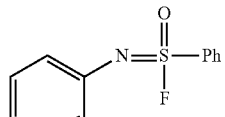

(±), 81% (0.5 g scale)

II-2

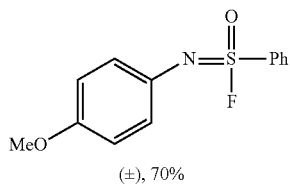

(±), 70%

II-3

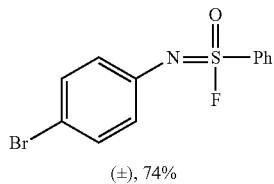

(±), 74%

II-4

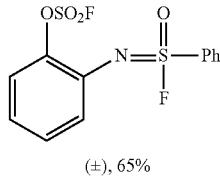

(±), 65%

II-13

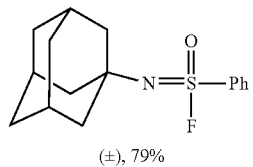

(±), 79%

II-22

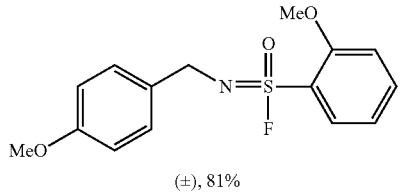

(±), 81%

II-23

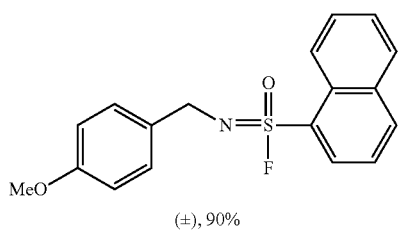

(±), 90%

II-25

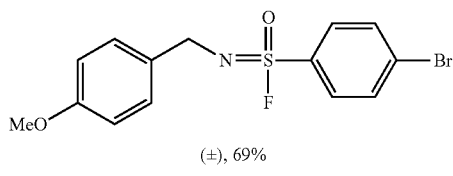

(±), 69%

II-28

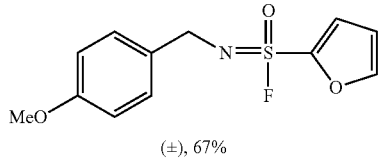

(±), 67%

As indicated in the structures above, all of the products were obtained as racemic mixtures (I).

Ex. 81: Preparation of Sulfoximines

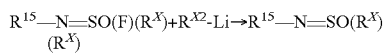

General Procedure: A 12 mL screw-capped borosilicate glass tube (O.D.=16 mm, L=100 mm) equipped with a magnetic stir bar is flame-dried under vacuum, and then is filled with $N_2$ gas supplied by a balloon attached through a syringe. After the tube has cooled to room temperature, a sulfonimidoyl fluoride as described in Example 80 ($R^{15}$—N=SO(F)($R^X$), 0.2 mmol) and an aprotic solvent (e.g., THF) (2 mL) are added. The resulting solution is cooled to about −78° C. in a dry ice/acetone bath. An organo lithium reagent ($R^{X2}$Li, 0.4 mmol) is added dropwise under vigorous stirring. The reaction is allowed to stir for about 5 mins at the same temperature and then is quenched by adding an acid (e.g., 2 mL of 10 wt % acetic acid in methanol). The resulting mixture is warmed to room temperature, transferred to a 50 mL round-bottomed bottle, and the solvent is removed on the rotary evaporator. The crude product is then purified by column chromatography. $R^{X2}$ is an organic group such as a saturated hydrocarbon, a substituted saturated hydrocarbon, aryl, substituted aryl, heteroaryl, a substituted heteroaryl, and the like, while $R^X$ and $R^{15}$ are as described in Example 80. The method is generally applicable to any combination of $R^{15}$, $R^X$, and $R^{X2}$.

Compounds prepared by the General Procedure include Compounds III-7 and III-10, below, in the yields indicated.

III-7

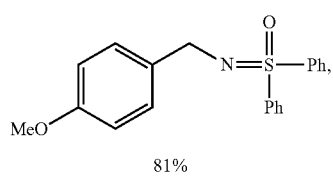

81%

III-10

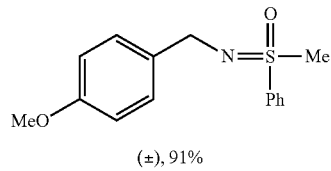

(±), 91%

Ex. 82: Preparation of Sulfonimidates

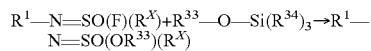

General Procedure: A 12 mL screw-capped borosilicate glass tube (O.D.=16 mm, L=100 mm) equipped with a magnetic stir bar is flame-dried under vacuum, and then is filled with $N_2$ gas supplied by a balloon attached through a syringe. After the tube has cooled to room temperature, sulfonimidoyl fluoride as described in Example 80 ($R^{15}$—N=SO(F)($R^X$), 0.2 mmol), a silylether ($R^{33}$—O—Si($R^{34}$)$_3$, 0.20 mmol), and an aprotic solvent (2 mL) is added. The vessel is then moved to a pre-heated oil bath (60° C.) and is stirred for about 5 mins. A catalyst selected from at least one member of the group consisting of an amidine base, a guanidine base, a phosphorine base, and a fluorine-containing anion (e.g., DBU, about 0.06 mmol) is added though a syringe and the reaction mixture is stirred for several hours (e.g., 10 hours) at the same temperature. The vessel is then cooled to room temperature and the crude product is transferred to a 50 mL round-bottomed bottle. Solvent is removed on a rotary evaporator and the crude product is purified by column chromatography. $R^{33}$ is an organic moiety, and each $R^{34}$ independently is an alkyl group, an aryl group, an arylalkyl group or an alkylaryl group. The method is generally applicable to any combination of $R^{15}$, $R^X$, $R^{33}$, and $R^{34}$.

Compounds prepared by the General Procedure include Compounds IV-2 and IV-3, below, in the yields indicated.

IV-2

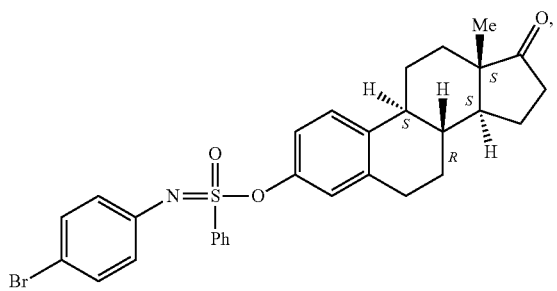

97%

IV-3

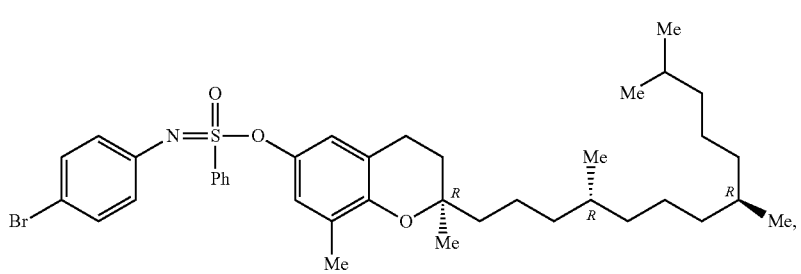

88%

Ex. 83: Preparation of Sulfonimidamides

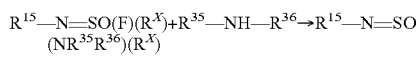

General Procedure: A sulfonimidoyl fluoride as described in Example 80 ($R^{15}$—N=SO(F)($R^X$), 0.2 mmol), an amine ($R^{35}$—NH—$R^{36}$, 0.4 mmol), a solvent (e.g., $CH_3CN$) (2.0 mL), and then a catalyst selected from at least one member of the group consisting of an amidine base, a guanidine base, a phosphorine base, and a fluorine-containing anion (e.g., DBU) (0.4 mmol) are added to a 12 mL screw-capped borosilicate glass tube (O.D.=16 mm, L=100 mm) equipped with a magnetic stir bar under a nitrogen atmosphere. The vessel is moved to a pre-heated oil bath (60° C.) and is stirred until full conversion of the sulfonimidoyl fluoride is observed by TLC (e.g., for about 24 hours). Subsequently, the vessel is cooled to room temperature and the resulting mixture is transferred to a 50 mL round-bottomed bottle. Solvent is removed on a rotary evaporator and the crude product is purified by column chromatography. The amine $R^{35}$—NH—$R^{36}$ can be a secondary amine (e.g., a substituted or unsubstituted amine wherein $R^{35}$ and $R^{36}$ each comprise an organic group) or a heterocyclic secondary amine (i.e., $R^{35}$ and $R^{36}$ together with the N atom of the amine form a ring structure). The method is generally applicable to any combination of $R^{15}$, $R^X$, $R^{35}$, and $R^{36}$.

Compounds prepared by the General Procedure include Compounds V-1 and V-2, below, in the yields indicated.

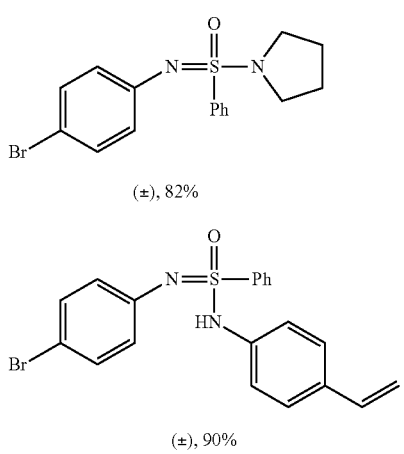

Ex. 84: Preparation of Iminosulfur Oxydifluorides Using a Solution of Thionyl Tetrafluoride In an alternative to the procedure described in Example 2, the thionyl tetrafluoride can be added to the primary amine as a pre-prepared solution in an aprotic solvent. For example, gaseous thionyl tetrafluoride can be dissolved in acetonitrile to form a stable solution. The concentration of thionyl tetrafluoride in the solution can be determined gravimetrically (e.g., by weighing the acetonitrile before and after adding the $SOF_4$) or by spectroscopic means (e.g., UV-Vis spectroscopy). Two example of iminosulfur oxydifluoride preparation utilizing an acetonitrile solution are shown below. The amines were reacted with an excess of thionyl tetrafluoride/acetonitrile solution in the presence of 10 equivalents of triethylamine ($Et_3N$) in acetonitrile to afford the iminosulfur difluorides in high yields (see Schemes 84A and 84 B, below). In the case of Scheme 84B, the amino phenol compound was simultaneously treated with solution of $SOF_4$ in acetonitrile and sulfuryl fluoride ($SO_2F_2$) in acetonitrile. As shown in Scheme 84B, the $SOF_4$ selectively reacted with the amino group, whereas the $SO_2F_2$ reacted with the phenol, further illustrating the high selectivity for the reactions $SOF_4$ and $SO_2F_2$ reactions with primary amines and phenols, respectively.

Schemes 84A and 84B

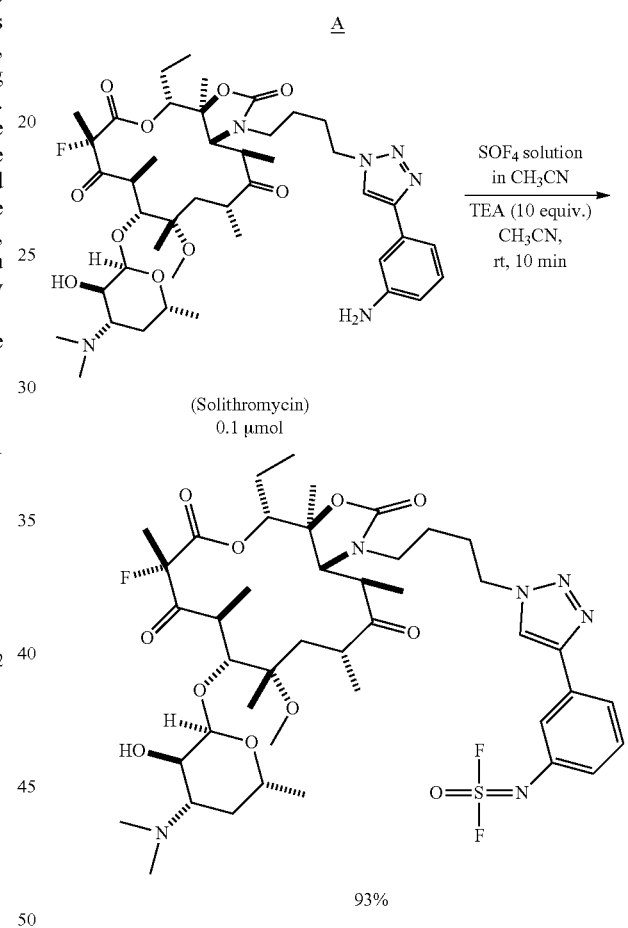

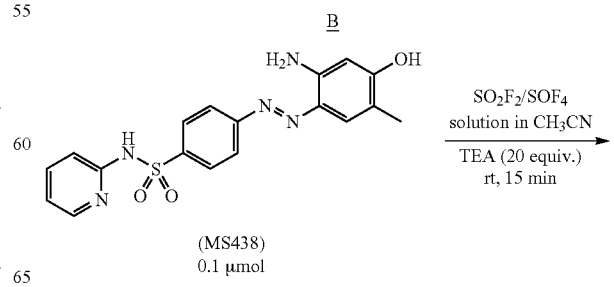

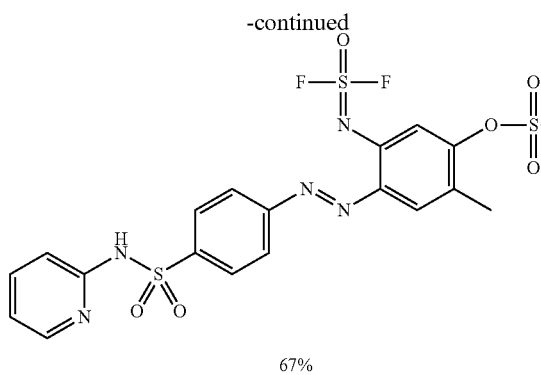

67%

REFERENCES (1) (a) Sharpless, K. B.; Kolb, H. C. *Book of Abstracts*, 217th ACS National Meeting, Anaheim, Calif., Mar. 21-25, 1999, ORGA-105, Accession Number 199:145537. (b) Kolb, H. C.; Finn, M. G.; Sharpless, K. B. *Angew. Chem. Int. Ed.* 2001, 40, 2004.

(2) (a) Rostovtsev, V. V.; Green, L. G.; Fokin, V. V.; Sharpless, K. B. *Angew. Chem. Int. Ed.* 2002, 41, 2596. (b) Torne, C. W.; Christensen, C.; Meldal, M. *J. Org. Chem.* 2002, 67, 3057.

(3) (a) For examples see: Xi, W.; Scott, T. F.; Kloxin, C. J.; Bowman, C. N. *Adv. Funct. Mater.* 2014, 24, 2572. (b) Liu, Y.; Diaz, D. D.; Accurso, A. A.; Sharpless, K. B.; Fokin V. V.; Finn, M. G. *J. Polymer Sci., Part A*. 2007, 45, 5182. (c) Diaz, D. D.; Punna, S.; Holzer, P.; McPherson, A. K.; Sharpless, K. B.; Fokin, V. V.; Finn, M. G. *J. Polym. Sci. Part A: Polym. Chem.* 2004, 42, 4392. (d) Wu, P.; Feldman, A. K.; Nugent, A. K.; Hawker, C. J.; Scheel, A.; Voit, B.; Pyun, J.; Frechet, J. M. J.; Sharpless, K. B.; Fokin, V. V. *Angew. Chem. Int. Ed.*, 2004, 43, 3928.

(4) (a) Rouhanifard, S. H.; Nordstrom, L. U.; Zheng, T.; Wu, P. *Chem. Soc. Rev.* 2013, 42, 4284. (b) McKay, C. S.; Finn, M. G. *Chem. Biol.* 2014, 21, 1075.

(5) (a) Kolb, H. C.; Sharpless, K. B. *Drug Discov. Today* 2003, 8, 1128. (b) Thirumurugan, P.; Matosiuk, D.; Jozwiak, K. *Chem. Rev.* 2013, 113, 4905.

(6) Moses, J. E.; Moorhouse, A. D. *Chem. Soc. Rev.* 2007, 36, 1249.

(7) Dong, J.; Krasnova, L.; Finn, M. G.; Sharpless, K. B. *Angew. Chem. Int. Ed.* 2014, 53, 9430.

(8) The catalysis is exceedingly facile and not yet fully understood.

(9) Gembus, V.; Marsais, F.; Levacher, V. *Synlett*, 2008, 1463.

(10) Barrow, A. S.; Moses, J. E. *Synlett*, 2016, 27, 1480.

(11) Dong, J.; Sharpless, K. B.; Kwisnek, L.; Oakdale, J. S.; Fokin, V. V. *Angew. Chem. Int. Ed.* 2014, 53, 9466.

(12) Yatvin, J.; Brooks, K.; Locklin, J. *Angew. Chem., Int. Ed.* 2015, 54,13370.

(13) Oakdale, J. S.; Kwisnek, L.; Fokin, V. V. *Macromolecules*, 2016, 49, 4473.

(14) (a) As a fumigant, sulfuryl fluoride ($SO_2F_2$) has been produced annually at more than 3 million kilograms per year since 2000, with a price as low as $1/kg. see Andersen, M. P. S.; Blake, D. R.; Rowland, F. S.; Hurley, M. D.; Wallington, T. *J. Environ. Sci. Technol.* 2009, 43, 1067. (b) We and others in North America have purchased multi-kilogram amounts of sulfuryl fluoride, $SO_2F_2$, from Synquest Laboratories Inc., Alachua, Fla. 32616 (http://www.synquestlabs.com). It is shipped by truck, and in our case arrived in under two weeks.

(15) (a) Zhang, E.; Tang, J.; Li, S.; Wu, P.; Moses, J. E.; Sharpless, K. B. *Chem. Eur. J.* 2016, 22, 5692.

(16) (a) Chen, W.; Dong, J.; Plate, L.; Mortenson, D. E.; Brighty, G. J.; Li, S.; Liu, Y.; Galmozzi, A.; Lee, P. S.; Hulce, J. J.; Cravatt, B. F.; Saez, E.; Powers, E. T.; Wilson, I. A.; Sharpless, K. B.; Kelly, J. W. *J. Am. Chem. Soc.* 2016, 138, 7353. (b) Narayanan, A.; Jones, L. H. *Chem. Sci.* 2015, 6, 2650.

(17) (a) Cowen, H. C.; Rinding, F.; Warhurst, E. *J. Chem. Soc.* 1953, 4168. (b) Siegel, B.; Breisacher, P. *J. Inorg. Nucl. Chem.* 1970, 32, 1469. (c) Brewer, L.; Chang, C. A.; King, B. A. *Inorg. Chem.* 1970, 9, 814. (d) https://en.wikipedia.org/wiki/Sulfur_hexafluoride#cite_note-6.

(18) (a) Moissan, H.; Lebeau, P. *Compt. Rend.* 1901, 132, 374. (b) Moissan, H.; Lebeau, P. *Ann. Chim. Et. Phys.* 1902, 26, 145.

(19) Jonas, H. *Z. Anorg. Allg. Chem.* 1951, 265, 273.

(20) Dudley, F. B.; Cady, G. H.; Eggers Jr., D. F. *J. Am. Chem. Soc.* 1956, 78, 1553.

(21) Smith, W. C.; Engelhardt, V. A. *J. Am. Chem. Soc.* 1960, 82, 3838.

(22) (a) Cramer, R.; Coffman, D. D. *J. Org. Chem.* 1961, 26, 4010. (b) Cramer, R. D. U.S. Pat. No. 3,410,669 A 1968.

(23) Including the initial anchoring step, introducing the imido ligand and leaving two fluorides.

(24) Although they are all stable to silica gel chromatography and TLC analysis.

(25) (a) Soriano del Amo, D.; Wang, W.; Jiang, H.; Besanseney, C.; Yan, A, C.; Levy, M.; Liu, Y.; Marlow, F. Wu, P. *J. Am. Chem. Soc.* 2010, 132, 16893; (b) Wang, W.; Hong, S.; Tran, A.; Jiang, H.; Triano, R.; Liu, Y. Chen, X.; Wu, P. *Chem. Asian J.* 2011, 6, 2796.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound of formula $R^1$—N=S(O)$(X^4)_2$, wherein $R^1$ comprises at least one first organic moiety selected from the group consisting of:
   (a) a carbohydrate,
   (b) a polymer,
   (c) a polypeptide,
   (d) a nucleotide,
   (e) a nucleic acid,
   (f) an enzyme, and
   (g) a nucleoside moiety;
   wherein each $X^4$ independently is F, $OR^x$, $N(R^x)_2$, or NHet, each $R^x$ independently is a second organic moiety selected from the group consisting of alkyl, aryl, or heteroaryl; and NHet comprises a heterocyclic moiety bonded to S by a nitrogen-sulfur covalent bond.

2. The compound of claim 1, wherein $R^1$ comprises an amino-substituted polymer and the $-N=S(O)(X^A)_2$ group replaces at least one amino group of the polymer.

3. The compound of claim 1, wherein $R^1$ comprises a polypeptide.

4. The compound of claim 3, wherein the polypeptide comprises a lysine residue and the $-N=S(O)(X^A)_2$ replaces the sidechain amino group of the lysine residue.

5. The compound of claim 1, wherein the $R^1$ comprises one or more substituents selected from the group consisting of functional groups hydroxyl, halogen, nitro, $-C(O)R^{30}$, $-C(O)OR^{30}$, $-C(O)N(R^{30})_2$, $-CN$, $-SO_vR^{30}$, $-SO_vN(R^{30})_2$, $R^{30}SO_vN(R^{30})-$, $-N(R^{30})SO_vR^{30}$, $-SO_3R^{30}$, $-N(R^{30})_2$, $-N(R^{30})OR^{30}$, $-N(R^{30})C(O)R^{30}$, $-N(R^{30})C(O)OR^{30}$, $-N(R^{30})C(O)N(R^{30})_2$, $-OC(O)N(R^{30})_2$, $-OC(O)OR^{30}$, azido, alkyl, cycloalkyl, alkenyl, alkynyl, alkoxy, fluoroalkyl, fluoroalkoxy, aryl, aryloxy, heteroaryl, poly(ethyleneoxy), alkynyl-terminated poly(ethyleneoxy), a fatty acid, a carbohydrate, an amino acid, a polypeptide; wherein each $R^{30}$ independently is H, alkyl, or aryl, and v is 0, 1, or 2.

6. The compound of claim 1, wherein both $X^A$ groups are F.

7. A method for preparing an iminosulfur oxydifluoride compound of claim 6, comprising contacting an amino compound of formula $R^1-NX_2$ with thionyl tetrafluoride to form an iminosulfur oxydifluoride compound of formula $R^1-N=SOF_2$;
wherein:
each X independently is H or $Si(R^{16})_3$;
each $R^{16}$ independently is an alkyl group, an aryl group, an arylalkyl group or an alkylaryl group; and
the thionyl tetrafluoride is supplied as a gas or as a solution in an aprotic solvent;
with the proviso that when both X groups are H, the amino compound is contacted with the thionyl tetrafluoride in the presence of a tertiary amine.

8. A method of preparing an iminosulfur oxyfluoride polymer comprising contacting a bis-(iminosulfur oxydifluoride) monomer with a bis-(silyl ether) monomer in the presence of a catalyst for the iminosulfur oxyfluoride polymer; wherein the catalyst is selected from at least one member of the group consisting of an amidine base, a guanidine base, a phosphorine base, and a fluorine-containing anion.

9. The method of claim 8, wherein the bis(iminosulfur oxydifluoride) monomer is a compound of Formula (III):

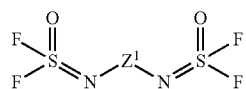

(III)

the bis-(silyl ether) monomer is a compound of Formula (IV):

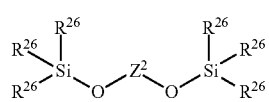

(IV)

and the iminosulfur oxyfluoride polymer is a compound of Formula (V):

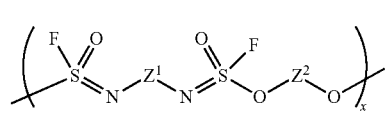

(V)

wherein:
x is the average number of repeating units in the polymer, and has a value selected from the group consisting of greater than 1, greater than 10, greater than 20, greater than 30, greater than 50, greater than 100, greater than 1000; and greater than 10,000;
each of $Z^1$ and $Z^2$ independently is a divalent organic group; and
each $R^{26}$ independently is an alkyl group, an aryl group, an arylalkyl group or an alkylaryl group.

10. The method of claim 9, wherein each of $Z^1$ and/or $Z^2$ independently is a divalent organic group of Formula (VI):

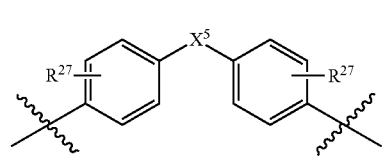

(VI)

wherein:
$X^5$ is selected from $-CH_2-$, $-CH(R^{28})-$, $-C(R^{28})_2-$, $-R^{28}-$, $-OR^{28}O-$, $-O-$, $-S-$, and $-SO_2-$;
each $R^{27}$ independently is a substituent selected from a halogen, an alkyl, an alkoxy, an aryl, an alkylaryl, an arylalkyl, and a heteroatom-containing substituent comprising one or more oxygen, nitrogen, or sulfur atoms, optionally in combination with carbon and hydrogen;
$R^{28}$ is selected from alkyl, aryl, arylalkyl, and alkylaryl; and
each y independently is 0, 1, 2, 3, and 4.

11. The method of claim 9, wherein each of $Z^1$ and/or $Z^2$ independently is a divalent organic group of Formula (VII):

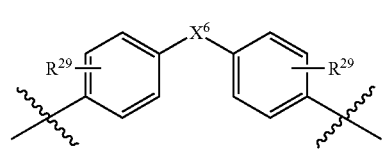

(VII)

wherein each $R^{29}$ independently is a hydrocarbyl group, and $X^6$ is a covalent bond, $-C(CH_3)_2-$, $-C(CF_3)_2-$, or $-SO_2-$.

12. The method of claim 8, comprising contacting the bis-(iminosulfur oxydifluoride) monomer and the a bis-(silyl ether) monomer with a cross-linking monomer comprising at least three iminosulfur oxydifluoride groups in the presence of the catalyst to form a crosslinked iminosulfur oxyfluoride polymer.

13. The method of claim 8, comprising contacting the bis-(iminosulfur oxydifluoride) monomer and the a bis-(silyl ether) monomer with a cross-linking monomer comprising at least three silyl ether groups in the presence of the catalyst to form a crosslinked iminosulfur oxyfluoride polymer.

14. The compound of claim 1, wherein the $R^1$ is a polymer and the compound is an iminosulfur oxyfluoride polymer of Formula (V):

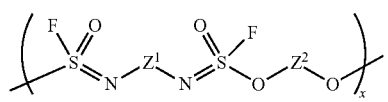

wherein:
x is the average number of repeating units in the polymer, and has a value selected from the group consisting of greater than 1, greater than 10, greater than 20, greater than 30, greater than 50, greater than 100, greater than 1000; and greater than 10,000; and
each of $Z^1$ and $Z^2$ independently is a divalent organic group.

15. The polymer of claim 14, wherein each of $Z^1$ and/or $Z^2$ independently is a divalent organic group of Formula (VI):

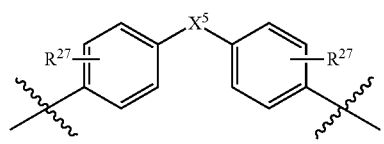

wherein:
$X^5$ is selected from —$CH_2$—, —$CH(R^{28})$—, —$C(R^{28})_2$—, —$R^{28}$—, —$OR^{28}O$—, —O—, —S—, and —$SO_2$—;
each $R^{27}$ independently is a substituent selected from a halogen, an alkyl, an alkoxy, an aryl, an alkylaryl, an arylalkyl, and a heteroatom-containing substituent comprising one or more oxygen, nitrogen, or sulfur atoms, optionally in combination with carbon and hydrogen;

$R^{28}$ is selected from alkyl, aryl, arylalkyl, and alkylaryl; and
each y independently is 0, 1, 2, 3, and 4.

16. A compound of formula $R^1$—N=S(O)$(X^4)_2$ wherein:
each $X^A$ is F; and
$R^1$ is selected from the group consisting of a nucleoside, a nucleotide, and a nucleic acid.

17. The compound of claim 16, wherein $R^1$ is a nucleoside.

18. The compound of claim 17, wherein the nucleoside comprises a purine or pyrimidine base linked through the N-9 nitrogen atom of the purine or the N-1 nitrogen atom of the pyrimidine to C-1 of (a) a beta-D-ribofuranose moiety, or (b) a beta-D-deoxyribofuranose moiety.

19. The compound of claim 18, wherein the purine or pyrimidine base is linked to the C-1 of a beta-D-ribofuranose moiety.

20. The compound of claim 17, wherein the compound is:

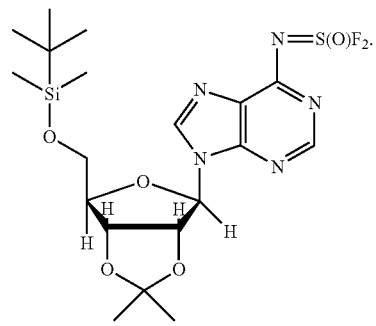

21. A nucleotide comprising an orthophosphate or oligophosphate bound to the 5' hydroxyl group of a nucleoside; wherein the nucleoside is the compound of claim 17.

22. A nucleic acid comprising multiple nucleotides bound together through phosphodiester linkages between the 5' hydroxyl of one nucleotide unit and the 3' hydroxyl group of an adjacent nucleotide unit thereby forming a generally linear chain of nucleotide units, wherein the chain of nucleotide units comprises the nucleotide of claim 21.

* * * * *